US006849639B2

(12) United States Patent
Dominguez et al.

(10) Patent No.: US 6,849,639 B2
(45) Date of Patent: Feb. 1, 2005

(54) INTEGRIN INHIBITORS AND THEIR METHODS OF USE

(75) Inventors: Celia Dominguez, Thousand Oaks, CA (US); Guoqing Chen, Thousand Oaks, CA (US); Ning Xi, Thousand Oaks, CA (US); Shimin Xu, Moorpark, CA (US); Nianhe Han, Thousand Oaks, CA (US); Qingyian Liu, Thousand Oaks, CA (US); Qi Huang, Moorpark, CA (US); Aaron Siegmund, Ventura, CA (US); Michael Handley, Ventura, CA (US); Longbin Liu, Thousand Oaks, CA (US); Alexander Kiselyov, New York, NY (US)

(73) Assignee: Amgen Inc., Thousand Oaks, CA (US)

( * ) Notice: Subject to any disclaimer, the term of this patent is extended or adjusted under 35 U.S.C. 154(b) by 557 days.

(21) Appl. No.: 09/732,546

(22) Filed: Dec. 8, 2000

(65) Prior Publication Data

US 2002/0019402 A1 Feb. 14, 2002

Related U.S. Application Data

(60) Provisional application No. 60/170,824, filed on Dec. 24, 1999.

(51) Int. Cl.$^7$ .................... C07D 401/12; C07D 403/12; A61K 31/4025
(52) U.S. Cl. ................ 514/275; 514/314; 514/318; 514/333; 514/341; 514/342; 514/343; 514/422; 514/424; 544/331; 544/332; 546/175; 546/194; 546/256; 546/270.7; 546/274.7; 546/278.4; 548/314.7; 548/526; 548/527; 548/547; 548/550
(58) Field of Search ................ 544/331, 332; 546/175, 194, 256, 270.7, 274.7, 278.4; 548/314.7, 526, 527, 547, 550; 514/275, 314, 318, 333, 341, 342, 343, 422, 424

(56) References Cited

U.S. PATENT DOCUMENTS

| | | | |
|---|---|---|---|
| 5,721,366 A | * | 2/1998 | Abood et al. ............... 546/292 |
| 5,843,906 A | | 12/1998 | Chandrakumar et al. ...... 514/19 |
| 5,849,736 A | | 12/1998 | Wityak et al. ........... 514/227.8 |
| 5,952,306 A | | 9/1999 | Hartman et al. ............... 514/18 |
| 5,952,341 A | | 9/1999 | Duggan et al. ............. 514/300 |

FOREIGN PATENT DOCUMENTS

| | | |
|---|---|---|
| EP | 039 051 | 11/1981 |
| WO | WO 97/08145 | 3/1997 |
| WO | WO 97/35615 | 10/1997 |
| WO | WO 97/36862 | 10/1997 |
| WO | WO 98/18461 | 5/1998 |
| WO | WO 99/30709 | 6/1999 |
| WO | WO 99/30713 | 6/1999 |
| WO | WO 99/31099 | 6/1999 |
| WO | WO 99/32457 | 7/1999 |
| WO | WO 99/33798 | 7/1999 |
| WO | WO 99/37621 | 7/1999 |
| WO | WO 99/50249 | 10/1999 |
| WO | WO 99/58139 | 11/1999 |
| WO | WO 99/67230 | 12/1999 |

OTHER PUBLICATIONS

Douglas, Jr., Introduction to Viral Diseases, Cecil Textbook of Medicine, 20th Edition, vol. 2, pp. 1739–1747, 1996.*
Simone, Oncology: Introduction, Cecil Textbook of Medicine, 20th Edition, vol. 1, pp. 1004–1010, 1996.*
Agrez et al. (1994), "The αvβ6 Integrin Promotes Proliferation of Colon Carcinoma Cells through a Unique Region of the β6 Cytoplasmic Domain", *J. Cell Biol.* 127:547–556.
Agrez et al. (1997), "Integrin αvβ6 Enhances Coxsackievisus B1 Lytic Infection of Human Colon Cancer Cells", *Virology*, 239:71–77.
Agrez et al. (1999), "The αvβ6 Integrin Induces Gelatinase B Secretion in Colon Cancer Cells", *Int. J. Cancer* 81:90–97.
Albericio et al. (1998), "Use of Onium Salt–Based Coupling Reagents in Peptide Synthesis", *J. Org. Chem.* 63:9678–9683.
Arner et al. (1995), "Signal Transduction Through Chondrocyte Integrin Receptors Induces Matrix Metalloproteinase Synthesis and Synergizes with Interleukin–1", *Arthritis & Rheumatism* 38(9):1304–1314.
Baati et al. (1999), "An Improved Method for the Preparation of Amidines via Thiophenylimidic Esters", *Synthesis* 6:927–929.
Beller et al., "Palladium–catalyzed Olefinations of Aryl Halides (Heck Reaction) and Related Transformations" in *Transition Metals for Organic Synthesis* (Wiley–VCH, Beller et al. (ed.) (1998)) pp. 208–240.
Berge et al. (1977), "Pharmaceutical Salts", *J. Pharm. Sci* 66(1):1–19.
Brooks (1997), "Integrin αvβ3: A Therapeutic Target", *Drug News Perspect.* 10(8):456–461.
Brooks et al. (1997), "Insulin–like Growth Factor Receptor Cooperates With Integrin αvβ5 to Promote Tumor Cell Dissemination In Vivo", *J. Clin. Invest.* 99(6): 1390–1398.
Bundgaard et al. (1989), "A Novel Solution–Stable, Water–Soluble Prodrug Type for Drugs Containing a Hydroxyl or an NH–Acidic Group", *J. Med. Chem.* 32(12):2503–2507.
Busk et al. (1992), "Characterization of Integrin αvβ6 as a Fibronectin–binding Protein", *J. Biol. Chem.* 267(9):5790–5796.

(List continued on next page.)

*Primary Examiner*—Deepak Rao
(74) *Attorney, Agent, or Firm*—MarySusan Howard; Ron K. Levy; Stuart L. Watt

(57) ABSTRACT

The invention comprises novel compounds that are effective in the prophylaxis and treatment of diseases, such as integrin receptors mediated diseases, in particular, diseases or conditions mediated by integrin receptors, such as a $\alpha_v\beta_3$, $\alpha_v\beta_5$, $\alpha_v\beta_6$, $\alpha_5\beta_1$ and the like. The invention encompasses novel compounds, pharmaceutically acceptable salts thereof, pharmaceutical compositions and methods for prophylaxis and treatment of such diseases and disorders. The subject invention also relates to processes for making such compounds as well as to intermediates useful in such processes.

8 Claims, No Drawings

OTHER PUBLICATIONS

Carpino et al. (1999), "The Diisopropylcarbodiimide/1-Hydroxy-7-azabenzotriazole System: Segment Coupling and Stepwise Peptide Assembly", *Tetrahedron* 55:6813–6830.

Carreiras et al. (1999), "Migration Properties of the Human Ovarian Adenocarcinoma Cell Line IGROV1: Importance of αvβ3 Integrins and Vitronectin", *Int. J. Cancer* 80:285–294.

Carron et al. (1998), "A Peptidomimetic Antagonist of the Integrin $\alpha_v\beta_3$ Inhibits Leydig Cell Tumor Growth and the Development of Hypercalcemia of Malignancy", *Cancer Res.* 58:1930–1935.

Cheng et al. (1973), "Relationship Between the Inhibition Constant ($K_1$) and the Concentration of Inhibitor Which Causes 50 Per Cent Inhibition $I_{50}$) of an Enzymatic Reaction", *Biochem. Pharmacology* 22:3099–3108.

Cheresh (1991), "Structure, function and biological properties of integrin $\alpha_v\beta_3$ on human melanoma cells", *Cancer and Metastasis Rev.* 10:3–10.

Clark et al. (1996), "Transient Functional Expression of αvβ3 on Vascular Cells during Wound Repair", *Am. J. Pathol.* 148(5):1407–1421.

Dunn, "Amidines and N-Substituted Amidines" in *Compr. Org. Funct. Group Transform.* vol. 5 (Pergamon (1995)) pp. 741–782 and 1161–1308.

Gautier et al., "Preparation and synthetic uses of amidines" in *Chem. Amidines Imidates* Ch. 7 (Patai (ed), Wiley & Sons (1975)) pp. 283–348.

Gladson et al. (1997), "Vitronectin Expression in Differentiating Neuroblastic Tumors", *Am. J. Pathol.* 150(5):1631–1646.

Gonda (1990), "Aerosols for Delivery of Therapeutic and Diagnostic Agents to the Respiratory Tract", *Critical Review in Therapeutic Drug Carrier Systems* 6(4):273–313.

Haapasalmi et al. (1996), "Keratinocytes in Human Wounds Express αvβ6 Integrin", *J. Invest. Dermatol.* 106(1):42–48.

Hermann et al. (1999), "The Vitronectin Receptor and its Associated CD47 Molecule Mediates Proinflammatory Cytokine Synthesis in Human Monocytes by Interaction with Soluble CD23", *J. Cell Biol.* 144(4):767–775.

Horton (1997), "The αvβ3 Integrin Vitronectin Receptor", *Int. J. Biochem. Cell Biol.* 29(5):721–725.

Huang et al. (1996), "Inactivation of the Integrin β6 subunit Gene Reveals a Role of Epithelial Integrins in Regulating Inflammation in the Lungs and Skin", *J. Cell Biol.* 133(4):921–928.

Keenan et al. (1997), "Discovery of Potent Nonpeptide Vitronectin Receptor ($\alpha_v\beta_3$) Antagonists", *J. Med. Chem.,* 40(15):2289–2292.

Kim et al. (1994), "Vitronectin-driven Human Keratinocyte Locomotion Is Mediated by the αvβ5 Integrin Receptor", *J. Biol. Chem.* 269(43):26926–26932.

Marcinkiewicz et al. (1996), "One–Step Affinity Purification of Recombinant $\alpha_v\beta_3$ Integrin from Transfected Cells", *Protein Expression and Purification* 8:68–74.

Maryanoff et al. (1989), "The Wittig Olefination Reaction and Modifications Involving Phosphoryl–Stabilized Carbanions. Stereochemistry, Mechanism, and Selected Synthetic Aspects", *Chem. Rev.* 89:863–927.

Munger et al. (1999), "The Integrin αvβ6 Binds and Activates Latent TGFβ1: A Mechanism for Regulating Pulmonary Inflammation and Fibrosis", *Cell* 96:319–328.

Natali et al. (1997), "Clinical Significance of $\alpha_v\beta_3$ Integrin and Intercellular Adhesion Molecule–1 Expression in Cutaneous Malignant Melanoma Lesions", *Cancer Res.* 57:1554–1560.

Neff et al. (1998), "Foot–and–Mouth Disease Virus Virulent for Cattle Utilizes the Integrin $\alpha_v\beta_3$ as Its Receptor", *J. Virol.* 72(5):3587–3594.

Nip et al. (1995), "The role of the integrin vitronectin receptor, $\alpha_v\beta_3$ in melanoma metastasis", *Cancer and Metastasis Rev.* 14:241–252.

Niu et al. (1998), "Integrin–Mediated Signalling of Gelatinase B Secretion in Colon Cancer Cells", *Biochem. Biophys. Res. Commun.* 249:287–291.

Novák et al. (1999), "A Convenient Route to Cyanoguanidines", *Synth. Commun.* 29(10):1757–1766.

Panetti et al.(1993), "The $\alpha_v\beta_5$ Integrin Receptor Regulates Receptor–mediated Endocytosis of Vitronectin", *J . Biol. Chem.* 268(16):11492–11495.

Passaniti et al. (1992), "Methods in Laboratory Investigation. A Simple, Quantitative Method for the Assessing Angiogenesis and Antiangiogenic Agents Using Reconstituted Basement Membrane, Heparin, and Fibroblast Growth Factor", *Lab. Invest.* 67(4):519–528.

Phillips et al. (1988), "The Platelet Membrane Glycoprotein IIb–IIIa Complex", *Blood.* 71(4):831–843.

Pytela et al. (1987), "Arginine–Glycine–Aspartic Acid Adhesion Receptors", *Meth. Enzymol.* 144:475–489.

Raeburn et al. (1992), "Techniques for Drug Delivery to the Airways, and the Assessment of Lung Function in Animal Models", *J. Pharmacol. Toxicol. Methods* 27(3):143–159.

Ramadas et al. (1995), "An Expedient Synthesis of Substituted Guanidines", *Tet. Lett.* 36(16):2841–2844.

Ramadas et al. (1997), "A Short and Concise Synthesis of Guanidines", *Synlett* 9:1053–1054.

Raynal et al. (1996), "Bone Sialoprotein Stimulates in Vitro Bone Resorption", *Endocrinology* 137(6):2347–2354.

Rodan et al. (1997), "Integrin function in osteoclasts", *J. Endocrinology* 154:S47–S56.

Roivainen et al. (1994), "Entry of Coxsackievirus A9 into Host Cells: Specific Interactions with $\alpha_v\beta_3$ Integrin, the Vitronectin Receptor", *Virology* 203:357–365.

Schvartz et al. (1999), "Vitronectin", *Int. J. Biochem. Cell Biol.* 31:539–544.

Schwartz et al. (1992), "Restenosis and the Proportional Neointimal Response to Coronary Artery Injury: Results in a Porcine Model", *J. Am. College of Cardiology* 19(2):267–274.

Smith et al. (1990), "Purification and Functional Characterization of Integrin $\alpha_v\beta_5$", *J. Biol. Chem.* 265(19):11008–11013.

Smith et al. (1994), "Oxygen–Induced Retinopathy in the Mouse", *Invest. Ophthal. & Vis. Sci.* 35(1):101–111.

Still et al. (1983), "Direct Synthesis of Z–Unsaturated Esters. A Useful Modification of the Horner–Emmons Olefination", *Tet. Lett.* 24(41):4405–4408.

Summerford et al. (1999), "αVβ5 integrin: a co–receptor for adeno–associated virus type 2 infection", *Nature Medicine* 5(1):78–82.

Svensson et al. (1988), "The Design and Bioactivation of Presystemically Stable Prodrugs", *Drug Metabolism Reviews* 19(2):165–194.

Utsumi et al. (1999), "Urinary excretion of the vitronectin receptor (integrin $\alpha_v\beta_3$) in patients with Fabry disease", *Clin. Chim. Acta* 279:55–68.

Wickham et al. (1994), "Integrin αvβ5 Selectively Promotes Adenovirus Mediated Cell Membrane Permeabilization", *J. Cell Biol.* 127(1):257–264.

\* cited by examiner

INTEGRIN INHIBITORS AND THEIR METHODS OF USE

This application claims the benefit under Title 35, United States Code, §199(e) of U.S. provisional application Ser. No. 60/170,824, filed Dec. 14, 1999, which is hereby incorporated by reference its entirety.

BACKGROUND OF THE INVENTION

The present invention comprises a new class of compounds useful in treating diseases, such as diseases, conditions or disorders mediated by integrin receptors, such as vitronectin and fibronectin receptors. In particular, the compounds of the invention and pharmaceutical compositions thereof are useful for the prophylaxis and treatment of diseases, conditions or disorders involving atherosclerosis, restenosis, inflammation, cancer, osteoporosis and the like. This invention also relates to intermediates and processes useful in the preparation of such compounds.

Integrins are heteromeric cell surface receptors many of which have extracellular domains that bind to an Arg-Gly-Asp tripeptide (RDG) found in extracellular (plasma and matrix) proteins, such as fibronectin, vitronectin, fibrinogen and osteopontin. The fibrinogen receptor, gpIIb/IIIa integrin, is a platelet surface receptor that is thought to mediate platelet aggregation and the formation of hemostatic clot at bleeding wound sites (Blood. 71:831, 1988).

Vitronectin receptors, $\alpha_v\beta_3$ and $\alpha_v\beta_5$ integrin, are expressed by a number of cells, such as endothelial, smooth muscle, osteoclast, bone resorbing, tumor and epithelial cells. Integrin $\alpha_v\beta_3$ has been reported to be involved in bone resorption (Endocrinology 137:2347–54, 1996; J. Endocrinol. 154(Suppl.):S47–S56, 1997), in cell attachment, spreading and migration (Int. J. Biochem. Cell Biol. 31:539–544, 1999; Carreitas et al., Int. J. Cancer 80:285–294, 1999), in signal transduction, cell to cell interactions and is upregulated in response to vascular damage (Int. J. Biochem. Cell Biol. 29:721–725, 1997), in tumor cell invasion, angiogenesis, wound healing, phagocytosis of apoptotic cells and inflammation (J. Cell Biol. 144:767–775, 1999; Drug News Perspect. 10:456–461, 1997; Am. J. Pathol. 148:1407–1421, 1996), in tumor growth and hypercalcemia of malignancy (Cancer Res. 58:1930–1935, 1998), in tumorigenicity of human melanoma cells (Natali et al., Cancer Res. 57:1554–60, 1997), in melanoma metastasis (Cancer Metastasis Rev. 14:241–245, 1995; Cancer Metastasis Rev. 10:3–10, 1991), in the chondrocyte synthesis of matrix metalloproteinases (such as stromelysin, collagenase and gelatinase) which are involved in diseases such as rheumatoid arthritis and osteoarthritis (Arthritis Rheum. 38:1304–1314, 1995), in the progression of the renal injury in Fabry disease (Clin. Chim. Acta 279:55–68, 1999), and in viral infections (J. Virol. 72:3587–3594, 1998; Virology 203:357–65, 1994). Keenan et al. (J. Med. Chem. 40:2289–92, 1997) disclose examples of $\alpha_v\beta_3$ inhibitors which are selective for $\alpha_v\beta_3$ over platelet fibrinogen receptor ($\alpha_{IIb}\beta_3$).

Integrin $\alpha_v\beta_5$ (Smith et al., J. Biol. Chem. 265:11008–13, 1990) is thought to be involved in endocytosis and degredation of vitronectin (J. Biol. Chem. 268:11492–5, 1993), cellular locomotion of human keratinocytes (J. Biol. Chem. 269:26926–32, 1994), tumor cell metastasis (J. Clin. Invest. 99:1390–1398, 1997), differentiation of neuroblastoma metastasis (Am. J. Pathol. 150:1631–1646, 1997), and viral infections (Nat. Med. (N.Y.) 5:78–82, 1999; J. Cell Biol. 127:257–64, 1994).

Integrin $\alpha_v\beta_6$ is an RGD, tenascin and fibronectin binding protein (J. Biol. Chem. 267:5790–6, 1992) which is expressed by a number of cells, such as carcinoma and epithelial cells, and is thought to be involved in carcinoma cell proliferation (J. Cell Biol. 127:547–56, 1994), in wound healing and cell attachment (J. Invest. Dermatol. 106:42–8, 1996), in epithelial inflammation, such as asthma (J. Cell Biol. 133:921–928, 1996), in inducing gelatinase B secretion, activation of the protein kinase-C pathway, tumor cell spreading and proliferation in colon cancer cells (Biochem. Biophys. Res. Commun. 249:287–291, 1998; Int. J. Cancer 81:90–97, 1999), in regulation of pulmonary inflammation and fibrosis and binding and activating transforming growth factor β1 (Munger et al., Cell (Cambridge, Mass) 96:319–328, 1999), and in viral infections (Virology 239:71–77, 1997).

Antagonists of vitronectin receptors $\alpha_v\beta_3$, $\alpha_v\beta_5$ and/or $\alpha_v\beta_6$ have been reported to be useful in the treatment and prevention of atherosclerosis, restenosis, inflammation, wound healing, cancer (e.g., tumor regression by inducing apoptosis), metastasis, bone resorption related diseases (e.g., osteoporosis), diabetic retinopathy, macular degeneration, angiogenesis and viral disease.

Integrins have been associated with angiogenesis. Inhibitors of $\alpha_5\beta_1$ integrin binding to its ligand in tissues have been reported to be useful in the treatment of angiogenesis (WO 99/58139).

WO 99/30709 and WO 99/30713 disclose compounds of the general formula W—X—Y—Z—CR⁵R⁶—CR⁷R⁸—CO₂R⁹, wherein W, X, Y, Z, R⁵, R⁶, R⁷, R⁸ and R⁹ are as defined therein, as antagonists of integrin receptors $\alpha_v\beta_3$, $\alpha_v\beta_5$ and/or $\alpha_v\beta_6$.

WO 99/31099 discloses compounds, such as substituted 2-oxo-imidazolidin-1-yl-alkylcarboxylic acid and substituted 2-thiooxo-imidazolidin-1-yl-alkylcarboxylic acid compounds, as antagonists of integrin receptors $\alpha_v\beta_3$, $\alpha_v\beta_5$ and/or $\alpha_v\beta_6$.

WO 98/18461 discloses compounds of the general formula X—Y—Z-Ring-A—B, wherein X, Y, Z, Ring, A and B are as defined therein, as antagonists of integrin receptors $\alpha_v\beta_3$ and/or $\alpha_v\beta_5$.

U.S. Pat. No. 5,952,341 discloses compounds of the general formula X—Y—Z—C(O)—CH₂—C(O)—NH—CR⁶R⁷—CR⁸R⁹—CO₂R¹⁰, wherein X, Y, Z, R⁶, R⁷, R⁸, R⁹ and R¹⁰ are as defined therein, as antagonists of integrin receptors $\alpha_v\beta_3$ and/or $\alpha_v\beta_5$.

WO 97/08145 discloses compounds of the general formula

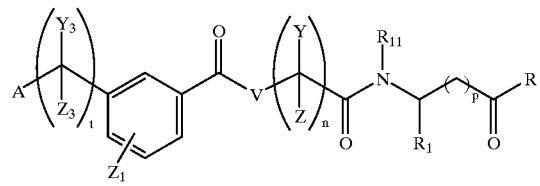

wherein n, p, t, A, R, R₁, R₁₁, V, Y, Y₃, Z, Z₁ and Z₃ are as defined therein, as integrin receptor inhibitors, in particular vitronectin ($\alpha_v\beta_3$) receptor inhibitors.

U.S. Pat. No. 5,843,906 discloses compounds of the general formula

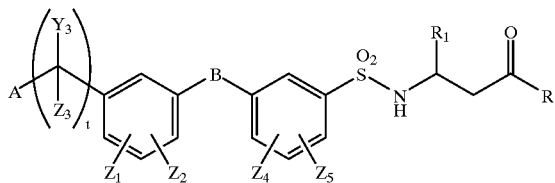

wherein t, A, B, R, R$_1$, Y$_3$, Z$_1$, Z$_2$, Z$_3$, Z$_4$ and Z$_5$ are as defined therein, as integrin receptor inhibitors, in particular vitronectin ($\alpha_v\beta_3$) receptor inhibitors.

WO 97/36862 discloses compounds of the general formula

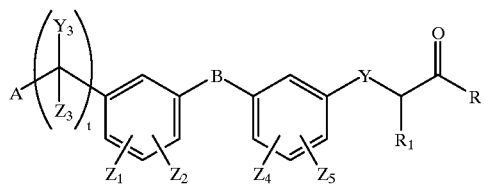

wherein t, A, B, R, R$_1$, Y, Y$_3$, Z$_1$, Z$_2$, Z$_3$, Z$_4$ and Z$_5$ are as defined therein, as integrin receptor inhibitors, in particular vitronectin ($\alpha_v\beta_3$) receptor inhibitors.

WO 99/33798 discloses compounds of the general formula

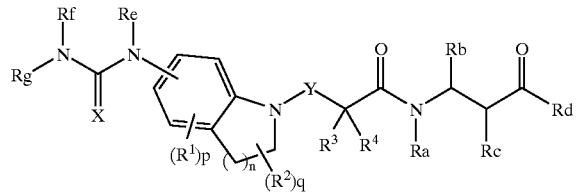

wherein n, p, q, X, Y, R$^1$, R$^2$, R$^3$, R$^4$, Ra, Rb, Rc, Rd, Re, Rf and Rg are as defined therein, as vitronectin ($\alpha_v\beta_3$) receptor inhibitors.

WO 99/37621 discloses compounds of the general formula

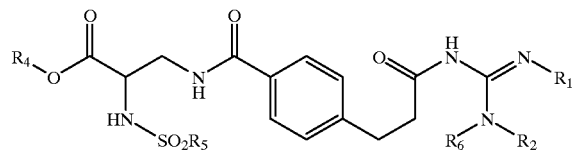

wherein R$_1$, R$_2$, R$_4$, R$_5$ and R$_6$ are as defined therein, as inhibitors of bone resorption, cell adhesion and other diseases and disorders.

WO 99/32457 discloses compounds of the general formula

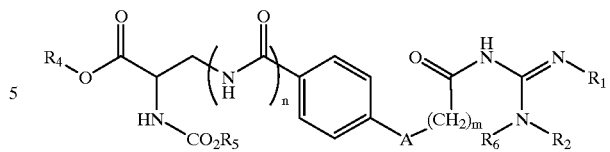

wherein m, n, A, R$_1$, R$_2$, R$_4$, R$_5$ and R$_6$ are as defined therein, as inhibitors of bone resorption, cell adhesion and other diseases and disorders.

U.S. Pat. No. 5,952,306 discloses compounds of the general formula X—(CH$_2$)$_m$—Y—(CH$_2$)$_n$—C(O)—N(R$^3$)—CH$_2$—C(O)—NH—CHR$^4$—CHR$^5$—CO$_2$R$^6$$_1$ wherein m, n, X, Y, R$^3$, R$^4$, R$^5$ and R$^6$ are as defined therein, as antagonists of GPII$_b$III$_a$ fibrinogen receptor.

U.S. Pat. No. 5,849,736 discloses compounds of the general formula

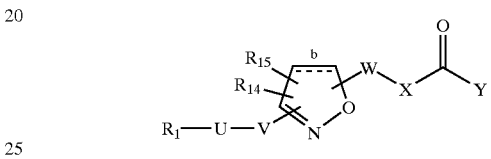

wherein b, U, V, W, X, Y, R$_1$, R$_{14}$ and R$_{15}$ are as defined therein, as antagonists of GPII$_b$III$_a$ fibrinogen receptor.

All of the above references cited herein are incorporated herein by reference in their entirety.

SUMMARY OF THE INVENTION

The present invention comprises a new class of compounds useful in the prophylaxis and treatment of diseases, such as integrin receptors mediated diseases. In particular, the compounds of the invention are useful for the prophylaxis and treatment of diseases or conditions mediated by integrin receptors, such as $\alpha_v\beta_3$, $\alpha_v\beta_5$, $\alpha_v\beta_6$, $\alpha_5\beta_1$ and the like. Accordingly, the invention also comprises pharmaceutical compositions comprising the compounds, methods for the prophylaxis and treatment of integrin receptors mediated diseases, such as cancer, tumor growth, metastasis, diabetic retinopathy, macular degeneration, angiogenesis, restenosis, bone resorption, atherosclerosis, inflammation, viral infection, wound healing and the like, using the compounds and compositions of the invention, and intermediates and processes useful for the preparation of the compounds of the invention.

The compounds of the invention are represented by the following general structure:

wherein A, B, U, V, Alk, g, h and j are defined below.

The foregoing merely summarizes certain aspects of the invention and is not intended, nor should it be construed, as limiting the invention in any way. All patents, patent applications and other publications recited herein are hereby incorporated by reference in their entirety.

DETAILED DESCRIPTION OF THE INVENTION

The present invention provides novel compounds which are useful for treating diseases and disorders involving cancer, tumor growth, metastasis, diabetic retinopathy, macular degeneration, angiogenesis, restenosis, bone resorption, atherosclerosis, inflammation, viral disease, wound healing and the like, as well as other diseases and disorders associated with the same pathways effecting the noted diseases and disorders, especially those modulated by integrin receptors and related pathways, such as the integrin (vitronectin) receptors $\alpha_v\beta_3$, $\alpha_v\beta_5$, $\alpha_v\beta_6$, $\alpha_5\beta_1$ and the like. Such treatment for the disease states also includes prophylactic treatment. The compounds of the present invention are also useful for the prepartion of medicaments which are useful for treating such diseases and disorders.

In accordance with the present invention, there is provided compounds of the formula:

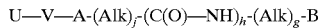

or a pharmaceutically acceptable salt, prodrug, ester or solvate thereof, wherein g, h and j are each independently 0 or 1; provided when h is 0, then g is 0;

each Alk is independently an alkyl radical; preferably, each Alk is independently a $C_1$–$C_{12}$ alkyl radical; more preferably, each Alk is independently a $C_1$–$C_8$ alkyl radical; more preferably, more preferably, each Alk is independently a $C_1$–$C_6$ alkyl radical; more preferably, each Alk is independently a $C_1$–$C_4$ alkyl radical; most preferably, each Alk is independently a $C_1$–$C_2$ alkyl radical;

U represents amidino, guanidino, —(G-alkyl)$_k$—NH—R$_1$, —(G-alkyl)$_k$—NH—C(Q)—R$_1$, —(G-alkyl)$_k$—C(Q)—N(R)—R$_1$, —(G-alkyl)$_k$—NH—C(Q)—N(R)—R$_1$, —(G-alkyl)$_k$—NH—C(Q)—O—R$_1$ or —(G-alkyl)$_k$—O—C(Q)—N(R)—R$_1$ radical; or U represents a hydroxyalkyl-G— radical which is optionally substituted by a cycloalkyl, aryl, heteroaryl or heterocyclyl, wherein the cycloalkyl, aryl, heteroaryl and heterocyclyl radicals are optionally substituted by 1–3 radicals of R$_2$; and preferably, U represents amidino, guanidino, —(G—(C$_1$–C$_8$ alkyl))$_k$—NH—R$_1$, —(G—(C$_1$–C$_8$ alkyl))$_k$—NH—C(Q)—R$_1$, —(G—(C$_1$–C$_8$ alkyl))$_k$—C(Q)—N(R)—R$_1$, —(G—(C$_1$–C$_8$ alkyl))$_k$—NH—C(Q)—N(R)—R$_1$, —(G—(C$_1$–C$_8$ alkyl))$_k$—NH—C(Q)—O—R$_1$ or —(G—(C$_1$–C$_8$ alkyl))$_k$—O—C(Q)—N(R)—R$_1$ radical; or U represents a hydroxy(C$_1$–C$_{12}$ alkyl)-G— radical which is optionally substituted by a C$_3$–C$_8$ cycloalkyl, aryl, heteroaryl of 5–10 ring members or heterocyclyl of 5–8 ring members, wherein the cycloalkyl, aryl, heteroaryl and heterocyclyl radicals are optionally substituted by 1–3 radicals of R$_2$;

more preferably, U represents amidino, guanidino, —(G—(C$_1$–C$_8$ alkyl))$_k$—NH—R$_1$, —(G—(C$_1$–C$_8$ alkyl))$_k$—NH—C(Q)—R$_1$, —(G—(C$_1$–C$_8$ alkyl))$_k$—C(Q)—N(R)—R$_1$, —(G—(C$_1$–C$_8$ alkyl))$_k$—NH—C(Q)—N(R)—R$_1$ or —(G—(C$_1$–C$_8$ alkyl))$_k$—NH—C(Q)—O—R$_1$ radical;

more preferably, U represents amidino, guanidino, —(G—(C$_1$–C$_8$ alkyl))$_k$—NH—R$_1$,—NH—C(Q)—R$_1$, —(G—(C$_1$–C$_8$ alkyl))$_k$—C(Q)—N(R)—R$_1$,—NH—C(Q)—N(R)—R$_1$ or —NH—C(Q)—O—R$_1$ radical;

wherein k is 0 or 1;

G represents a bond, O, S or NH; preferably, G represents a bond, O or NH ; more preferably, G represents a bond or NH;

Q represents O, S, NH, N—CN or N-alkyl; preferably, Q represents O, S, NH, N—CN or N—(C$_1$–C$_8$ alkyl); more preferably, Q represents O, S, NH, N—CN or N—(C$_1$–C$_4$ alkyl); most preferably, Q represents O or NH;

R is a radical of hydrogen or alkyl; preferably, R is a radical of hydrogen or C$_1$–C$_8$ alkyl; more preferable, R is a radical of hydrogen or C$_1$–C$_4$ alkyl; more preferably, R is a radical of hydrogen or C$_1$–C$_2$ alkyl; and most preferably, R is a radical of hydrogen;

R$_1$ is a radical of alkyl, haloalkyl, R$_{21}$,R$_{22}$N-alkyl, R$_{21}$O-alkyl, R$_{21}$S-alkyl, cycloalkyl, cycloalkyl-alkyl, aryl, aryl-alkyl, heteroaryl, heteroaryl-alkyl, heterocyclyl or heterocyclyl-alkyl, wherein the cycloalkyl, aryl, heteroaryl and heterocyclyl radicals are optionally substituted by 1–3 radicals of R$_2$; and preferably, R$_1$ is a radical of C$_1$–C$_8$ alkyl, halo(C$_1$–C$_8$ alkyl) of 1–7 halo radicals, R$_{21}$R$_{22}$N—(C$_1$–C$_8$ alkyl), R$_{21}$O—(C$_1$–C$_8$ alkyl), R$_{21}$S—(C$_1$–C$_8$ alkyl), C$_3$–C$_8$ cycloalkyl, C$_3$–C$_8$ cycloalkyl(C$_1$–C$_8$ alkyl), aryl, aryl(C$_1$–C$_8$ alkyl), heteroaryl of 5–10 ring members, heteroaryl(C$_1$–C$_8$ alkyl) of 5–10 ring members, heterocyclyl of 5–8 ring members or heterocyclyl(C$_1$–C$_8$ alkyl) of 5–8 ring members, wherein the cycloalkyl, aryl, heteroaryl and heterocyclyl radicals are optionally substituted by 1–3 radicals of R$_2$;

more preferably, R$_1$ is a radical of C$_1$–C$_6$ alkyl, halo (C$_1$–C$_6$ alkyl) of 1–5 halo radicals, R$_{21}$R$_{22}$N—(C$_1$–C$_6$ alkyl), R$_{21}$O—(C$_1$–C$_6$ alkyl), C$_3$–C$_8$ cycloalkyl, C$_3$–C$_8$ cycloalkyl(C$_1$–C$_6$ alkyl), aryl, aryl(C$_1$–C$_6$ alkyl), heteroaryl of 5–10 ring members, heteroaryl(C$_1$–C$_6$ alkyl) of 5–10 ring members, heterocyclyl of 5–8 ring members or heterocyclyl(C$_1$–C$_6$ alkyl) of 5–8 ring members, wherein the cycloalkyl, aryl, heteroaryl and heterocyclyl radicals are optionally substituted by 1–3 radicals of R$_2$;

more preferably, R$_1$ is a radical of C$_1$–C$_6$ alkyl, halo (C$_1$–C$_6$ alkyl) of 1–5 halo radicals, R$_{21}$R$_{22}$N—(C$_1$–C$_4$ alkyl), R$_{21}$O—(C$_1$–C$_4$ alkyl), C$_3$–C$_8$ cycloalkyl, C$_3$–C$_8$ cycloalkyl(C$_1$–C$_4$ alkyl), aryl, aryl(C$_1$–C$_4$ alkyl), heteroaryl of 5–10 ring members, heteroaryl(C$_1$–C$_4$ alkyl) of 5–10 ring members, heterocyclyl of 5–8 ring members or heterocyclyl(C$_1$–C$_4$ alkyl) of 5–8 ring members, wherein the cycloalkyl, aryl, heteroaryl and heterocyclyl radicals are optionally substituted by 1–3 radicals of R$_2$;

wherein R$_{21}$ and R$_{22}$ are each independently a radical of hydrogen, alkyl, haloalkyl, cycloalkyl, cycloalkyl-alkyl, aryl, aryl-alkyl, heteroaryl, heteroaryl-alkyl, heterocyclyl or heterocyclyl-alkyl, wherein the cycloalkyl, aryl, heteroaryl and heterocyclyl radicals are optionally substituted by 1–3 radicals of R$_2$; and preferably, R$_{21}$ and R$_{22}$ are each independently a radical of hydrogen, C$_1$–C$_8$ alkyl, halo(C$_1$–C$_8$ alkyl) of 1–7 halo radicals, C$_3$–C$_8$ cycloalkyl, C$_3$–C$_8$ cycloalkyl (C$_1$–C$_8$ alkyl), aryl, aryl(C$_1$–C$_8$ alkyl), heteroaryl of 5–10 ring members, heteroaryl(C$_1$–C$_8$ alkyl) of 5–10 ring members, heterocyclyl of 5–8 ring members or heterocyclyl(C$_1$–C$_8$ alkyl) of 5–8 ring members, wherein the cycloalkyl, aryl, heteroaryl and heterocyclyl radicals are optionally substituted by 1–3 radicals of R$_2$;

more preferably, R$_{21}$ and R$_{22}$ are each independently a radical of hydrogen, C$_1$–C$_8$ alkyl, aryl, aryl(C$_1$–C$_4$ alkyl), heteroaryl of 5–10 ring members or heteroaryl (C$_1$–C$_4$ alkyl) of 5–10 ring members, wherein the aryl and heteroaryl radicals are optionally substituted by 1–3 radicals of R$_2$;

more preferably, R$_{21}$ and R$_{22}$ are each independently a radical of hydrogen, C$_1$–C$_6$ alkyl, aryl or heteroaryl of 5–10 ring members, wherein the aryl and heteroaryl radicals are optionally substituted by 1–3 radicals of R$_2$;

more preferably, $R_{21}$ and $R_{22}$ are each independently a radical of hydrogen, $C_1$–$C_6$ alkyl or aryl, wherein the aryl and heteroaryl radicals are optionally substituted by 1–3 radicals of $R_2$; each $R_2$ is independently a halo, alkyl, alkoxy, alkylthio, haloalkyl, haloalkoxy, hydroxy, carboxy, cyano, azido, amidino, guanidino, nitro, amino, alkylamino or dialkylamino radical or two adjacent $R_2$ radicals on an aryl or heteroaryl radical represent a methylenedioxy, ethylenedioxy or propylenedioxy radical; and preferably, each $R_2$ is independently a halo, $C_1$–$C_6$ alkyl, $C_1$–$C_6$ alkoxy, $C_1$–$C_6$ alkylthio, halo($C_1$–$C_4$ alkyl) of 1–5 halo radicals, halo($C_1$–$C_4$ alkoxy) of 1–5 halo radicals, hydroxy, carboxy, cyano, azido, amidino, guanidino, nitro, amino, $C_1$–$C_8$ alkylamino or di($C_1$–$C_8$ alkyl)amino radical or two adjacent $R_2$ radicals on an aryl or heteroaryl radical represent a methylenedioxy, ethylenedioxy or propylenedioxy radical;

more preferably, each $R_2$ is independently a halo, $C_1$–$C_4$ alkyl, $C_1$–$C_4$ alkoxy, $C_1$–$C_4$ alkylthio, halo($C_1$–$C_2$ alkyl) of 1–5 halo radicals, halo($C_1$–$C_2$ alkoxy) of 1–5 halo radicals, hydroxy, carboxy, cyano, azido, amidino, guanidino, nitro, amino, $C_1$–$C_4$ alkylamino or di($C_1$–$C_4$ alkyl)amino radical or two adjacent $R_2$ radicals on an aryl or heteroaryl radical represent a methylenedioxy, ethylenedioxy or propylenedioxy radical;

more preferably, each $R_2$ is independently a halo, $C_1$–$C_2$ alkyl, $C_1$–$C_2$ alkoxy, $C_1$–$C_2$ alkylthio, $CF_3$—, $CF_3O$—, hydroxy, carboxy, cyano, azido, amidino, guanidino, nitro, amino, $C_1$–$C_2$ alkylamino or di($C_1$–$C_2$ alkyl) amino radical or two adjacent $R_2$ radicals on an aryl or heteroaryl radical represent a methylenedioxy, ethylenedioxy or propylenedioxy radical;

V represents a radical of formula

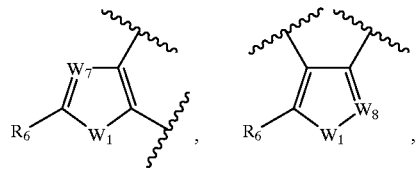

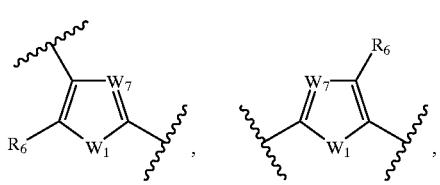

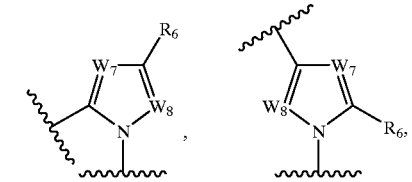

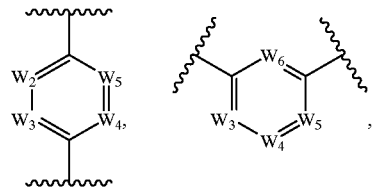

-continued

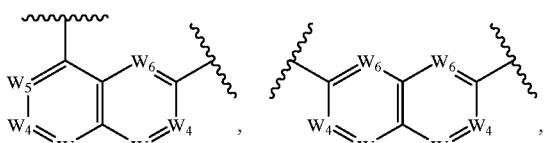

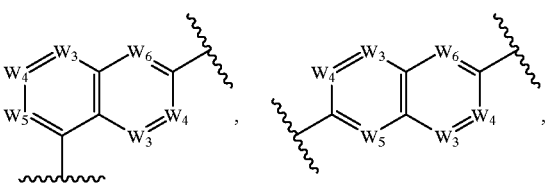

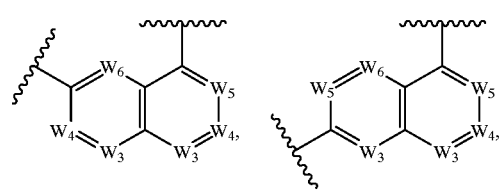

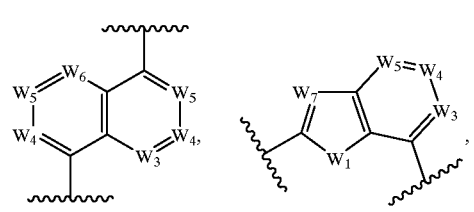

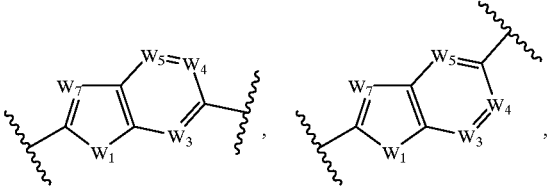

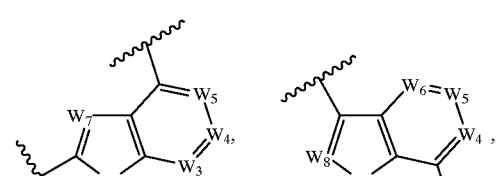

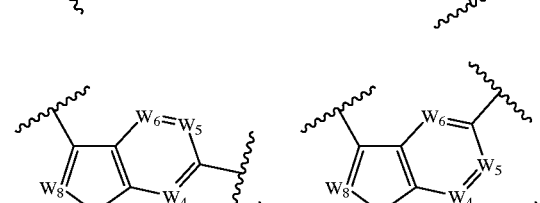

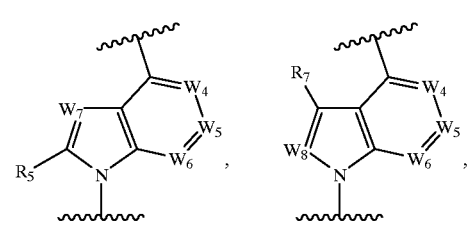

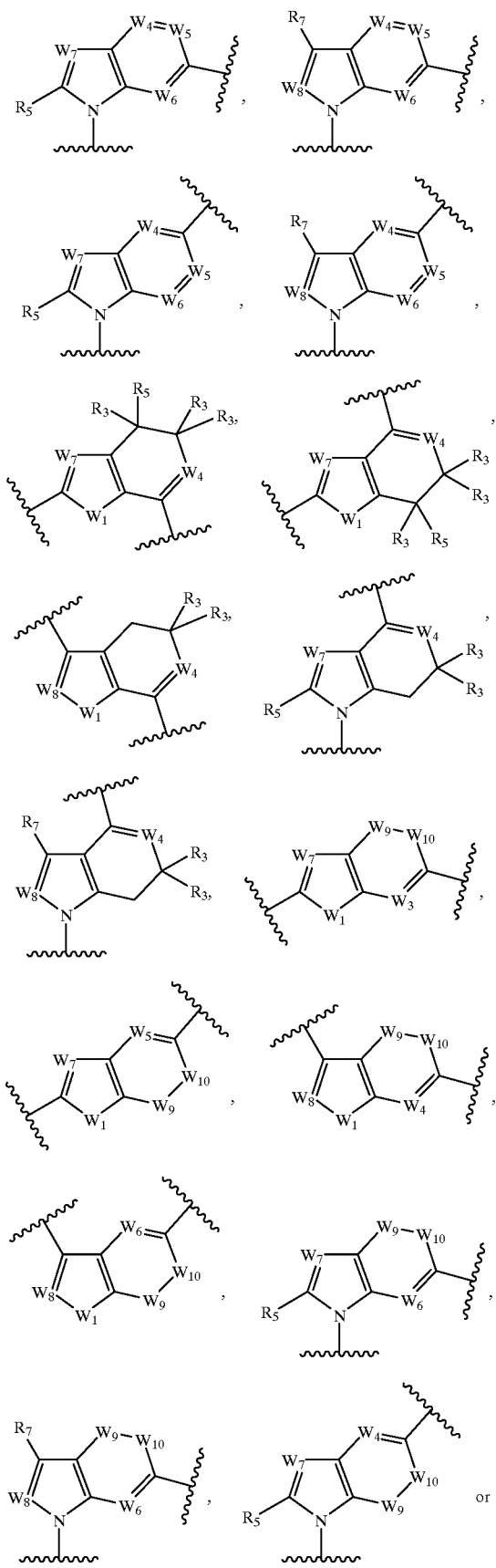

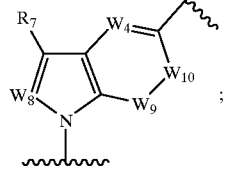

preferably, V represents a radical of formula

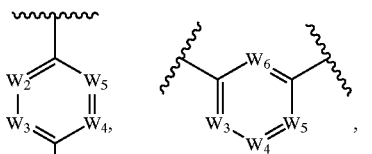

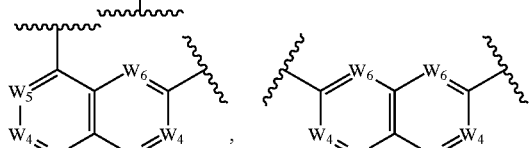

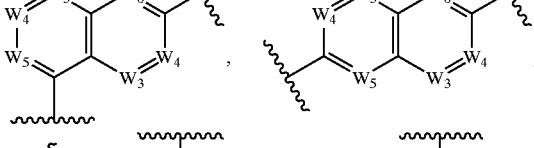

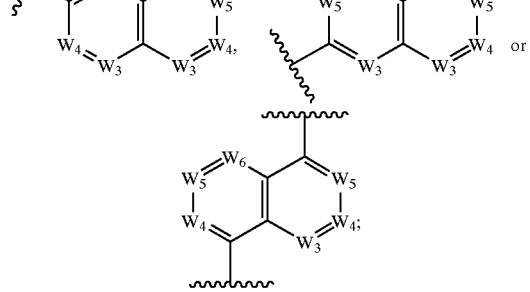

more preferably, V represents a radical of formula

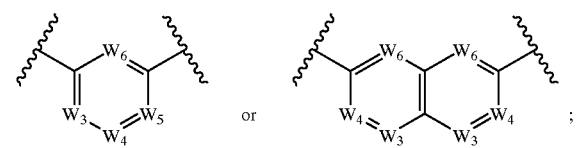

wherein $W_1$ is O, S or N—$R_3$;
  wherein each $R_3$ is independently a hydrogen or alkyl radical; preferably, each $R_3$ is independently a hydrogen or $C_1$–$C_6$ alkyl radical;
  $W_7$ is N or C—$R_7$; preferably, $W_7$ is C—$R_7$;
  $W_8$ is N or C—$R_5$; preferably, $W_8$ is C—$R_5$;
  $W_9$ is $C(R_3)_2$ and $W_{10}$ is $W_1$; or $W_9$ is $CR_3R_5$ and $W_{10}$ is $C(R_3)_2$;
  each $W_2$, $W_3$, $W_4$ and $W_5$ are independently N or C—$R_4$; preferably, each $W_2$, $W_3$, $W_4$ and $W_5$ are independently C—$R_4$; provided the total number of cycloalkyl, aryl, heteroaryl, heterocyclyl, carboxy, —C(O)—O—$R_{19}$, —C(O)—$R_{19}$, —C(O)—NH—$R_{19}$, —C(O)—N($R_{19}$)$_2$ and —$R_{19}$ radicals in $W_2$, $W_3$, $W_4$ and $W_5$ is 0–2;

each $W_6$ is independently N or C—H; preferably, each $W_6$ is C—H; provided that not more than two of $W_2$, $W_3$, $W_4$, $W_5$ and $W_6$ represent N; and each $R_4$ is independently a hydrogen, halo, alkyl, alkoxy, alkylthio, haloalkyl, haloalkoxy, hydroxy, cyano, carboxy, —C(O)—O—$R_{19}$, —C(O)—$R_{19}$, —C(O)—NH—$R_{19}$, —C(O)—N($R_{19}$)$_2$, cycloalkyl, cycloalkyl-alkyl, aryl, aryl-alkyl, heteroaryl, heteroaryl-alkyl, heterocyclyl or heterocyclyl-alkyl radical, wherein the cycloalkyl, aryl, heteroaryl and heterocyclyl radicals are optionally substituted by 1–3 radicals of $R_2$; or two adjacent $R_4$ radicals taken together with the carbon atoms to which they are attached represent a fused-phenyl or fused-heteroaryl of 5–6 ring members, wherein the phenyl and heteroaryl radicals are optionally substituted by 1–3 radicals of $R_2$;

preferably, each $R_4$ is independently a hydrogen, halo, $C_1$–$C_6$ alkyl, $C_1$–$C_6$ alkoxy, $C_1$–$C_6$ alkylthio, halo($C_1$–$C_4$ alkyl) of 1–5 halo radicals, halo($C_1$–$C_4$ alkoxy) of 1–5 halo radicals, hydroxy, cyano, carboxy, —C(O)—O—$R_{19}$, —C(O)—$R_{19}$, —C(O)—NH—$R_{19}$, —C(O)—N($R_{19}$)$_2$, $C_3$–$C_6$ cycloalkyl, $C_3$–$C_6$ cycloalkyl($C_1$–$C_4$ alkyl), aryl, aryl($C_1$–$C_4$ alkyl), heteroaryl of 5–10 ring members, heteroaryl($C_1$–$C_4$ alkyl) of 5–10 ring members, heterocyclyl of 5–8 ring members or heterocyclyl($C_1$–$C_4$ alkyl) of 5–8 ring members radical, wherein the cycloalkyl, aryl, heteroaryl and heterocyclyl radicals are optionally substituted by 1–3 radicals of $R_2$; or two adjacent $R_4$ radicals taken together with the carbon atoms to which they are attached represent a fused-phenyl or fused-heteroaryl of 5–6 ring members, wherein the phenyl and heteroaryl radicals are optionally substituted by 1–3 radicals of $R_2$;

more preferably, each $R_4$ is independently a hydrogen, halo, $C_1$–$C_4$ alkyl, $C_1$–$C_4$ alkoxy, $C_1$–$C_4$ alkylthio, halo($C_1$–$C_2$ alkyl) of 1–5 halo radicals, halo($C_1$–$C_2$ alkoxy) of 1–5 halo radicals, hydroxy, cyano, carboxy, —C(O)—O—$R_{19}$, —C(O)—$R_{19}$, —C(O)—NH—$R_{19}$, —C(O)—N($R_{19}$)$_2$, $C_3$–$C_6$ cycloalkyl, $C_3$–$C_6$ cycloalkyl($C_1$–$C_4$ alkyl), aryl, aryl($C_1$–$C_4$ alkyl), heteroaryl of 5–10 ring members, heteroaryl($C_1$–$C_4$ alkyl) of 5–10 ring members, heterocyclyl of 5–8 ring members or heterocyclyl($C_1$–$C_4$ alkyl) of 5–8 ring members radical, wherein the cycloalkyl, aryl, heteroaryl and heterocyclyl radicals are optionally substituted by 1–3 radicals of $R_2$;

more preferably, each $R_4$ is independently a hydrogen, halo, $C_1$–$C_4$ alkyl, $C_1$–$C_4$ alkoxy, $C_1$–$C_4$ alkylthio, halo($C_1$–$C_2$ alkyl) of 1–5 halo radicals, halo($C_1$–$C_2$ alkoxy) of 1–5 halo radicals, hydroxy or cyano radical;

more preferably, each $R_4$ is independently a hydrogen, halo, $C_1$–$C_2$ alkyl, $C_1$–$C_2$ alkoxy, $C_1$–$C_2$ alkylthio, $CF_3$—, $CF_3O$—, hydroxy or cyano radical; $R_5$, $R_6$ and $R_7$ are each independently a hydrogen, halo, alkyl, alkoxy, alkylthio, haloalkyl, haloalkoxy, hydroxy or cyano radical; or $R_5$ and $R_6$ or $R_6$ and $R_7$ taken together with the carbon atoms to which they are attached represent a fused-phenyl or fused-heteroaryl of 6 ring members, wherein the phenyl and heteroaryl radicals are optionally substituted by 1–3 radicals of $R_2$; or $R_3$ and $R_6$ taken together with the carbon atoms to which they are attached represent a fused-heteroaryl of 6 ring members optionally substituted by 1–3 radicals of $R_2$;

preferably, $R_5$, $R_6$ and $R_7$ are each independently a hydrogen, halo, $C_1$–$C_6$ alkyl, $C_1$–$C_6$ alkoxy, $C_1$–$C_6$ alkylthio, halo($C_1$–$C_4$ alkyl) of 1–5 halo radicals, halo ($C_1$–$C_4$ alkoxy) of 1–5 halo radicals, hydroxy or cyano radical; or $R_5$ and $R_6$ or $R_6$ and $R_7$ taken together with the carbon atoms to which they are attached represent a fused-phenyl or fused-heteroaryl of 6 ring members, wherein the phenyl and heteroaryl radicals are optionally substituted by 1–3 radicals of $R_2$; or $R_3$ and $R_6$ taken together with the carbon atoms to which they are attached represent a fused-heteroaryl of 6 ring members optionally substituted by 1–3 radicals of $R_2$;

more preferably, $R_5$, $R_6$ and $R_7$ are each independently a hydrogen, halo, $C_1$–$C_2$ alkyl, $C_1$–$C_2$ alkoxy, $C_1$–$C_2$ alkylthio, $CF_3$—, $CF_3O$—, hydroxy or cyano radical;

A represents a radical of formula

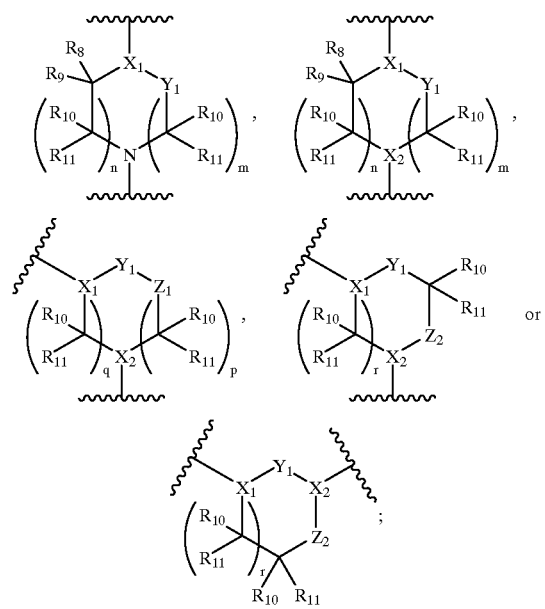

preferably, A represents a radical of formula

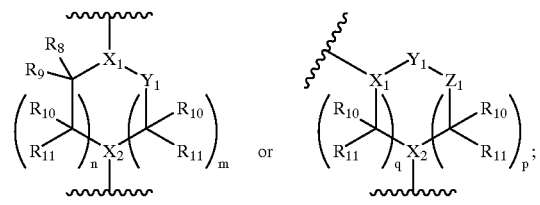

more preferably, A represents a radical of formula

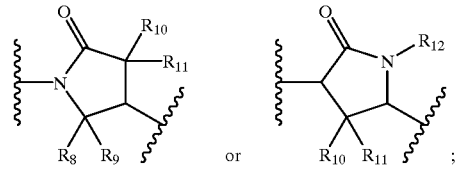

most preferably, A represents a radical of formula

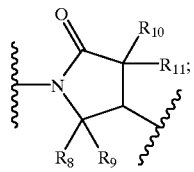

wherein $X_1$ is N or C—H;

$X_2$ is C—H, C-alkyl, a spirocycloalkyl or spiroheterocyclyl radical; wherein the spirocycloalkyl and spiroheterocyclyl radicals are optionally substituted by an oxo or thiooxo radical and 1–2 radicals of alkyl, haloalkyl, hydroxy, alkoxy or haloalkoxy;

preferably, $X_2$ is C—H, C—($C_1$–$C_4$ alkyl), a $C_3$–$C_8$ spirocycloalkyl or spiroheterocyclyl of 5–8 ring members radical; wherein the spirocycloalkyl and spiroheterocyclyl radicals are optionally substituted by an oxo or thiooxo radical and 1–2 radicals of $C_1$–$C_6$ alkyl, halo($C_1$–$C_4$ alkyl) of 1–5 halo radicals, hydroxy, $C_1$–$C_6$ alkoxy or halo($C_1$–$C_4$ alkoxy) of 1–5 halo radicals;

more preferably, $X_2$ is C—H or C-(methyl) radical;

$Y_1$ is —C(O)—, —C(S)—, —S(O)— or —S(O)$_2$—; preferably, $Y_1$ is —C(O)— or —C(S)—; more preferably, $Y_1$ is —C(O)—;

$Z_1$ is O or N—$R_{12}$;

$Z_2$ is O, S or N—$R_{12}$;

n and m are each independently 0, 1 or 2, provided n+m=1, 2, 3 or 4;

p and q are each independently 0, 1 or 2, provided p+q=1, 2 or 3;

r is 1 or 2;

$R_8$, $R_9$, $R_{10}$, $R_{11}$ and $R_{12}$ are each independently a hydrogen or alkyl radical; or —$CR_8R_9$— represents a —C(O)—; preferably, $R_8$, $R_9$, $R_{10}$, $R_{11}$ and $R_{12}$ are each independently a hydrogen or $C_1$–$C_6$ alkyl radical; or —$CR_8R_9$— represents a —C(O)—; more preferably, $R_8$, $R_9$, $R_{10}$, $R_{11}$ and $R_{12}$ are each independently a hydrogen or methyl radical; or —$CR_8R_9$— represents a —C(O)—;

B represents a radical of formula

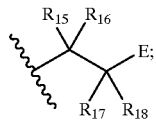

wherein (a) $R_{15}$ is a hydrogen or alkyl radical; and $R_{17}$ is (1) an aryl, heteroaryl, —NH—C(O)—$R_{19}$, —C(O)—NH—$R_{19}$, —NH—C(O)—NH—$R_{19}$, —O—C(O)—NH—$R_{19}$, —NH—C(O)—O—$R_{19}$, —S(O)$_2$—$R_{19}$, —NH—S(O)$_2$—$R_{19}$, —S(O)$_2$—NH—$R_{19}$ or —NH—S(O)$_2$—NH—$R_{19}$ radical, or (2) an alkyl radical substituted by a radical of aryl, heteroaryl, —NH—C(O)—$R_{19}$, —C(O)—NH—$R_{19}$, —NH—C(O)—NH—$R_{19}$, —O—C(O)—NH—$R_{19}$, —NH—C(O)—O—$R_{19}$, —S(O)$_2$—$R_{19}$, —NH—S(O)$_2$—$R_{19}$, —S(O)$_2$—NH—$R_{19}$ or —NH—S(O)$_2$—NH—$R_{19}$; wherein the aryl and heteroaryl radicals are optionally substituted by 1–3 radicals of $R_2$;

preferably, (a) $R_{15}$ is a hydrogen or $C_1$–$C_6$ alkyl radical; and $R_{17}$ is (1) an aryl, heteroaryl of 5–10 ring members, —NH—C(O)—$R_{19}$—, —C(O)—NH—$R_{19}$, —NH—C(O)—NH—$R_{19}$, —O—C(O)—NH—$R_{19}$, —NH—C(O)—O—$R_{19}$, —S(O)$_2$—$R_{19}$, —NH—S(O)$_2$—$R_{19}$, —S(O)$_2$—NH—$R_{19}$ or —NH—S(O)$_2$—NH—$R_{19}$ radical, or (2) an $C_1$–$C_6$ alkyl radical substituted by a radical of aryl, heteroaryl of 5–10 ring members, —NH—C(O)—$R_{19}$, —C(O)—NH—$R_{19}$, —NH—C(O)—NH—$R_{19}$, —O—C(O)—NH—$R_{19}$, —NH—C(O)—O—$R_{19}$, —S(O)$_2$—$R_{19}$, —NH—S(O)$_2$—$R_{19}$, —S(O)$_2$—NH—$R_{19}$ or —NH—S(O)$_2$—NH—$R_{19}$; wherein the aryl and heteroaryl radicals are optionally substituted by 1–3 radicals of $R_2$;

more preferably, (a) $R_{15}$ is a hydrogen or $C_1$–$C_2$ alkyl radical; and $R_{17}$ is —NH—C(O)—$R_{19}$, —NH—C(O)—NH—$R_{19}$, —NH—C(O)—O—$R_{19}$, —NH—S(O)$_2$—$R_{19}$ or —NH—S(O)$_2$—NH—$R_{19}$ radical;

more preferably, (a) $R_{15}$ is a hydrogen or $C_1$–$C_2$ alkyl radical; and $R_{17}$ is —NH—C(O)—O—$R_{19}$ or —NH—S(O)$_2$—$R_{19}$ radical; or (b) $R_{17}$ is a hydrogen or alkyl radical; and $R_{15}$ is (1) an aryl, heteroaryl, cycloalkyl, heterocyclyl, —NH—C(O)—$R_{19}$, —C(O)—NH—$R_{19}$, —NH—C(O)—NH—$R_{19}$, —O—C(O)—NH—$R_{19}$, —NH—C(O)—O—$R_{19}$, —S(O)$_2$—$R_{19}$, —NH—S(O)$_2$—$R_{19}$, —S(O)$_2$—NH—$R_{19}$ or —NH—S(O)$_2$—NH—$R_{19}$ radical, or (2) an alkyl radical substituted by a radical of aryl, heteroaryl, cycloalkyl, heterocyclyl, —NH—C(O)—$R_{19}$, —C(O)—NH—$R_{19}$, —NH—C(O)—NH—$R_{19}$, —O—C(O)—NH—$R_{19}$, —NH—C(O)—O—$R_{19}$, —S(O)$_2$—$R_{19}$, —NH—S(O)$_2$—$R_{19}$, —S(O)$_2$—NH—$R_{19}$ or —NH—S(O)$_2$—NH—$R_{19}$ radical; wherein the cycloalkyl, aryl, heteroaryl and heterocyclyl radicals are optionally substituted by 1–3 radicals of $R_2$;

preferably, (b) $R_{17}$ is a hydrogen or $C_1$–$C_6$ alkyl radical; and $R_{15}$ is (1) an aryl, heteroaryl of 5–10 ring members, $C_3$–$C_8$ cycloalkyl, heterocyclyl of 5–8 ring members, —NH—C(O)—$R_{19}$, —C(O)—NH—$R_{19}$, —NH—C(O)—NH—$R_{19}$, —O—C(O)—NH—$R_{19}$, —NH—C(O)—O—$R_{19}$, —S(O)$_2$—$R_{19}$, —NH—S(O)$_2$—$R_{19}$, —S(O)$_2$—NH—$R_{19}$ or —NH—S(O)$_2$—NH—$R_{19}$ radical, or (2) an $C_1$–$C_4$ alkyl radical substituted by a radical of aryl, heteroaryl of 5–10 ring members, $C_3$–$C_8$ cycloalkyl, heterocyclyl of 5–8 ring members, —NH—C(O)—$R_{19}$, —C(O)—NH—$R_{19}$, —NH—C(O)—NH—$R_{19}$, —O—C(O)—NH—$R_{19}$, —NH—C(O)—O—$R_{19}$, —S(O)$_2$—$R_{19}$, —NH—S(O)$_2$—$R_{19}$, —S(O)$_2$—NH—$R_{19}$ or —NH—S(O)$_2$—NH—$R_{19}$ radical; wherein the cycloalkyl, aryl, heteroaryl and heterocyclyl radicals are optionally substituted by 1–3 radicals of $R_2$;

more preferably, (b) $R_{17}$ is a hydrogen or $C_1$–$C_2$ alkyl radical; and $R_{15}$ is (1) an aryl, heteroaryl of 5–10 ring members, $C_3$–$C_8$ cycloalkyl or heterocyclyl of 5–8 ring members radical, or (2) an $C_1$–$C_2$ alkyl radical substituted by a radical of aryl, heteroaryl of 5–10 ring members, $C_3$–$C_8$ cycloalkyl or heterocyclyl of 5–8 ring members radical; wherein the cycloalkyl, aryl, heteroaryl and heterocyclyl radicals are optionally substituted by 1–3 radicals of $R_2$;

more preferably, (b) $R_{17}$ is a hydrogen or $C_1$–$C_2$ alkyl radical; and $R_{15}$ is (1) an aryl or heteroaryl of 5–10 ring members, or (2) an $C_1$–$C_2$ alkyl radical substituted by a radical of aryl or heteroaryl of 5–10 ring members; wherein the aryl and heteroaryl radicals are optionally substituted by 1–3 radicals of $R_2$;

provided that when a nitrogen atom is attached to the carbon atom to which $R_{15}$ is attached, then $R_{15}$ is (1) an aryl, heteroaryl, cycloalkyl, heterocyclyl or —C(O)—NH—$R_{19}$ radical, or (2) an alkyl radical substituted by a radical of aryl, heteroaryl, cycloalkyl, heterocyclyl, —NH—C(O)—$R_{19}$, —C(O)—NH—$R_{19}$, —NH—C(O)—NH—$R_{19}$, —O—C(O)—NH—$R_{19}$, —NH—C(O)—O—$R_{19}$, —S(O)$_2$—$R_{19}$, —NH—S (O)$_2$—$R_{19}$, —S(O)$_2$—NH—$R_{19}$ or —NH—S(O)$_2$—NH—$R_{19}$; and wherein $R_{19}$ is a alkyl, cycloalkyl, cycloalkyl-alkyl, aryl, aryl-alkyl, heteroaryl, heteroaryl-alkyl, heterocyclyl or heterocyclyl-alkyl, wherein the cycloalkyl, aryl, heteroaryl and heterocyclyl radicals are optionally substituted by 1–3 radicals of $R_2$;

preferably, $R_{19}$ is a $C_1$–$C_6$ alkyl, $C_3$–$C_8$ cycloalkyl, $C_3$–$C_8$ cycloalkyl($C_1$–$C_6$ alkyl), aryl, aryl($C_1$–$C_6$ alkyl), heteroaryl of 5–10 ring members, heteroaryl($C_1$–$C_6$ alkyl) of 5–10 ring members, heterocyclyl of 5–8 ring members or heterocyclyl($C_1$–$C_6$ alkyl) of 5–8 ring members, wherein the cycloalkyl, aryl, heteroaryl and heterocyclyl radicals are optionally substituted by 1–3 radicals of $R_2$;

more preferably, $R_{19}$ is a $C_1$–$C_4$ alkyl, aryl, aryl($C_1$–$C_4$ alkyl), heteroaryl of 5–10 ring members or heteroaryl ($C_1$–$C_4$ alkyl) of 5–10 ring members, wherein the aryl and heteroaryl radicals are optionally substituted by 1–3 radicals of $R_2$;

more preferably, $R_{19}$ is a $C_1$–$C_4$ alkyl, aryl or aryl($C_1$–$C_4$ alkyl), wherein the aryl radicals are optionally substituted by 1–3 radicals of $R_2$;

$R_{16}$ and $R_{18}$ are each independently a hydrogen or alkyl radical; preferably, $R_{16}$ and $R_{18}$ are each independently a hydrogen or $C_1$–$C_6$ alkyl radical; more preferably, $R_{16}$ and $R_{18}$ are each independently a hydrogen or $C_1$–$C_4$ alkyl radical; more preferably, $R_{16}$ and $R_{18}$ are each independently a hydrogen or $C_1$–$C_2$ alkyl radical;

E is a radical of carboxy, amido, tetrazolyl, —C(O)—O—$R_{20}$, —C(O)—NH—$R_{20}$, —C(O)—NH—S(O)—$R_{20}$, —C(O)—NH—S(O)$_2$—$R_{20}$ or —C(O)—NH—C(O)—$R_{20}$; preferably, E is a radical of carboxy, amido, tetrazolyl or —C(O)—O—$R_{20}$; more preferably, E is a radical of carboxy or —C(O)—O—$R_{20}$; most preferably, E is a radical of carboxy;

wherein $R_{20}$ is an alkyl, cycloalkyl, aryl, heteroaryl or heterocyclyl radical or an alkyl radical substituted by 1–3 radicals of halo, hydroxy, carboxy, amino, cycloalkyl, aryl, heteroaryl or heterocyclyl, wherein the cycloalkyl, aryl, heteroaryl and heterocyclyl radicals are optionally substituted by 1–3 radicals of $R_2$; and preferably, $R_{20}$ is a $C_1$–$C_6$ alkyl, $C_3$–$C_8$ cycloalkyl, aryl, heteroaryl of 5–10 ring members or heterocyclyl of 5–8 ring members radical or a $C_1$–$C_6$ alkyl radical substituted by 1–3 radicals of halo, hydroxy, carboxy, amino, $C_3$–$C_8$ cycloalkyl, aryl, heteroaryl of 5–10 ring members or heterocyclyl of 5–8 ring members, wherein the cycloalkyl, aryl, heteroaryl and heterocyclyl radicals are optionally substituted by 1–3 radicals of $R_2$;

more preferably, $R_{20}$ is a $C_1$–$C_4$ alkyl, aryl or heteroaryl of 5–10 ring members or a $C_1$–$C_4$ alkyl radical substituted by 1–3 radicals of halo, hydroxy, carboxy, amino, aryl, heteroaryl of 5–10 ring members or heterocyclyl of 5–8 ring members, wherein the aryl, heteroaryl and heterocyclyl radicals are optionally substituted by 1–3 radicals of $R_2$;

more preferably, $R_{20}$ is a $C_1$–$C_2$ alkyl, aryl or heteroaryl of 5–10 ring members or a $C_1$–$C_2$ alkyl radical substituted by 1–3 radicals of halo, hydroxy, carboxy, aryl or heteroaryl of 5–10 ring members, wherein the aryl and heteroaryl radicals are optionally substituted by 1–3 radicals of $R_2$;

more preferably, $R_{20}$ is a $C_1$–$C_2$ alkyl, aryl or aryl($C_1$–$C_2$ alkyl) radical, wherein the aryl radicals are optionally substituted by 1–3 radicals of $R_2$; and provided that when U represents amidino, guanidino, —C(Q)—N(R)—$R_1$ or —NH—C(Q)—N(R)—$R_1$ radical, wherein Q represents NH, N—CN or N-alkyl, then at least one of g, h or j is 1.

In another aspect of the invention, there is provided a method for the therapeutic or prophylactic treatment of disease states involving tumor growth, metastasis, diabetic retinopathy, macular degeneration, angiogenesis, restenosis, bone resorption, atherosclerosis, inflammation, viral disease, wound healing or the like in a warm-blooded animal which comprises administering to a warm blooded animal in need thereof a therapeutically or prophylactically effective amount of a compound or pharmacutical composition of the invention.

In a further embodiment of the invention, there is provided a method for modulation, preferably inhibition, of one or more integrin receptors which comprises administering to a warm blooded animal in need thereof an effective amount of a compound or pharmacutical composition of the invention.

In a further embodiment of the invention, there is provided a method for modulation, preferably inhibition, of one or more vitronectin receptors which comprises administering to a warm blooded animal in need thereof an effective amount of a compound or pharmacutical composition of the invention.

In a related embodiment, there is provided a method for modulation, preferably inhibition, of $\alpha_v\beta_3$ and/or $\alpha_v\beta_5$ and/or $\alpha_v\beta_6$ and/or $\alpha_5\beta_1$ receptors which comprises administering to a warm blooded animal in need thereof an effective amount of a compound or pharmacutical composition of the invention.

An additionally preferred embodiment of the invention includes a method for the therapeutic or prophylactic treatment of an integrin receptor mediated disease state in a warm-blooded animal which comprises administering to said animal a therapeutically or prophylactically effective amount of a compound or pharmacutical composition of the invention. For example, the compounds of the invention may modulate an integrin receptor mediated response, for example, by antagonizing one or more vitronectin receptors response. Especially preferred in this embodiment is the inhibition of the $\alpha_v\beta_3$ and/or $\alpha_v\beta_5$ and/or $\alpha_v\beta_6$ and/or $\alpha_5\beta_1$ receptor response.

The compounds and pharmacutical compositions of this invention are useful in the prophylaxis and/or treatment (comprising administering to a warm blooded animal, such as a mammal (e.g., a human, horse, sheep, pig, mouse, rat, bovine and the like) an effective amount of such compound or composition) of (1) diseases and disorders which can be effected or facilitated by modulating one or more integrin receptors, such as by antagonizing one or more integrin receptors, including but not limited to disorders induced or facilitated by one or more integrin receptors; (2) diseases and disorders which can be effected or facilitated by modulating one or more vitronectin receptors, such as by antagonizing one or more vitronectin receptors, including but not limited to disorders induced or facilitated by one or more vitronectin receptors; (3) diseases and disorders which can be effected or facilitated by modulating the $\alpha_v\beta_3$ and/or $\alpha_v\beta_5$ and/or $α_vβ_6$ and/or $α_5β_1$ receptor response, such as by inhibition of the $α_vβ_3$ and/or $α_vβ_5$ and/or $α_vβ_6$ and/or $α_5β_1$ receptor response, including but not limited to disorders induced or facilitated by the $α_vβ_3$ and/or $α_vβ_5$ and/or $α_vβ_6$ and/or $α_5β_1$ receptor response; or (4) disease states involving cancer, such as tumor growth; metastasis; diabetic retinopathy; macular degeneration; angiogenesis; restenosis; bone resorption, such as osteoporosis, osteoarthritis, bone formation, bone loss, hyperparathyroidism, Paget's disease, hypercalcemia of malignancy, osteolytic lesions, Behcet's disease, osteomalacia, hyperostosis or osteopetrosis; atherosclerosis; inflammation, such as rheumatoid arthritis, pain, psoriasis or allergies; viral disease; wound healing; or the like.

As utilized herein, the following terms shall have the following meanings:

"Alkyl", alone or in combination, means a saturated or partially unsaturated (provided there are at least two carbon atoms) straight-chain or branched-chain alkyl radical containing preferably 1–18 carbon atoms ($C_1$–$C_{18}$), more preferably 1–12 carbon atoms ($C_1$–$C_{12}$), more preferably 1–8 carbon atoms ($C_1$–$C_8$), more preferably 1–6 carbon atoms ($C_1$–$C_6$), more preferably 1–4 carbon atoms ($C_1$–$C_4$), more preferably 1–3 carbon atoms ($C_1$–$C_3$), and most preferably 1–2 carbon atoms ($C_1$–$C_2$). Examples of such radicals include methyl, ethyl, vinyl, n-propyl, allyl, isopropyl, n-butyl, 1-butenyl, 2-butenyl, 3-butenyl, sec-butyl, sec-butenyl, t-butyl, n-pentyl, 2-methylbutyl, 3-methylbutyl, 3-methylbutenyl, n-hexyl, 2-methylpentyl, 3-methylpentyl, 4-methylpentyl, 2,2-dimethylbutyl, 2,3-dimethylbutyl, and the like. A partially unsaturated alkyl preferably has at least one double or triple bond, more preferably 1–3 double or triple bonds, more preferably 1–2 double or triple bonds, and most preferably 1 double bond or 1 triple bond. "-Alkyl-" is a divalent alkyl radical (e.g., $R_{21}R_{22}$N-alkyl, $R_{21}$O-alkyl, etc.)

"Aryl-alkyl-", alone or in combination, means an alkyl radical as defined above wherein a hydrogen radical is replaced with a aryl radical, such as phenylmethyl. "Alkyl-aryl-", alone or in combination, means an aryl radical wherein a hydrogen radical of the aryl moiety is replaced with a alkyl radical, such as 4-methylphenyl.

"Alkoxy", alone or in combination, means a radical of the type "R—O—" wherein "R" is an alkyl radical as defined above and "O" is an oxygen atom. Examples of such alkoxy radicals include methoxy, ethoxy, n-propoxy, isopropoxy, n-butoxy, iso-butoxy, sec-butoxy, tert-butoxy, allyloxy and the like.

"Alkylthio", alone or in combination, means a radical of the type "R—S—" wherein "R" is an alkyl radical as defined above and "S" is a sulfur atom. Examples of such alkylthio radicals include methylthio, ethylthio, n-propylthio, isopropylthio, n-butylthio, iso-butylthio, sec-butylthio, tert-butylthio, allylthio and the like.

"Methylenedioxy" means the divalent radical —O—$CH_2$—O—. "Ethylenedioxy" means the divalent radical —O—$CH(CH_3)$—O— or O—$CH_2CH_2$—O—. "Propylenedioxy" means the divalent radical —O—CH($CH_2CH_3$)—O—, —O—C($CH_3$)$_2$—O—, —O—CH($CH_3$)$CH_2$—O— or —O—$CH_2CH_2CH_2$—O—.

The term "carbocyclic", alone or in combination, refers to an organic cyclic moiety in which the cyclic skeleton is comprised of only carbon atoms whereas the term "heterocyclic", alone or in combination, refers to an organic cyclic moiety in which the cyclic skeleton contains one or more, preferably 1–4, more preferably 1–3, most preferably 1–2, heteroatoms selected from nitrogen, oxygen, or sulfur and which may or may not include carbon atoms.

The term "cycloalkyl", alone or in combination, refers to a saturated or partially unsaturated (preferably 1–2 double bonds, more preferably 1 double bond) carbocyclic moiety containing the indicated number of carbon atoms, preferably 3–12 ring members, more preferably 3–10 ring members, more preferably 3–8 ring members, and most preferably, 3–6 ring members. For example, the term "$C_3$–$C_{10}$ cycloalkyl" refers to an organic cyclic substituent in which three to ten carbon atoms form a three, four, five, six, seven, eight, nine or ten-membered ring, including, for example, a cyclopropyl, cyclobutyl, cyclopentyl, cyclopentenyl, cyclohexenyl, cyclohexyl, cycloheptyl, cyclooctyl and the like ring. As used herein, "cycloalkyl" may also refer to two or more cyclic ring systems which are fused to form, for example, bicyclic, tricyclic, or other similar bridged compounds (e.g. tetrahydroindan, decahydronaphthylene, hexahydroindan, norbornanyl, norbornenyl, adamantanyl, etc.). "-Cycloalkyl-" is a divalent cycloalkyl radical.

"Aryl" refers to an aromatic carbocyclic group having a single ring, for example, a phenyl ring, multiple rings, for example, biphenyl, or multiple condensed rings in which at least one ring is aromatic, for example, naphthyl, 1,2,3,4-tetrahydronaphthyl, anthryl, or phenanthryl, which can be unsubstituted or substituted with one or more (preferably 1–5, more preferably 1–4, more preferably 1–3, most preferably 1–2) other substituents as defined above. The substituents attached to a phenyl ring portion of an aryl moiety in the compounds of this invention may be configured in the ortho-, meta- or para-orientations. "-Aryl-" is a divalent aryl radical. Examples of typical aryl moieties included in the scope of the present invention may include, but are not limited to, the following:

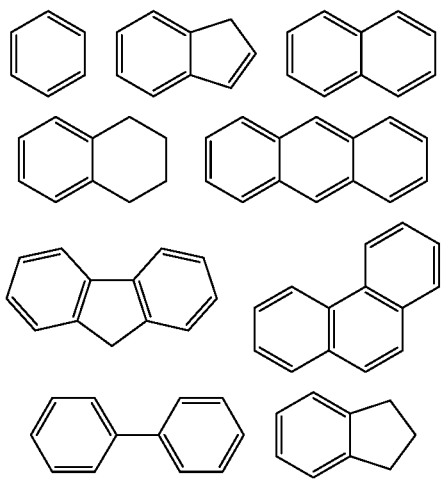

"Aryloxy" refers to an aryl group, as defined above, directly attached to an oxygen atom, which in turn is bonded to another atom. Thus, for example, phenyloxy, refers to a phenyl moiety linked through an oxygen atom to another substituent (e.g., phenyl-O—).

"Heterocycle" refers to a saturated, unsaturated or aromatic carbocyclic group having a single ring, multiple rings or multiple condensed rings, and having at least one hetero atom such as nitrogen, oxygen or sulfur within at least one of the rings. "Heteroaryl" refers to a heterocyclyl moiety in which at least one ring is aromatic. Further, bi- or tri-cyclic heteroaryl moieties may comprise at least one ring which is either completely or partially saturated. Any of the heteroaryl groups can be unsubstituted or optionally substituted with one or more groups as defined above and one or more, preferably 1–2, more preferably one, "oxo" group. "-Heteroaryl-" is a divalent heteroaryl radical. "Heterocyclyl" refers to a saturated or partially unsaturated, preferably one double bond, monocyclic or bicyclic, preferably monocyclic, heterocycle radical containing at least one, preferably 1 to 4, more preferably 1 to 3, even more preferably 1–2, nitrogen, oxygen or sulfur atom ring member and having preferably 3–8 ring members in each ring, more preferably 5–8 ring members in each ring and even more preferably 5–6 ring members in each ring. "Heterocyclyl" is intended to include sulfone and sulfoxide derivatives of sulfur ring members and N-oxides of tertiary nitrogen ring members, and carbocyclic fused, preferably 3–6 ring carbon atoms and more preferably 5–6 ring carbon atoms. Any of the heterocyclyl groups can be unsubstituted or optionally substituted with one or more groups as defined above and one or more, preferably 1–2, more preferably one, "oxo" group. "-Heterocyclyl-" is a divalent heterocyclyl radical.

As one skilled in the art will appreciate such heterocycle moieties may exist in several isomeric forms, all of which are to be encompassed by the present invention. For example, a 1,3,5-triazine moiety is isomeric to a 1,2,4-triazine group. Such positional isomers are to be considered within the scope of the present invention. Likewise, the heterocyclyl or heteroaryl groups can be bonded to other moieties in the compounds of the invention. The point(s) of attachment to these other moieties is not to be construed as limiting on the scope of the invention. Thus, by way of example, a pyridyl moiety may be bound to other groups through the 2-, 3-, or 4-position of the pyridyl group and a piperidinyl may be bound to other groups through the nitrogen or carbon atoms of the piperidinyl group. All such configurations are to be construed as within the scope of the present invention.

Examples of heterocyclyl or heteroaryl moieties inclued in the scope of the present invention may include, but are not limited to, the following:

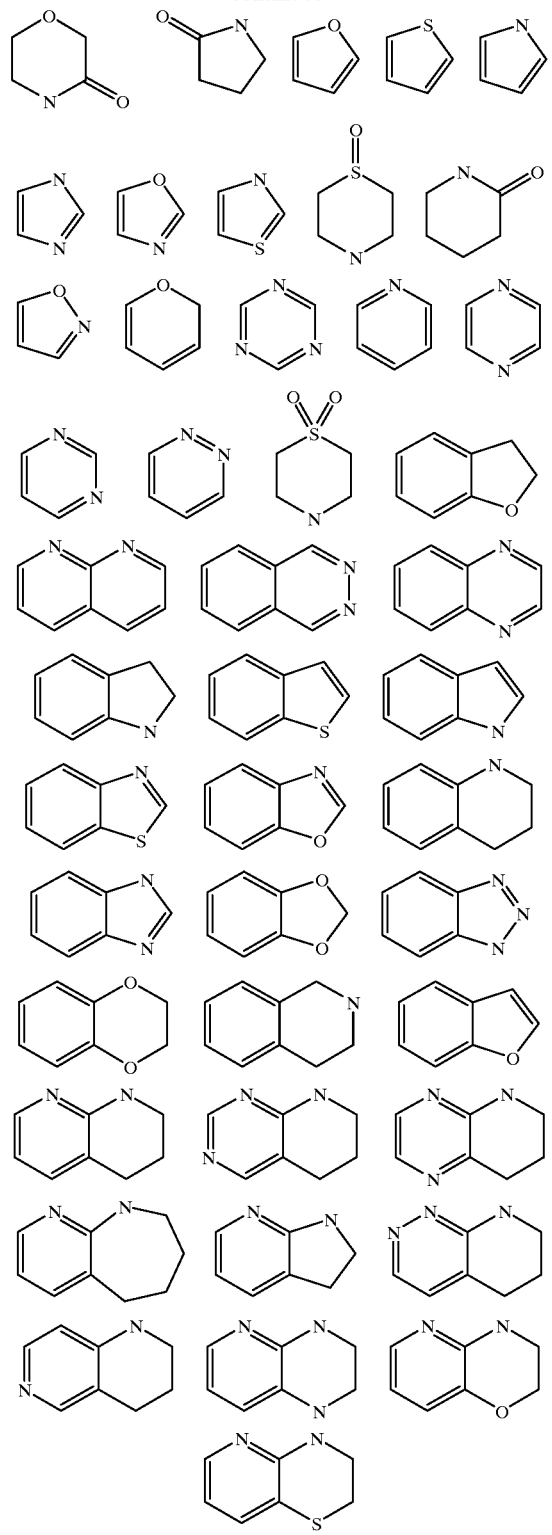

Heterocycle "fused" forms a ring system in which a heterocyclyl or heteroaryl group and a cycloalkyl or aryl group have two carbons in common, for example indole, isoquinoline, tetrahydroquinoline, methylenedioxybenzene and the like.

"Fused-aryl" (e.g., fused-phenyl) means that an aryl radical and another ring have two carbon atoms in common, for example naphthylene, indole, 1,2,3,4-tetrahydroquinoline, tetrahydronaphthylene, etc. "Fused-heteroaryl" means that a heteroaryl radical and another ring have two carbon atoms in common, for example indole, 5,6,7,8-tetrahydroquinoline and the like. "Benzo", alone or in combination, means the divalent radical $C_6H_4=$ derived from benzene.

"Spirocycloalkyll" means that a cycloalkyl and another ring have one carbon atom in common, i.e., a geminal attachment of the two rings. "Spiroheterocyclyl" means that a heterocyclyl radical and another ring have one carbon atom in common, i.e., a geminal attachment of the two rings.

The term "halo" or "halogen", alone or in combination, refers to a halogen atom which may include fluoro, chloro, bromo and iodo. Preferred halo groups include chloro, bromo and fluoro with chloro and fluoro being especially preferred.

"Haloalkyl" and "haloalkoxy", alone or in combination, means an alkyl or alkoxy radical, respectively, as defined above in which at least one hydrogen atom, preferably 1–7, more preferably 1–5, most preferably 1–3, is replaced by a halogen radical, more preferably fluoro or chloro radicals. Examples of such haloalkyl and haloalkoxy radicals include 1,1,1-trifluoroethyl, chloromethyl, 1-bromoethyl, fluoromethyl, difluoromethyl, trifluoromethyl, perfluoroethyl, perfluoropropyl, bis(trifluoromethyl)methyl, 2,2,2-trifluoroethoxy, trifluoromethoxy, and the like.

"Hydroxyalkyl", alone or in combination, means an alkyl radical as defined above in which at least one hydrogen atom, preferably 1–4, more preferably 1–3, most preferably 1–2, is replaced by a hydroxy radical, but not more than one hydroxy radical is attached to the same carbon atom.

Certain symbols used herein are indended to have the following meanings:

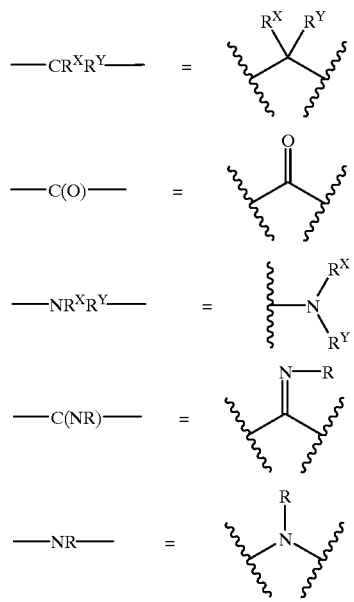

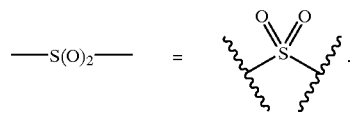

Further, a carbon atom substituted by two hydroxy radicals represents a carbonyl radical. For example, —CR$_2$R$_2$— represents a carbonyl radical when each R$_2$ is a hydroxy radical.

It should be noted that compounds of the invention may contain groups that may exist in tautomeric forms, such as cyclic and acyclic amidine and guanidine groups, heteroatom substituted heteroaryl groups (Y'=O, S, NR), and the like

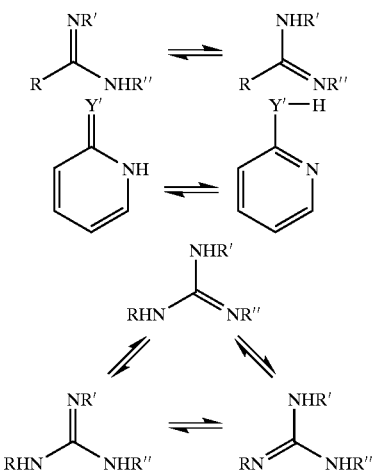

and though one form is named, described, displayed and/or claimed herein, all the tautomeric forms are intended to be inherently included in such name, description, display and/or claim.

"Modulate" as used herein refers to the ability of a compound of this invention to interact with a receptor, target gene or other gene product to (a) up-regulate the activity of that receptor, target gene or other gene product or biological effect (for example, as an agonist) or (b) down-regulating the receptor, target gene or other gene product or other biological effect, particularly by acting as an antagonist for the receptor, target gene or other gene product. Additionally, encompassed by "modulate" is the ability of a compound of the invention to effect a desired biological response, even if that response occurs upstream or downstream one or more steps in a signaling pathway from the receptor, target gene or other gene product in question. Thus, by way of example, the compounds of the invention may provide the desired effect by interacting with an integrin receptor, particularly a vitronectin receptor, such as the $\alpha_v\beta_3$ and/or $\alpha_v\beta_5$ and/or $\alpha_v\beta_6$ receptor, to act as an agonist or antagonist to that receptor or at some point, either upstream or downstream, in the signaling pathway for the receptor to effect the desired therapeutic or prophylactic response.

"Pharmaceutically acceptable salt", as used herein, refers to an organic or inorganic salt which is useful in the treatment of a warm-blooded animal. Such salts can be acid or basic addition salts, depending on the nature of the compound of this invention. For examples of "pharmacologically acceptable salts," see Berge et al., J. Pharm. Sci. 66:1 (1977). As used herein, "warm blooded animal"

includes a mammal, including a member of the human, equine, porcine, bovine, murine, canine, feline and the like species.

In the case of an acidic moiety in a compound of this invention, a salt may be formed by treatment of a compound of this invention with a basic compound, particularly an inorganic base. Preferred inorganic salts are those formed with alkali and alkaline earth metals such as lithium, sodium, potassium, barium and calcium. Preferred organic base salts include, for example, ammonium, dibenzylammonium, benzylammonium, 2-hydroxyethylammonium, bis(2-hydroxyethyl)ammonium, phenylethylbenzylamine, dibenzyl-ethylenediamine, and the like salts. Other salts of acidic moieties may include, for example, those salts formed with procaine, quinine and N-methylglucosamine, plus salts formed with basic amino acids such as glycine, ornithine, histidine, phenylglycine, lysine and arginine. An especially preferred salt is a sodium or potassium salt of a compound of this invention.

With respect to basic moieties, a salt is formed by the treatment of a compound of this invention with an acidic compound, particularly an inorganic acid. Preferred inorganic salts of this type may include, for example, the hydrochloric, hydrobromic, hydroiodic, sulfuric, phosphoric or the like salts. Preferred organic salts of this type, may include, for example, salts formed with formic, acetic, succinic, citric, lactic, maleic, fumaric, palmitic, cholic, pamoic, mucic, d-glutamic, d-camphoric, glutaric, glycolic, phthalic, tartaric, lauric, stearic, salicyclic, methanesulfonic, benzenesulfonic, para-toluenesulfonic, sorbic, puric, benzoic, cinnamic and the like organic acids. An especially preferred salt of this type is a hydrochloride or sulfate salt of a compound of this invention.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, α-methoxyethyl, groups such as α-(($C_1$–$C_4$)alkyloxy)ethyl; for example, methoxyethyl, ethoxyethyl, propoxyethyl, iso-propoxyethyl, etc.; 2-oxo-1,3-dioxolen-4-ylmethyl groups, such as 5-methyl-2-oxo-1,3, dioxolen-4-ylmethyl, etc.; $C_1$–$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Additionally, the compounds of the invention may have one or more asymmetric carbon atoms and, therefore, may exist in stereoisomeric forms. All stereoisomers are intended to be included within the scope of the present invention. As used, "stereoisomer" or "stereoisomeric" refers to a compound which has the same molecular weight, chemical composition, and constitution as another, but with the atoms grouped such that their orientation in three-dimensional space is different. Such stereoisomers may exist as enantiomeric mixtures, diastereomers or may be resolved into individual stereoisomeric components (e.g. specific enantiomers) by methods familiar to one skilled in the art.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

Further, the compounds of the invention may exist as crystalline solids which can be crystallized from common solvents such as ethanol, N,N-dimethyl-formamide, water, or the like. Thus, crystalline forms of the compounds of the invention may exist as solvates and/or hydrates of the parent compounds or their pharmaceutically acceptable salts. All of such forms likewise are to be construed as falling within the scope of the invention.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable carrier, which includes diluents, excipients and the like as described herein. A pharmaceutical composition of the invention may comprise an effective amount of a compound of the invention or an effective dosage amount of a compound of the invention. An effective dosage amount of a compound of the invention includes an amount less than or greater than an effective amount of the compound; for example, a pharmaceutical composition in which two or more unit dosages, such as in tablets, capsules and the like, are required to administer an effective amount of the compound, or alternatively, a multidose pharmaceutical composition, such as powders, liquids and the like, in which an effective amount of the compound is administered by adminstering a portion of the composition.

The compounds of the invention are administered by any suitable route, preferably in the form of a pharmaceutical composition adapted to such a route, and in a dose effective for the treatment intended. Therapeutically effective doses of the compounds of the present invention required to treat diseases and disorders are readily ascertained by one of ordinary skill in the art using standard methods.

The pharmaceutically active compounds of this invention can be processed in accordance with conventional methods of pharmacy to produce medicinal agents for administration to patients, including humans and other mammals.

The composition used in the noted therapeutic methods can be in a variety of forms. These include, for example, solid, semi-solid and liquid dosage forms, such as tablets, pills, powders, liquid solutions or suspensions, liposomes, injectable and infusible solutions. The preferred form depends on the intended mode of administration and therapeutic application. Considerations for preparing appropriate formulations will be familiar to one skilled in the art and are described, for example, in Goodman and Gilman's: "The Pharmacological Basis of Therapeutics", 8th Ed., Pergamon Press, Gilman et al. eds. (1990); and "Remington's Pharmaceutical Sciences", 18th Ed., Mack Publishing Co., A. Gennaro, ed. (1990). Methods for administration are discussed therein, e.g. for oral, topical, intravenous, intraperitoneal, or intramuscular administration. Pharmaceutically acceptable carriers, diluents, and excipients, likewise, are discussed therein. Typical carriers, diluents, and excipients may include water (for example, water for injection), buffers, lactose, starch, sucrose, and the like.

As noted, a compound of the invention can be administered orally, topically or parenterally (e.g. intravenously, intraperitoneally, intramuscularly, subcutaneously, etc.), or inhaled as a dry powder, aerosol, or mist, for pulmonary delivery. Such forms of the compounds of the invention may be administered by conventional means for creating aerosols or administering dry powder medications using devices such as for example, metered dose inhalers, nasal sprayers, dry powder inhaler, jet nebulizers, or ultrasonic nebulizers. Such devices optionally may be include a mouthpiece fitted around an orifice. In certain circumstances, it may be desirable to administer the desired compound of the invention by continuous infusion, such as through a continuous infusion pump, or using a transdermal delivery device, such as a patch.

The compounds of the invention may also be administered as an aerosol. The term "aerosol" includes any gas-borne suspended phase of a compound of the invention which is capable of being inhaled into the bronchioles or nasal passages. Specifically, aerosol includes a gas-borne suspension of droplets of the desired compound, as may be produced in a metered dose inhaler or nebulizer, or in a mist sprayer. Aerosol also includes a dry powder composition of a compound of the instant invention suspended in air or other carrier gas, which may be delivered by insufflation from an inhaler device, for example.

For solutions used in making aerosols of the invention, the preferred range of concentration of the compounds of the invention is 0.1–100 milligrams (mg)/milliliter (mL), more preferably 0.1–30 mg/mL, and most preferably 1–10 mg/mL. Usually the solutions are buffered with a physiologically compatible buffer such as phosphate or bicarbonate. The usual pH range is from about 5 to about 9, preferably from about 6.5 to about 7.8, and more preferably from about 7.0 to about 7.6. Typically, sodium chloride is added to adjust the osmolarity to the physiological range, preferably within 10% of isotonic. Formulation of such solutions for creating aerosol inhalants is discussed, for example, in Remington's, supra; See, also, Ganderton and Johens, "Drug Delivery to the Respiratory Tract, Ellis Horwood (1987); Gonda, "Critical Review in Therapeutic Drug Carrier Systems" 6 273–313 (1990); and Raeburn et al. J. Pharmacol. Toxicol. Methods. 27 143–159 (1992).

Solutions of a compound of the invention may be converted into aerosols by any of the known means routinely used for making aerosol inhalant pharmaceuticals. In general, such methods comprise pressurizing or providing a means of pressurizing a container of the solution, usually with an inert carrier gas, and passing the pressurized gas through a small orifice, thereby pulling droplets of the solution into the mouth and trachea of the animal to which the drug is to be administered. Typically, a mouthpiece is fitted to the outlet of the orifice to facilitate delivery into the mouth and trachea.

In one embodiment, devices of the present invention comprise solutions of the compounds of the invention connected to or contained within any of the conventional means for creating aerosols in asthma medication, such as metered dose inhalers, jet nebulizers, or ultrasonic nebulizers. Optionally such devices may include a mouthpiece fitted around the orifice.

Further, there are provided a device which may comprise a solution of a compound of the instant invention in a nasal sprayer.

A dry powder comprising a compound of the invention, optionally with an excipient is another embodiment. This may be administered by a drug powder inhaler containing the described powder.

Powders may be formed with the aid of any suitable powder bases, for example, talc, lactose, starch and the like. Drops may be formulated with an aqueous base or non-aqueous base also comprising one or more dispersing agents, suspending agents solubilizing agents, and the like.

Any of the formulations of the invention may also include one or more preservatives or bacteriostatic agents, for example, methyl hydroxybenzoate, ethyl hydroxybenzoate, propyl hydroxybenzoate, chlorocresol, benzalkonium chlorides, and the like. Additionally, the formulations may contain other active ingredients.

The pharmaceutical formulations of the invention may be administered by parenteral or oral administration for prophylactic and/or therapeutic treatment. The pharmaceutical compositions can be administered in a variety of unit dosage forms depending on the method of administration. For example, unit dosage forms suitable for oral administration may include, powders, tablets, pills, capsules and dragées.

The pharmaceutical formulations can be administered intravenously. Therefore, the invention further provides formulations for intravenous administration which comprise a compound of the invention dissolved or suspended in a pharmaceutically acceptable carrier or diluent therefor. A variety of aqueous carriers can be used, for example, water, buffered water or other buffer solutions, saline, and the like. The resulting aqueous solutions can be packaged for use as is, or lyophilized, the lyophilized preparation being combined with a sterile aqueous solution prior to administration. The sterile aqueous solution for the lyophilized product can be packaged as a kit for use with the lyophilized formulation. The compositions can contain pharmaceutically acceptable substances to aid in administration and more closely mimic physiological conditions. Such substances, can include, for example, pH adjusting substances such as acids, bases or buffering agents, tonicity adjusting agents, wetting agents and the like. Such substances may include but are not limited to, for example, sodium hydroxide, hydrochloric acid, sulfuric acid, sodium acetate, sodium lactate, sodium chloride, potassium chloride, calcium chloride, sorbitan monolaurate, triethanolamine oleate, and the like or any other means familiar to one skilled in the art for maintaining pH at a desired level.

For solid formulations, carriers, diluents, and excipients known to one skilled in the art may be used. Such carriers, diluents and excipients may include, for example, mannitol, lactose, starch magnesium stearate, sodium saccharin, talcum, cellulose, glucose, sucrose, or other solid polyol sugar, magnesium carbonate, and the like. For oral administration, a pharmaceutically acceptable formulation is prepared by admixing any of the usual carrier, diluents, and excipients, such as those noted, with from about 0.1 to about 95% of a compound of the invention.

The preferred dosage for use in the methods of the invention, however, is in the range of about 0.01 mg/kg to about 100 mg/kg of body weight, preferably from about 0.1 mg/kg to about 50 mg/kg, up to 4 times per day. Whatever the dosage form, one skilled in the art will recognize that the dosage administered will be adjusted to factors such as the age, weight, and condition of the patient involved. The skilled practitioner will be familiar with how to adjust the dosage to accommodate these and other factors.

While the compounds of the invention can be administered as the sole active pharmaceutical agent, the compounds can also be used in combination with one or more agents such as anti-platelet agents, anti-inflammatory agents, matrix metalloproteinase inhibitors, cancer treatment agents, antiinfective agents and the like. For example, the compounds of the invention can be administered in combination with glycoprotein IIb/IIIa receptor antagonists for the prophylaxis and/or treatment of acute coronary ischemic syndrome and the like (WO 97/35615, incorporated herein by reference in its entirety), or in combination with IL-1 antagonists, such as, p38 inhibitors, TNF-α inhibitors, TNF-α binding agents (such as TNF-α binding proteins), IL-1 inhibitors, IL-1 receptor antagonist (IL-1Ra) and the like, for the prophylaxis and/or treatment of rheumatoid arthritis, osteoarthritis and the like (Arner et al., Arthritis & Rheumatism 38:1304–14, 1995). When administered as a combination, the therapeutic agents can be formulated as separate compositions which are given at the same time or different times, or the therapeutic agents can be given as a single composition.

Compound Synthesis

Compounds of the invention can be synthesized according to one or more of the following methods. It should be noted that the general procedures are shown as it relates to preparation of compounds having unspecified stereochemistry. However, such procedures are generally applicable to those compounds of a specific stereochemistry, e.g., where the stereochemistry about a group is (S) or (R). In addition, the compounds having one stereochemistry (e.g., (R)) can often be utilized to produce those having opposite stereochemistry (i.e., (S)) using well-known methods, for example, by inversion. Because compounds of the invention can possess one or more asymmetric carbon atoms, the compounds are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid or base. Examples of appropriate acids are tartaric acid, diacetyltartaric acid, dibenzoyltartaric acid, ditoluoyltartaric acid, camphorsulfonic acid and the like. Examples of appropriate bases are brucine, ephedrine, strychnine, morphine and the like. The separation of the mixture of diastereoisomers by crystallization is followed by liberation of the optically active bases from these salts. A alternative process for separation of optical isomers involves the use of a chiral chromatography column optimally chosen to maximize the separation of the enantiomers. Another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by utilizing optically active starting materials or alternatively, by generating optically active synthetic intermediates either by chiral reactions, such as using a chiral reagent, chiral catalyst and the like, or by isolating the desired chiral synthetic intermediate isomer using the methods described above. These isomers may be in the form of a free acid, a free base, an ester or a salt.

"Leaving group" (L) generally refers to groups readily displaceable by a nucleophile, such as an amine, a carbon, a thiol or an alcohol nucleophile. Such leaving groups are well known in the art. Examples of such leaving groups include, but are not limited to, halides (such as chloro, bromo, iodo), triflates, tosylates, mesylate, alkoxy (such as methoxy), alkylthio (such as methylthiol), alkylsulfonyl (such as methylsulfonyl), phenoxy, thiophenoxy, phenylsulfonyl, N-hydroxysuccinimide, N-hydroxybenzotriazole and the like. Thioethers may be oxidized to the corresponding sulfinyl groups by oxidation with an oxidizing agent, such as hydrogen peroxide, sodium periodate and the like. Thioethers and sulfinyl groups may be oxidized to the corresponding sulfonyl groups by oxidation with an oxidizing agent, such as potassium peroxymonosulfate, potassium permanganate, hydrogen peroxide and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like (see Greene, T. W. and Wuts, P. G. M., Protective Groups in Organic Synthesis, Wiley, 1991). Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl and the like. Examples of cycloalkenylalkyl or substituted cycloalkylenylalkyl radicals, preferably have 6–10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also sutiable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium flouride reagent, either as a discrete reaction step or in situ during a reaction with the alcohol group. Suitable silylating agents are, for example, trimethylsilyl chloride, tert-buty-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxy carbonyl protecting group can be removed utilizing an inorganic or organic acid, such as HCl or trifluoro-acetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydroylsis and hydrogenolysis conditions well known to those skilled in the art.

Compounds of the invention may be prepared as described in the following schemes and synthetic examples.

Compounds of the invention, U—V—A-(Alk)$_j$-(C(O)—NH)$_h$-(Alk)$_g$-B, can be prepared by one or more of the following coupling reactions using reagents, reaction conditions and solvents typical for such coupling reactions. For compounds of the invention where k is 1, the hydroxy, thiol and amine of HO—V—A-(Alk)$_j$-(C(O)—NH)$_h$-(Alk)$_g$-B, HS—V—A-(Alk)$_j$-(C(O)—NH)$_h$-(Alk)$_g$-B or H$_2$N—V—A-(Alk)$_j$-(C(O)—NH)$_h$-(Alk)$_g$-B, respectively, may be alkylated in the presence of base (such as sodium hydride, sodium methoxide, triethylamine and the like) in a dry solvent (such as ether, tetrahydrofuran and the like) to L-alkyl-NHP$_2$, L-alkyl-C(O)—OP$_1$ or L-alkyl-OP$_3$, wherein P$_1$ is a carboxylic acid protecting group (such as methyl, ethyl, benzyl or the like), P$_2$ is an amine protecting group (such as t-butoxycarbonyl (BOC), benzyloxycarbonyl and the like) and P$_3$ is an alcohol protecting group (such as benzyl and the like). The —NHP$_2$ group may then be deprotected and reacted with L$_1$—C(Q)—R$_1$, L$_1$—C(Q)—NH—R$_1$, L$_1$—C(Q)—O—R$_1$ or L$_2$—R$_1$, wherein L$_1$ and L$_2$ are leaving groups (such as chloro, bromo, triflate, and the like), to yield the corresponding compounds R$_1$—C(Q)—NH-alkyl-G—V—A-(Alk)$_j$-(C(O)—NH)$_h$-(Alk)$_g$-B, R$_1$—NH—C(Q)—NH-alkyl-G—V—A-(Alk)$_j$-(C(O)—NH)$_h$-(Alk)$_g$-B, R$_1$—O—C(Q)—NH-alkyl-G—V—A-(Alk)$_j$-(C(O)—NH)$_h$-(Alk)$_g$-B and R$_1$—NH-alkyl-G—V—A-(Alk)$_j$-(C(O)—NH)$_h$-(Alk)$_g$-B, respectively. Alternatively, the —OP$_3$ group may be deprotected, the resulting alcohol group may be converted into a leaving group (such as halogen, triflate, tosylate, mesylate and the like) and undergo nucleophilic displacement reaction with R$_1$—C(Q)—NH$_2$, R$_1$—NH—C(Q)—NH$_2$, R$_1$—O—C(Q)—NH$_2$ or R$_1$—NH$_2$ to yield R$_1$—C(Q)—NH-alkyl-G—V—A-(Alk)$_j$-(C(O)—NH)$_h$-(Alk)$_g$-B, R$_1$—NH—C(Q)—NH-alkyl-G—V—A-(Alk)$_j$-(C(O)—NH)$_h$-(Alk)$_g$-B, R$_1$—O—C(Q)—NH-alkyl-G—V—A-(Alk)$_j$-(C(O)—NH)$_h$-(Alk)$_g$-B and R$_1$—NH-alkyl-G—V—A-(Alk)$_j$-(C(O)—NH)$_h$-(Alk)$_g$-B, respectively. Further alternatively, the resulting alcohol group may be oxidized into an aldehyde or ketone group which can undergo reductive amination reaction with, for example, R$_1$—NH$_2$ to yield R$_1$—NH-alkyl-G—V—A-(Alk)$_j$-(C(O)—NH)$_h$-(Alk)$_g$-B. The —C(O)—OP$_1$ group may be deprotected, the resulting carboxylic acid may be converted into an acid halide or active ester (such as N-hydroxysuccinimide ester, N-hydroxybenzotriazole ester and the like) and undergo nucleophilic displacement reaction with R$_1$—NH$_2$ to yield R$_1$—NH—C(Q)-alkyl-G—V—A-(Alk)$_j$-(C(O)—NH)$_h$-(Alk)$_g$-B. Finally, the —OP$_3$ group may be deprotected and the resulting alcohol group may undergo nucleophilic displacement reaction with L$_1$—C(Q)—NH—R$_1$ in the presence of base (such as sodium hydride and the like) to yield R$_1$—NH—C(Q)—O-alkyl-G—V—A-(Alk)$_j$-(C(O)—NH)$_h$-(Alk)$_g$-B. Alternatively, the above compounds may be prepared from HO—V—A-(Alk)$_j$-C(O)—OP$_1$, HS—V—A-(Alk)$_j$-C(O)—OP$_1$ or H$_2$N—V—A-(Alk)$_j$-C(O)—OP$_1$, respectively, by derivatization as described above followed by conversion of the —C(O)—OP$_1$ group into an acid halide or active ester as described above and nucleophilic displacement reaction thereof with B-(Alk)$_g$-NH$_2$.

For compounds of the invention where k is 0, the amine, H$_2$N—V—A-(Alk)$_j$-(C(O)—NH)$_h$-(Alk)$_g$-B, may undergo nucleophilic displacement reaction with L$_1$—C(Q)—R$_1$, L$_1$—C(Q)—NH—R$_1$, L$_1$—C(Q)—O—R$_1$ or L$_2$—R$_1$ as described above to yield R$_1$—C(Q)—NH—V—A-(Alk)$_j$-(C(O)—NH)$_h$-(Alk)$_g$-B, R$_1$—NH—C(Q)—NH—V—A-(Alk)$_j$-(C(O)—NH)$_h$-(Alk)$_g$-B, R$_1$—O—C(Q)—NH—V—A-(Alk)$_j$-(C(O)—NH)$_h$-(Alk)$_g$-B and R$_1$—NH—V—A-(Alk)$_j$-(C(O)—NH)$_h$-(Alk)$_g$-B, respectively. The compound L$_1$—C(Q)—V—A-(Alk)$_j$-(C(O)—NH$_h$-(Alk)$_g$-B may undergo nucleophilic displacement reaction with R$_1$—NH$_2$ as described above to yield R$_1$—NH—C(Q)—V—A-

(Alk)$_j$-C(O)—NH)$_h$-(Alk)$_g$-B. Finally, the alcohol, HO—V—A-(Alk)$_j$-(C(O)—NH)$_h$-(Alk)$_g$-B, may undergo nucleophilic displacement reaction with L$_1$—C(Q)—NH—R$_1$ as described above to yield R$_1$—NH—C(Q)—O—V—A-(Alk)$_j$-(C(O)—NH)$_h$-(Alk)$_g$-B. Alternatively, the above compounds may be prepared from H$_2$N—V—A-(Alk)$_j$-C(O)—OP$_1$, L$_1$—C(Q)—V—A-(Alk)$_j$-C(O)—OP$_1$ and HO—V—A-(Alk)$_j$-C(O)—OP$_1$, respectively, by derivatization as described above followed by conversion of the —C(O)—OP$_1$ group into an acid halide or active ester as described above and nucleophilic displacement reaction thereof with B-(Alk)$_g$—NH$_2$.

The intermediates HO—V—A-(Alk)$_j$-(C(O)—NH)$_h$-(Alk)$_g$-B, HS—V—A-(Alk)$_j$-(C(O)—NH)$_h$-(Alk)$_g$-B and H$_2$N—V—A-(Alk)$_j$-(C(O)—NH)$_h$-(Alk)$_g$-B may be prepared from HO—V—A-(Alk)$_j$-C(O)—OP$_1$, HS—V—A-(Alk)$_j$-C(O)—OP$_1$ and H$_2$N—V—A-(Alk)$_j$-C(O)—OP$_1$, respectively, by deprotection of the —C(O)—OP$_1$ group, conversion of the resulting carboxylic acid into an acid halide or active ester as described above and nucleophilic displacement reaction thereof with B-(Alk)$_g$—NH$_2$. Depending on the activation and reaction conditions used, the hydroxy, thiol and/or amino groups may require protection with an appropriate protecting group to avoid condensation of the acid halide or active ester with the hydroxy, thiol or amino group.

When h is 0, the intermediates HO—V—A-(Alk)$_3$-B, HS—V—A-(Alk)$_j$-B and H$_2$N—V—A-(Alk)$_3$-B may be prepared from HO—V—A-(Alk)$_j$-CR$_{15}$, R$_{16}$, —CR$_{17}$, R$_{18}$, —C(O)—OP$_1$, HS—V—A-(Alk)$_j$—CR$_{15}$, R$_{16}$, —CR$_{17}$, R$_{18}$, —C(O)—OP$_1$ and H$_2$N—V—A-(Alk)$_j$-CR$_{15}$, R$_{16}$, —CR$_{17}$, R$_{18}$—C(O)—OP$_1$, respectively, by deprotection of the —C(O)—OP$_1$ group, conversion of the resulting carboxylic acid into an acid halide or active ester as described above and nucleophilic displacement reaction thereof with NH$_3$, HO—R$_{20}$, NH$_2$—R$_{20}$, NH$_2$—S(O)$_2$—R$_{20}$, NH$_2$—S(O)$_2$—R$_{20}$ or NH$_2$—C(O)—R$_{20}$, R$_{15}$, R$_{16}$, R$_{17}$, and R$_{18}$, represent R$_{15}$, R$_{16}$, R$_{17}$ and R$_{18}$, respectively, or radicals useful in the preparation of R$_{15}$, R$_{16}$, R$_{17}$ and R$_{18}$, respectively, as defined herein, such as protected and unprotected amino, hydroxy, thiol, carboxylic acid, thiocarboxylic acid, amido, thioamido, cyano and the like radicals and precursors thereof. Depending on the activation and reaction conditions used, hydroxy, thiol and/or amino groups may require protection with an appropriate protecting group to avoid condensation of the acid halide or active ester with the hydroxy, thiol or amino group.

The intermediate L$_1$—C(Q)—V—A-(Alk)$_j$-(C(O)—NH)$_h$-(Alk)$_g$-B, wherein Q is O or S, may be prepared from the corresponding carboxylic acid or thiocarboxylic acid using well known reagents and conditions, such as the preparation of acid halides, active esters and the like. The intermediate L$_1$—C(Q)—V—A-(Alk)$_j$-(C(O)—NH)$_h$-(Alk)$_g$-B, wherein Q is NH, N—CN or N-alkyl, may be prepared from the corresponding amido, thioamido, cyano and the like group using well known reagents and conditions used in the preparation of amidine and quanidine groups. The preparation of amidine groups, such as a —C(NR)—N(R')— radical, is well known to those skilled in the art (see Baati et al., Synthesis 1999:927–929; Dunn, Compr. Org. funct. Group Transform. 5:741–82 and 1161–308, 1995; and Gautier et al., Chem. Amidines Imidates, Patai (Ed.), Wiley (1975), pp. 283–348). Guanidine groups, such as a —N(R')—C(NR)—N(R")— radical, can be prepared from the corresponding (a) urea groups (e.g., by reaction with POCl$_3$ and a substituted amine in an organic solvent, such as toluene), (b) thiourea groups (e.g., by reaction with a substituted amine in the presence of CuSO$_4$, SiO$_2$ and a base, such as triethylamine, in an organic solvent such as tetrahydrofuran (Tet. Lett. 36:2841–4, 1995) or sodium periodate in the presence of base in dimethylformaide and water (Synlett 1997:1053–4)), (c) substituted cyanamide groups, —N(R)—CN (e.g., by reaction with a substituted amine), (d) imino ester amine groups, R'O—C(NR)—N(R')— (e.g., by reaction with a substituted amine), or (e) imino thioester amine groups, R'S—C(NR)—N(R')— by reaction with a substituted amine (Synth. Commun. 29:1757–66, 1999).

In general, J—V—A-(Alk)$_j$-(C(O)—NH)$_h$-(Alk)$_g$-B, wherein J— represents radicals useful in the preparation of U— radicals as defined herein, such as protected and unprotected amino, hydroxy, thiol, carboxylic acid, thiocarboxylic acid, amido, thioamido, cyano and the like radicals and precursors thereof, may be prepared from J—V—A-(Alk)$_j$-C(O)—OP$_1$ by deprotection of the —C(O)—OP$_1$ group, conversion of the resulting carboxylic acid into an acid halide or active ester as described above and nucleophilic displacement reaction thereof with B-(Alk)$_g$-NH$_2$. Alternatively, J—V—A-(Alk)$_j$-(C(O)—NH)$_h$-(Alk)$_g$-B may be prepared from J—V—A-(Alk)$_j$-CR$_{15}$R$_{16}$, —CR$_{17}$, R$_{18}$, —C(O)—OP$_1$ by deprotection of the —C(O)—OP$_1$ group, conversion of the resulting carboxylic acid into an acid halide or active ester as described above and nucleophilic displacement reaction thereof with NH$_3$, HO—R$_{20}$, NH$_2$—R$_{20}$, NH$_2$—S(O)—R$_{20}$, NH$_2$—S(O)$_2$—R$_{20}$ or NH$_2$—C(O)—R$_{20}$. Depending on the activation and reaction conditions used, the J— group may require protection with an appropriate protecting group to avoid condensation of the J— group with other reactive groups, such as the acid halide, active ester and the like.

Schemes 1–11 illustrate the preparation of the intermediate J—V—A—M, wherein M is -(Alk)$_j$-CO$_2$P$_1$ or -(Alk)$_j$-CR$_{15}$, R$_{16}$, —CR$_{17}$, R$_{18}$—CO$_2$P$_1$. Scheme 1 illustrates the formation of the ring A group when a nitrogen atom in ring A is coupled to the J—V— group. Ring A (2) may be formed by nucleophilic displacement reaction of L$_2$ of compound (1), wherein CR$_8$R$_9$ is other than a carbonyl and L$_2$ is a leaving group, such as chloro, bromo, iodo, triflyate, tosylate, mesylate and the like or alternatively, wherein CR$_8$R$_9$ is a carbonyl and L$_2$ is a leaving group, such as chloro, bromo, iodo, N-hydroxysuccinimide, N-hydroxybenzotriazole, methoxy, methylthiol, phenoxy, thiophenoxy and the like (Tetrahedron 55:6813–6830, 1999; J. Org. Chem. 63:9678–9683, 1998), by J—V—NH$_2$ in the presence of a base, such as triethylamine and the like, in an appropriate solvent, such as ether, tetrahydrofuran, dimethylformamide, dimethylsulfoxide and the like, followed by cyclization by nucleophilic displacement reaction of L$_1$ of compound (1), wherein L$_1$ is a leaving group, such as chloro, bromo, iodo, N-hydroxysuccinimide, N-hydroxybenzo-triazole, methoxy, methylthiol, phenoxy, thiophenoxy and the like, in the presence of an appropriate base, such as triethylamine, sodium hydride, sodium methoxide and the like, in an appropriate solvent, such as ether, tetrahydrofuran, dimethylformamide, dimethylsulfoxide and the like. Alternatively, L$_1$ may undergo nucleophilic displacement reaction by J—V—NH$_2$ followed by cyclization by nucleophilic displacement reaction of L$_2$. Further, alternatively, ring A (2) may be formed by the above reactions in a stepwise manner, such that one of the leaving groups is reacted with by J—V—NH$_2$, the the other leaving group is introduced into the intermediate followed by cyclication. For example, the L$_2$ in compound (1) may be a hydroxy group which can be converted into a leaving group after the reaction of L$_1$ with by J—V—NH$_2$.

Scheme 1

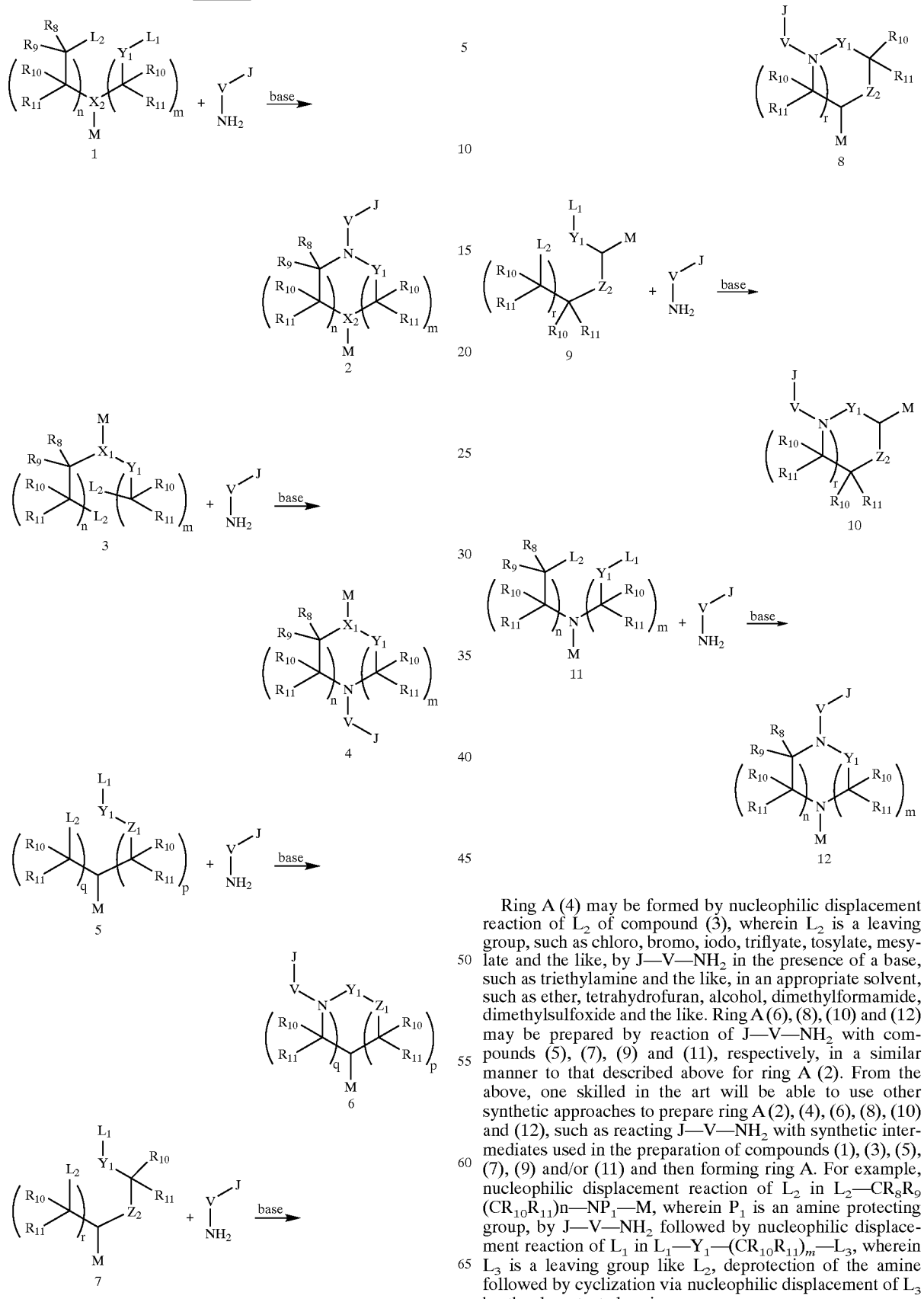

Ring A (4) may be formed by nucleophilic displacement reaction of $L_2$ of compound (3), wherein $L_2$ is a leaving group, such as chloro, bromo, iodo, triflyate, tosylate, mesylate and the like, by J—V—$NH_2$ in the presence of a base, such as triethylamine and the like, in an appropriate solvent, such as ether, tetrahydrofuran, alcohol, dimethylformamide, dimethylsulfoxide and the like. Ring A (6), (8), (10) and (12) may be prepared by reaction of J—V—$NH_2$ with compounds (5), (7), (9) and (11), respectively, in a similar manner to that described above for ring A (2). From the above, one skilled in the art will be able to use other synthetic approaches to prepare ring A (2), (4), (6), (8), (10) and (12), such as reacting J—V—$NH_2$ with synthetic intermediates used in the preparation of compounds (1), (3), (5), (7), (9) and/or (11) and then forming ring A. For example, nucleophilic displacement reaction of $L_2$ in $L_2$—$CR_8R_9$($CR_{10}R_{11}$)n—$NP_1$—M, wherein $P_1$ is an amine protecting group, by J—V—$NH_2$ followed by nucleophilic displacement reaction of $L_1$ in $L_1$—$Y_1$—$(CR_{10}R_{11})_m$—$L_3$, wherein $L_3$ is a leaving group like $L_2$, deprotection of the amine followed by cyclization via nucleophilic displacement of $L_3$ by the deprotected amine group.

As illustrated above, compounds (1), (3), (5), (7), (9) and (11) are commerically available or may be readily prepared using commerically available starting materials and synthetic methods and reagents well known to those skilled in the art.

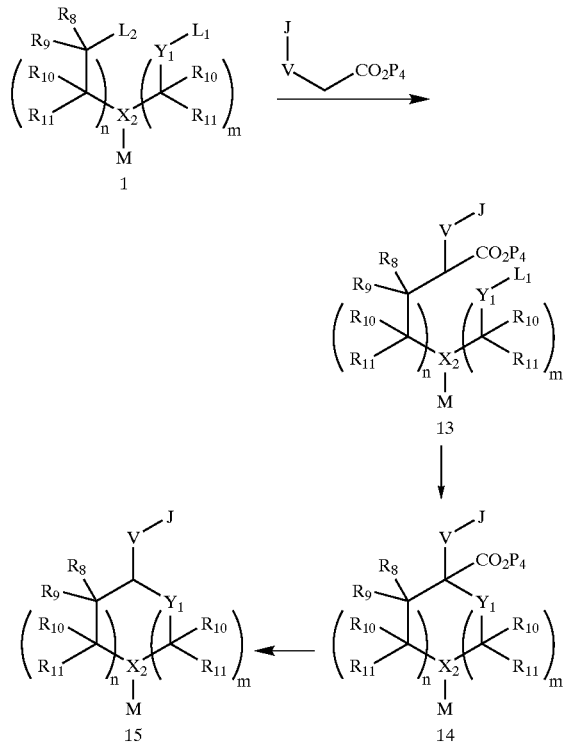

Scheme 2 illustrates the formation of the A group when $X_2$ is a carbon atom coupled to the J—V— group. Ring A (15) may be formed by nucleophilic displacement reaction of $L_2$ of compound (1), wherein $CR_8R_9$ is other than a carbonyl and $L_2$ is a leaving group, such as chloro, bromo, iodo, triflyate, tosylate, mesylate and the like or alternatively, wherein $CR_8R_9$ is a carbonyl and $L_2$ is a leaving group, such as chloro, bromo, iodo, N-hydroxysuccinimide, N-hydroxybenzotriazole, methoxy, methylthiol, phenoxy, thiophenoxy and the like, by J—V—$CH_2$—$CO_2P_4$ (or alternatively, the corresponding Wittig reagent (Chem. Rev. 89:863–927, 1989) or Horner-Wadsworth-Emmons condensation (Tet. Lett. 24:4405–4408, 1983)) in the presence of a base, such as sodium hydride, sodium methoxide, lithium diisopropylamine (LDA) and the like, in an appropriate solvent, such as ether, tetrahydrofuran and the like, followed by cyclization by nucleophilic displacement reaction of $L_1$ of compound (13), wherein $L_1$ is a leaving group, such as chloro, bromo, iodo, N-hydroxysuccinimide, N-hydroxybenzo-triazole, methoxy, methylthiol, phenoxy, thiophenoxy and the like, in the presence of an appropriate base, such as sodium hydride, sodium methoxide, lithium diisopropylamine and the like, in an appropriate solvent, such as ether, tetrahydrofuran and the like. The resulting compound (14) is then deprotected and decarboxyated to yield ring A (15). Alternatively, ring A (15) may be prepared by nucleophilic displacement of $L_1$ of compound (1) by (J—V—$CH_2$—)$_2$CuLi, J—V—$CH_2$—Li, J—V—$CH_2$—MgBr or the like followed by cyclization by nucleophilic displacement of $L_2$, which is preferably introduced following reaction of $L_2$, in the presence of an appropriate base, such as sodium hydride, sodium methoxide, lithium diisopropylamine and the like, in an appropriate solvent, such as ether, tetrahydrofuran and the like.

From the above, one skilled in the art will be able to use the above approach or alternative synthetic approaches to prepare ring A (15) when $X_2$ represents a nitrogen atom, such as reacting J—V—$CH_2$—$CO_2P_4$ with synthetic intermediates used in the preparation of compound (11) and then forming ring A. For example, nucleophilic displacement reaction of $L_2$ in $L_2$—$CR_8R_9(CR_{10}R_{11})_n$—$NP_1$—M, wherein $P_1$ is an amine protecting group, by J—V—$CH_2$—$CO_2P_4$ followed by nucleophilic displacement reaction of $L_1$ in $L_1$—$Y_1$—$(CR_{10}R_{11})_m$—$L_3$, wherein $L_3$ is a leaving group like $L_2$, deprotection of the amine followed by cyclization via nucleophilic displacement of $L_3$ by the deprotected amine group to yield compound (12).

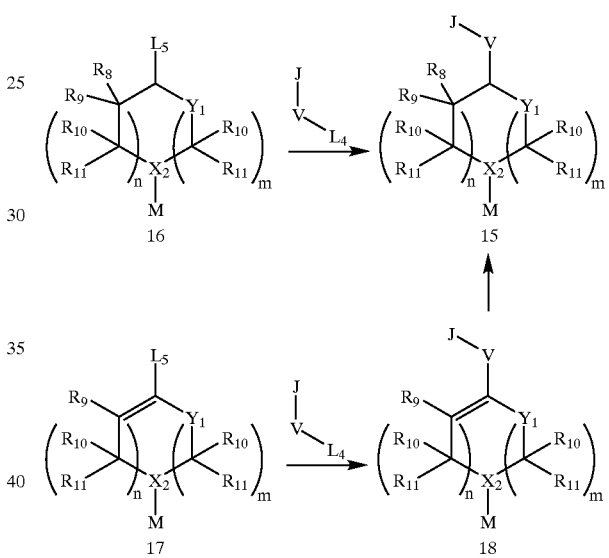

Scheme 3 illustrates alternative methods for the preparation of ring A (15) by direct coupling of compound (16), wherein $L_5$ is a hydrogen, chloro, bromo or iodo radical, and J—V—$L_4$, wherein $L_4$ is a chloro, bromo or iodo, in the presence of a strong base, such as $NaNH_2$, $KNH_2$, LDA and the like, in an appropriate solvent, such as ether, THF and the like. In addition, a catalyst, such as copper halide, palladium complex, lead tricarboxylates and the like, may be added to assist the reaction. Alternatively, J—V—$L_4$ may be coupled to compound 17, such as by the Heck reaction (Trans. Met. Org. Synth. 1:208–240, 1998; e.g., when $L_5$ is as halide, triflate or the like, in the presence of $Pd(PPh_3)_4$) and the like, followed by introduction of the $R_8$ group to compound (18) when $R_8$ is other than a hydrogen, such as by Michael-type nucleophilic reaction (e.g., $(R_8)_2$CuLi or the like) and the like, or reduction of the double bond, such as by hydrogenation (e.g., hydrogenation in the presence of Pd/C catalyst, magnesium in methanol and the like) and the like, when $R_8$ is a hydrogen. The processes of Scheme 3 are also applicable to the preparation of ring A (15) when $X_2$ represents a nitrogen atom.

Scheme 4

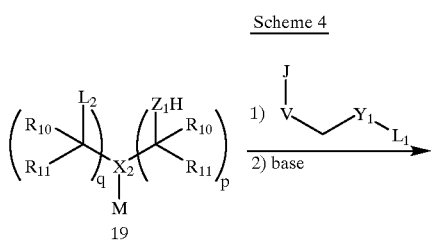
19

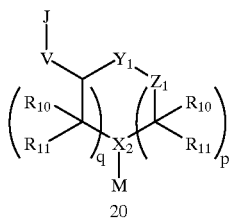
20

Scheme 4 illustrates the preparation of ring A (20). Ring A (20) can be formed by nucleophilic displacement of $L_1$ in J—V—CH$_2$—Y$_1$—L$_1$ by Z$_1$ of compound (19) in the presence of base, such as triethylamine and the like, followed by cyclization by nucleophilic displacement reaction of $L_2$ in the presence of base, such as sodium hydride, LDA and the like, in an appropriate solvent, such as ether, THF and the like. The process of Scheme 4 are also applicable to the preparation of ring A (15) when $X_2$ represents a nitrogen atom.

Scheme 5

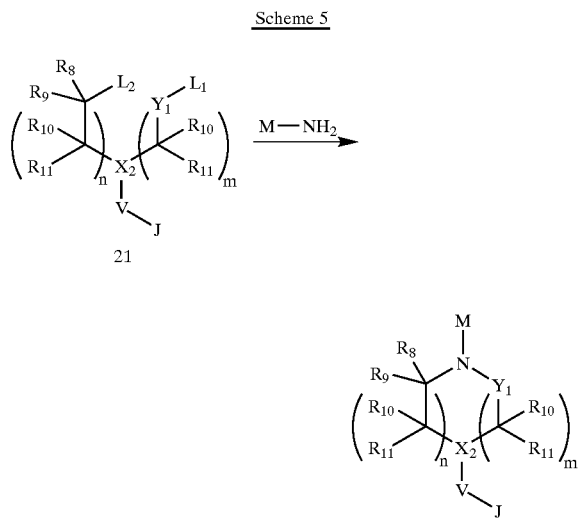

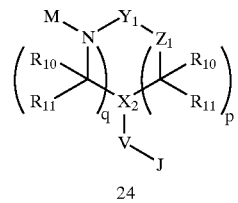
24

Scheme 5 illustrates the preparation of ring A (22) and (24). Ring A (22) and (24) can be prepared from compounds (21) and (23), respectively, in the same manner as described in Scheme 1. Compound (21) can be prepared by reacting J—V—X$_2$(H)—CO$_2$P$_1$ with L$_2$—(CR$_{10}$R$_{11}$)$_m$—Y$_1$—P$_5$, wherein P$_1$ and P$_5$ are protecting groups, in the presence of a base, such as sodium hydride and the like, to remove the proton on X$_2$ in an appropriate solvent, such as ether, THF and the like, followed by conversion of the —CO$_2$P$_1$ into —(CR$_{10}$R$_{11}$)$_m$—CR$_9$R$_8$—L$_2$ and —Y$_1$—P$_5$ into —Y$_1$—L$_1$ using processes and reagents well known to those skilled in the art. In a similar manner, Compound (23) can be prepared by reacting J—V—X$_2$(H)—CO$_2$P$_1$ with L$_2$—(CR$_{10}$R$_{11}$)$_p$—Z$_1$—Y$_1$—P$_5$ in the presence of a base followed by conversion of the —CO$_2$P$_1$ into —(CR$_{10}$R$_{11}$)$_q$—L$_2$ and —Y$_1$—P$_5$ into —Y$_1$—L$_1$ using processes and reagents well known to those skilled in the art. Alternatively, the introduction of the M—NH$_2$ moiety may be done in a stepwise manner, such as nucleophilic displacement of the L$_2$ group by M—NH$_2$ followed by conversion —Y$_1$—P$_5$ into —Y$_1$—L$_1$ and cyclization. Also, —Z$_1$—P$_5$ group may be present instead of —Z$_1$—Y$_1$—P$_5$ group in which case the —Z$_1$—P$_5$ group would be converted into the —Z$_1$—Y$_1$—L$_1$ group by reaction of —Z$_1$—H with L$_1$—Y$_1$—L$_1$ and the like.

Scheme 6

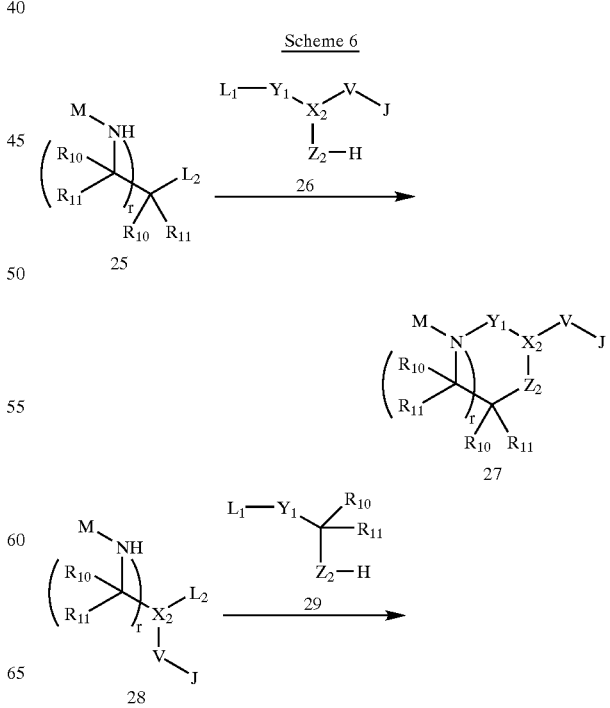

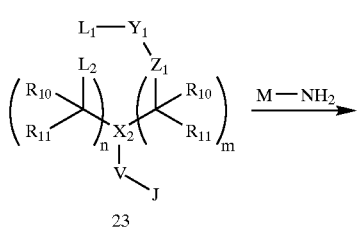
23

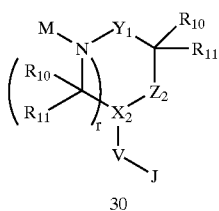

30

Scheme 6 illustrates the preparation of ring A (27) and (30). Ring A (27) can be prepared from compounds (25) and (26) and ring A (30) can be prepared from compounds (28) and (29) by nucleophilic displacement of $L_2$ by $Z_2$—H in the presence of base, such as triethylamine, sodium hydride and the like, in an appropriate solvent, such as ether, THF, DMF and the like, followed by nucleophilic displacement of $L_1$ by —NH— in the presence of base, such as triethylamine, sodium hydride and the like, in an appropriate solvent, such as ether, THF, DMF and the like. Alternatively, the order of the steps may be reversed, such that $L_1$ is displaced by —NH— and then $L_2$ is displaced by $Z_2$—H. Also, the groups to be reacted second are preferably protected during the first step and then converted into the reactive groups. For example, the —NH— is —NP$_2$— and $Y_1$—$L_1$ is $Y_1$—$P_5$, $L_2$ is displaced by $Z_2$—H, —NP$_2$— is converted into —NH— and $Y_1$—$P_5$ is converted into $Y_1$—$L_1$, and then $L_1$ is displaced by —NH—.

Scheme 7

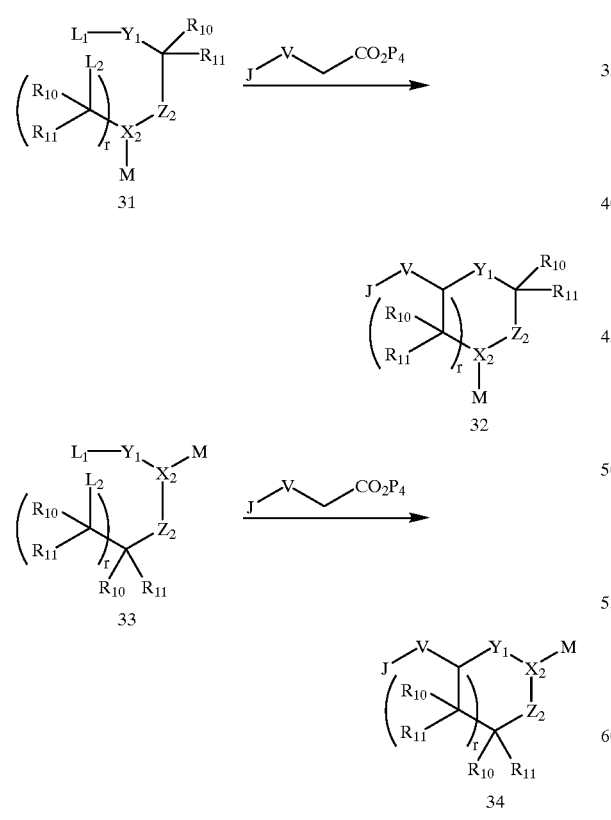

Scheme 7 illustrates the preparation of ring A (32) and (34). Ring A (32) and (34) can be prepared from compounds (31) and (33), respectively, by nucleophilic displacement of $L_1$ and $L_2$ by J—V—CH$_2$—CO$_2$P$_4$ in the presence of base, such as sodium hydride, LDA and the like, followed by deprotection and decarboxylation as described above in Scheme 2. Compound (31) can be prepared from P$_1$O—(CR$_{10}$R$_{11}$)$_r$—X$_2$(M)—L$_2$ by nucleophilic displacement of $L_2$ by HZ$_2$—CR$_{10}$R$_{11}$—Y$_1$—P$_5$ followed by conversion of $Y_1$—P$_5$ to $Y_1$—L$_1$ and P$_1$O— to —L$_2$. Alternatively, the conversions of $Y_1$—P$_5$ and P$_1$O— and reaction with J—V—CH$_2$—CO$_2$P$_4$ may be done in a stepwise fashion. Fro example, $Y_1$—P$_5$ is converted into $Y_1$—L$_1$, reacted with J—V—CH$_2$—CO$_2$P$_4$ and then P$_1$O— is converted into —L$_2$ followed by ring cyclization.

Scheme 8 illustrates the preparation of ring A (36) and (38). Ring A (36) and (38) can be prepared from compounds (35) and (37), respectively, by nucleophilic displacement of $L_1$ by $Z_2$ in the presence of base, such as triethylamine and the like, followed by cyclization by nucleophilic displacement of $L_2$ in the presence of base, such as sodium hydride, LDA and the like, as described above in Scheme 4.

Scheme 8

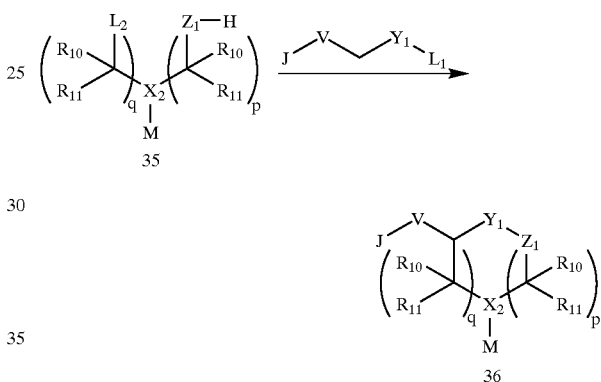

Scheme 9

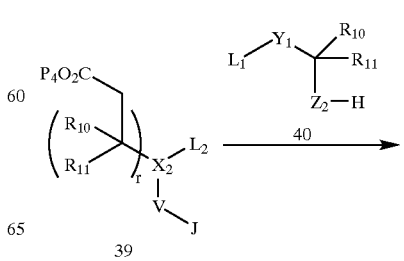

-continued

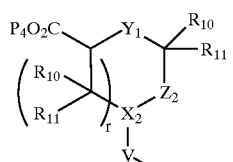

41

↓

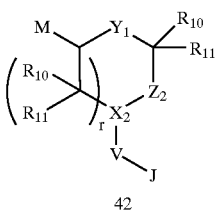

42

Scheme 9 illustrates the preparation of ring A (42). Compound (41) can be prepared from compounds (39) and (40) by nucleophilic displacement of $L_2$ by $Z_2$ in the presence of base, such as triethylamine and the like, followed by cyclization by nucleophilic displacement of $L_1$ in the presence of base, such as sodium hydride, LDA and the like, as described above. Ring A (42) can be prepared from compound (41) by nucleophilic displacement of $L_2$ of M—$L_2$ in the presence of base, such as sodium hydride, LDA and the like, followed by deprotection and decarboxylation of the —$CO_2P_4$ group. Alternatively, the —$CO_2P_4$ group can be converted into the M group using processes and reagents well known to those skilled in the art. For example, —$CO_2P_4$ group can be reduced to —$CH_2$—OH, converted into —$CH_2$—$L_2$ followed by nucleophilic displacement of the $L_2$ group with the appropriate organometallic reagent, such as $(P_1O_2C\text{-Alk-})_2CuLi$ and the like.

Scheme 10

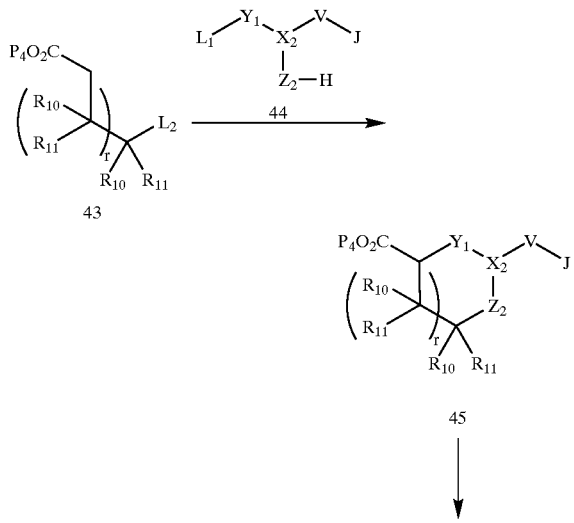

-continued

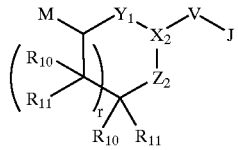

46

Scheme 10 illustrates the preparation of ring A (46). Compound (45) can be prepared from compounds (43) and (44) by nucleophilic displacement of $L_2$ by $Z_2$ in the presence of base, such as triethylamine and the like, followed by cyclization by nucleophilic displacement of $L_1$ in the presence of base, such as sodium hydride, LDA and the like, as described above. Ring A (46) can be prepared from compound (45) by nucleophilic displacement of $L_2$ of M—$L_2$ in the presence of base, such as sodium hydride, LDA and the like, followed by deprotection and decarboxylation of the —$CO_2P_4$ group. Alternatively, the —$CO_2P_4$ group can be converted into the M group using processes and reagents well known to those skilled in the art.

Scheme 11

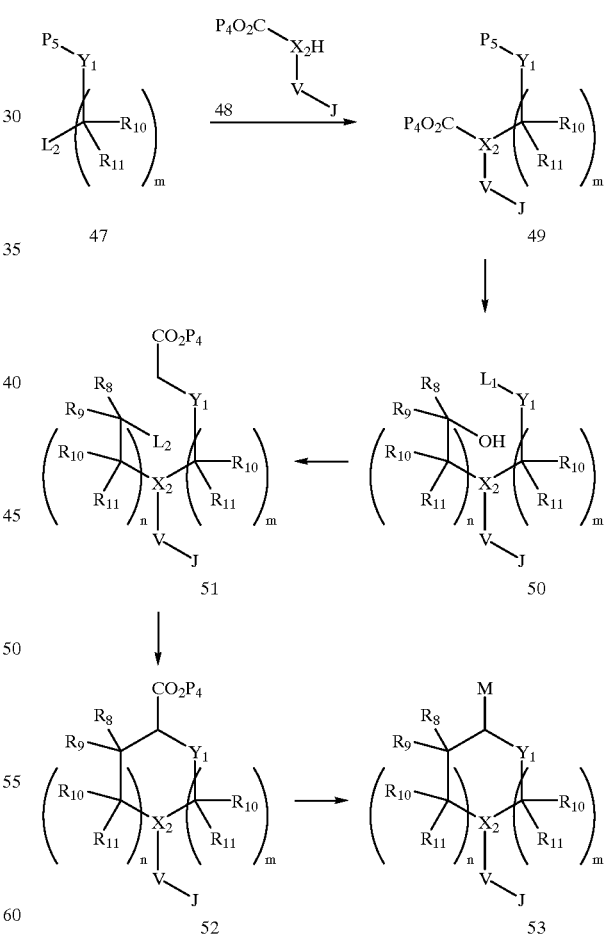

Scheme 11 illustrates the preparation of ring A (53). Compound (49) can be prepared from compounds (47) and (48) by nucleophilic displacement of $L_2$ in the presence of base, such as sodium hydride, LDA and the like. Compound (50) can be prepared from compound (49) by conversion of —$CO_2P_4$ into —$(R_{10}R_{11})$—$CR_8R_9$—OH (for example, by converting —$CO_2P_4$ into —$CH_2$—$CO_2P_4$, alkylating the —$CH_2$— group with $R_{10}$—$L_2$ and $R_{11}$—$L_2$ in the presence of base and reducing the —$CO_2P_4$ into —$CH_2$—OH), followed by conversion of $Y_1$—$P_5$ into $Y_1$—$L_1$. Compound (51) is prepared by nucleophilic displacement of $L_1$ of compound (50) by an acetate anion, such as $P_4O_2C$—$CH_2$—ZnBr and the like, followed by conversion of the —OH group into a leaving group, $L_2$. Compound (51) is then cyclized by nucleophilic displacement of $L_2$ in the presence of base, such as sodium hydride, LDA and the like, as described above, to form compound (52). Finally, compound (53) is prepared from compound (52) by converting —$CO_2P_4$ into —M as described in Scheme 9.

The reactions described above may be carried out in any number of solvents in which the reactants may be mutually soluble, including, for example, benzene, tetrahydrofuran, toluene, chloroform, dichloromethane, N,N-dimethylformamide, ethyl ether, dioxane, water, acetonitrile, or the like. Generally the reaction is carried out at a temperature of between −80° C. and 150° C., preferably, however, at room temperature. In certain cases, as noted in the examples provided herein, however, the temperature of the reaction may reach as high as or exceed about −360° C.

The product and intermediates may be isolated or purified using one or more standard purification techniques, including, for example, one or more of simple solvent evaporation, recrystallization, distillation, sublimation, filtration, chromatography, including thin-layer chromatography, HPLC (e.g., reverse phase HPLC using, for example, dilute trifluoroacetic acid in water, acetonitrile, or methanol mixtures as eluent), column chromatography, flash chromatography, radial chromatography, trituration, and the like.

In the preparation of the compounds of the invention, one skilled in the art will understand that one may need to protect or block various reactive functionalities on the starting compounds or intermediates while a desired reaction is carried out on other portions of the molecule. After the desired reactions are complete, or at any desired time, normally such protecting groups will be removed by, for example, hydrolytic or hydrogenolytic means. Such protection and deprotection steps are conventional in organic chemistry. One skilled in the art is referred to "Protective Groups in Organic Chemistry," McOmie, Ed., Plenum Press, New York, N.Y.; and "Protective Groups in Organic Synthesis," Greene, Ed., John Wiley & Sons, New York, N.Y. (1981) for the teaching of protective groups which may be useful in the preparation of compounds of the present invention.

Alternate means beyond those described above for preparing the compounds of the invention will be apparent to one skilled in the art and the noted general procedures are not to be construed as limiting the invention. To more fully understand the invention, including methods of preparing compounds of the invention, the following non-limiting examples are provided. The reader will appreciate that starting materials not otherwise described herein are either available commercially or can be prepared from commercially available compounds by methods generally known in the art.

Unless otherwise noted, all materials were obtained from commercial suppliers and used without further purification. Anhydrous solvents such as dimethylformamide (DMF), tetrahydrofuran (THF), dichloromethane ($CH_2Cl_2$), and toluene, dioxane were obtained from Aldrich Chemical Company in Sure/Seal bottles. All reactions involving air- or moisture-sensitive compounds were performed under a $N_2$ atmosphere. Flash chromatography was performed using ICN Biomedicals (SiliTech 32-63D 60A). Thin-layer chromatography (TLC) was performed with Analtech or Whatman silica gel TLC plates (250 μm). Preparatory TLC was performed with Whatman silica gel TLC plates (2000 μm). $^1$H NMR spectra were determined with superconducting FT NMR spectrometers operating at 400 and 500 MHz. Chemical shifts are expressed in ppm downfield from internal tetramethylsilane. Significant $^1$H NMR data are reported in the following order: multiplicity (s, singlet; d, doublet; t, triplet; q, quartet; m, multiplet; quin, quintet), number of protons, and coupling constants in Hz. Elemental analyses were performed by Atlantic Microlab, Inc., Norcross, GA. Melting points were determined with a Buchi 535 capillary melting point apparatus and are uncorrected. Low resolution mass spectra (MS) were determined on a Perkin Elmer-SCIEX API 165 mass spectrometer using APCI or ES ionization modes (positive or negative). High resolution mass spectra (HRMS) were performed by Mass Consortium, San Diego, Calif. using FAB ionization.

EXAMPLE 1

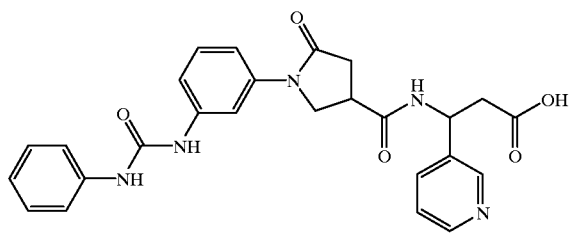

Preparation of sodium 3-((5-oxo-1-{3-((N-phenylcarbamoyl)amino)phenyl}pyrrolidin-3-yl)carbonylamino)-3-(3-pyridyl)propanoate Step A: ethyl 3-((5-oxo-1-{3-((N-phenylcarbamoyl)amino)phenyl}pyrrolidin-3-yl)carbonylamino)-3-(3-pyridyl)propanoate A solution of ethyl 3-{(1-(3-aminophenyl)-5-oxopyrrolidin-3-yl)carbonylamino}-3-(3-pyridyl)propanoate (80 mg, 0.20 mmol, 1.0 eq) and phenylisocyanate (Aldrich, 44 μL, 2.0 eq) in $CH_2Cl_2$ (1 mL) was stirred at room temperature for two days. The reaction mixture was washed with saturated sodium bicarbonate twice. The organic phase was dried, concentrated on rotary evaporator. Preparative TLC in 5% MeOH in $CH_2Cl_2$ afforded the title compound as an off-white solid. MS (ES+): 516 (M+H)$^+$; (ES−): 514 (M−H)$^−$.

Step B: Sodium 3-((5-oxo-1-{3-((N-phenylcarbamoyl)amino)phenyl}pyrrolidin-3-yl)carbonylamino)-3-(3-pyridyl)propanoate A solution of ethyl 3-((5-oxo-1-{3-((N-phenylcarbamoyl)amino)phenyl}pyrrolidin-3-yl)carbonylamino)-3-(3-pyridyl)propanoate (75 mg, 0.14 mmol, 1.0 eq), THF (1.0 mL), and 1.0 N NaOH (0.15 mL, 1.1 eq) was stirred at room temperature overnight. The solvent was removed on rotary evaporator. The title compound was obtained as an off-white solid. $^1$H NMR (MeOH-d$_4$, 400 MHz): δ 2.77 (m, 4), 3.30 (m, 1, overlap with solvent), 4.08 (m, 2), 5.35 (m, 1), 7.01(m, 2), 7.28 (m, 4), 7.41(m, 3), 7.66 (m, 1), 7.86 (m, 1), 8.39 (m, 1), 8.57 (m, 1). MS (ES+): 488 (M+H)$^+$; (ES−): 486 (M−H)$^−$.

EXAMPLE 2

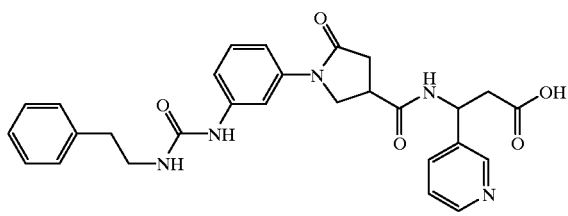

3-{(5-oxo-1-(3-{(N-(2-phenylethyl)carbamoyl)amino}phenyl)pyrrolidin-3-yl)carbonylamino]-3-(3-pyridyl)propanoic acid The title compound was analogously synthesized by the method described in Example 1 from 2-phenylethyl isocyanate. This compound was obtained as an off-white solid. $^1$H NMR (MeOH-d$_4$, 400 MHz): δ 2.83 (m, 4), 3.00 (t, 2), 3.35 (m, 1), 3.43 (t, 2), 4.00 (m, 2), 5.42 (m, 1), 7.09 (m, 1), 7.27 (m, 7), 7.67 (m, 1), 7.84 (m, 1), 8.36 (d, 1, J=8 Hz), 8.64 (t, 1), 8.79 (s, 1). MS (ES+): 516 (M+H)$^+$; (ES−): 514 (M−H)$^−$.

EXAMPLE 3

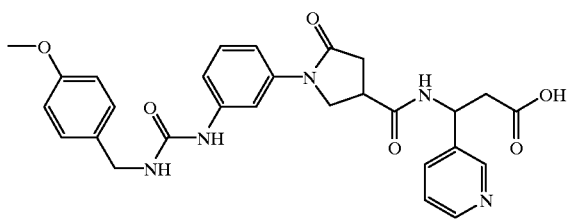

3-({1-[3-({N-((4-methoxyphenyl)methyl)carbamoyl}amino)phenyl)-5-oxopyrrolidin-3-yl}carbonylamino)-3-(3-pyridyl)propanoic acid The title compound was analogously synthesized by the method described in Example 1 from (4-methoxyphenyl)methylisocyanate. This compound was obtained as an off-white solid. $^1$H NMR (MeOH-d$_4$, 400 MHz): δ 2.65–2.86 (m, 4), 3.37 (m, 1), 3.76 (s, 3), 4.01 (m, 2), 4.30 (s, 2), 5.33 (m, 1), 6.87 (m, 2), 7.15–7.40 (m, 6), 7.56 (m, 1), 7.85 (m, 1), 8.38 (m, 1), 8.57 (s, 1). MS (ES+): 532 (M+H)$^+$; (ES−): 530 (M−H)$^−$.

EXAMPLE 4

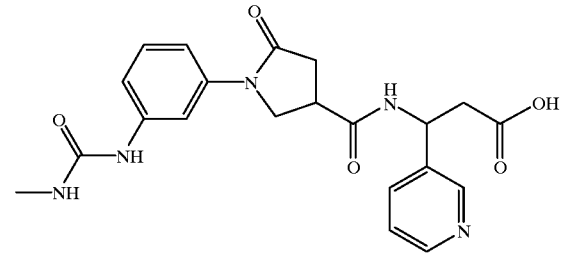

3-((1-3-((N-methylcarbamoyl)amino)phenyl}-5-oxopyrrolidin-3-yl)carbonylamino)-3-(3-pyridyl)pronanoic acid The title compound was analogously synthesized by the method described in Example 1 from methylisocyanate. This compound was obtained as a white solid. $^1$H NMR (MeOH-d$_4$, 400 MHz) : δ 2.69 (m, 3), 2.75 (m, 3), 2.81 (m, 1), 3.25–3.39 (m, 1, overlap with solvent), 4.05 (m, 2), 5.34 (m, 1), 7.15–7.40 (m, 4), 7.55 (s, 1), 7.86 (m, 1), 8.38 (m, 1), 8.57 (s, 1). MS (ES+): 426 (M+H)$^+$; (ES−): 424 (M−H)$^−$.

EXAMPLE 5

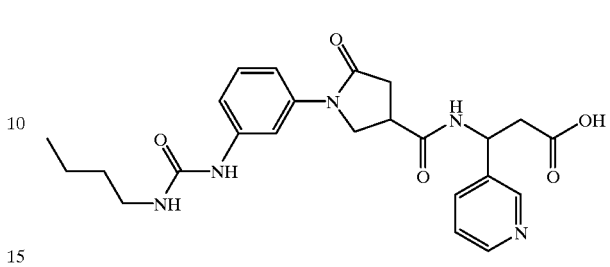

3-((1-{3-((N-butylcarbamoyl)amino)phenyl}-5-oxopyrrolidin-3-yl)carbonylamino)-3-(3-pyridyl)propanoic acid The title compound was analogously synthesized by the method described in Example 1 from butylisocyanate. This compound was obtained as a white solid. $^1$H NMR (MeOH-d$_4$, 400 MHz): δ 0.97 (t, 3), 1.42 (m, 2), 1.52 (m, 2), 2.68–2.89 (m, 4), 3.21 (m, 1), 4.07 (m, 2), 5.34 (m, 1), 7.17–7.42 (m, 4), 7.56 (m, 1), 7.88 (m, 1), 8.41 (m, 1), 8.58 (s, 1). MS (ES+): 468 (M+H)$^+$; (ES−): 466 (M−H)$^−$.

EXAMPLE 6

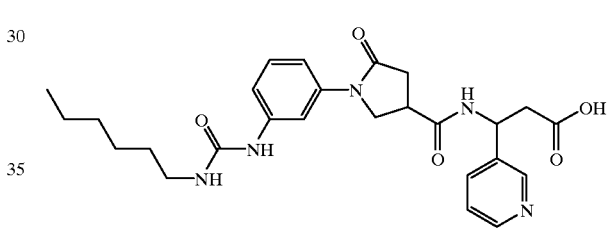

3-((1-{3-((N-hexylcarbamoyl)amino)phenyl}-5-oxopyrrolidin-3-yl)carbonylamino)-3-(3-pyridyl)propanoic acid The title compound was analogously synthesized by the method described in Example 1 from hexylisocyanate. This compound was obtained as a white solid. $^1$H NMR (MeOH-d$_4$, 400 MHz): δ 0.91 (t, 3), 1.34 (s, 6), 1.50 (m, 2), 2.65–2.86 (m, 4), 3.17 (m, 2), 3.35 (m, 1), 4.04 (m, 2), 5.34 (m, 1), 7.14–7.41 (m, 4), 7.54 (m, 1), 7.85 (m, 1), 8.38 (m, 1), 8.57 (S, 1). MS (ES+): 496 (M+H)$^+$; (ES−): 494 (M−H)$^−$.

EXAMPLE 7

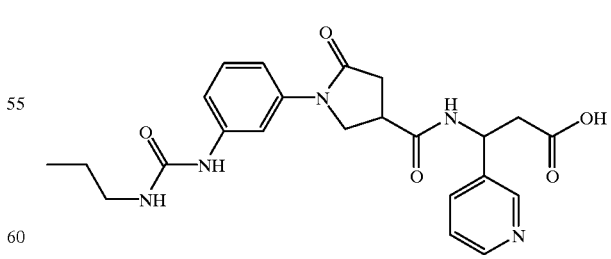

3-((5-oxo-1-{3-((N-propylcarbamoyl)amino)phenyl}pyrrolidin-3-yl)carbonylamino)-3-(3-pyridyl)propanoic acid The title compound was analogously synthesized by the method described in Example 1 from propylisocyanate. This compound was obtained as an off-white solid. $^1$H NMR (MeOH-d$_4$, 400 MHz): δ 0.94 (t, 3), 1.53 (m, 2), 2.65–2.86 (m, 4), 3.13 (m, 2), 3.36 (m, 1), 4.00 (m, 2), 5.34 (m, 1), 7.14–7.29 (m, 3), 7.38 (m, 1), 7.56 (m, 1), 7.85 (m, 1), 8.38 (m, 1), 8.57 (s, 1). MS (ES+): 454 (M+H)$^+$; (ES−): 452 (M−H)$^-$.

EXAMPLE 8

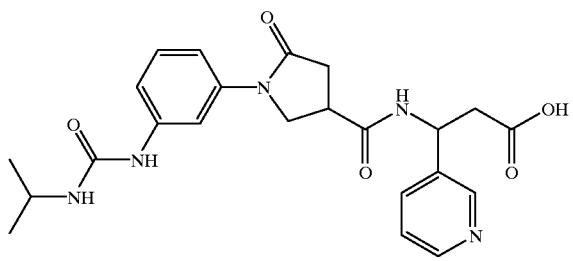

3-{ (1-(3-{(N-(1-methylethyl)carbamoyl)amino}phenyl)-5-oxopyrrolidin-3-yl)carbonylamino}-3-(3-pyridyl)protanoic acid The title compound was analogously synthesized by the method described in Example 1 from 2-propylisocyanate. This compound was obtained as an off-white solid. $^1$H NMR (MeOH-d$_4$, 400 MHz): δ 1.17 (d, 6), 2.70–2.84 (m, 2), 2.98 (m, 2), 3.34 (m, 1), 3.90 (m, 1), 4.05 (m, 2), 5.42 (m, 1), 7.11 (m, 1), 7.26 (m, 2), 7.67 (d, 1), 7.85 (m, 1), 8.37 (m, 1), 8.65 (m, 1), 8.79 (s, 1). MS (ES+) 454 (M+H)$^+$; (ES−): 452 (M−H)$^-$.

EXAMPLE 9

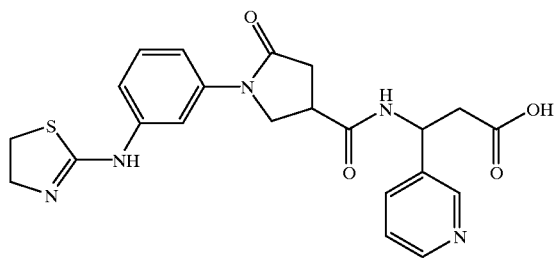

Preparation of 3-({5-oxo-1-(3-(1,3-thiazolin-2-ylamino)phenyl)pyrrolidin-3-yl}carbonylamino)-3-(3-pyridyl)propanoic acid Step A: ethyl 3-({5-oxo-1-(3-(1,3-thiazolin-2-ylamino)phenyl)pyrrolidin-3-yl}carbonylamino)-3-(3-pyridyl)propanoate A solution of ethyl 3-{(1-(3-aminophenyl)-5-oxopyrrolidin-3-yl)carbonylamino}-3-(3-pyridyl)propanoate (100 mg, 0.25 mmol, 1.0 eq), 2-methylthio-1,3-thiazoline (67 μL, 2.0 eq), and dioxane (1 mL) was heated at reflux temperature overnight. The solvent was removed on rotary evaporator. The product was obtained as a yellow solid from preparative TLC in 10% MeOH-CH$_2$Cl$_2$. MS (ES+): 482 (M+H)$^+$.

Step B: 3-({5-oxo-1-(3-(1,3-thiazolin-2-ylamino)phenyl)pyrrolidin-3-yl}carbonylamino)-3-(3-pyridyl)propanoic acid A solution of ethyl 3-({5-oxo-1-(3-(1,3-thiazolin-2-ylamino)phenyl)pyrrolidin-3-yl}carbonylamino)-3-(3-pyridyl)propanoate (75 mg, 0.16 mmol, 1.0 eq), THF (1.0 mL), and 1.0 N NaOH (0.16 mL, 1.0 eq) was stirred at room temperature overnight. The solvent was removed on rotary evaporator. The title compound was abstained as an off-white solid from preparative HPLC. $^1$H NMR (MeOH-d$_4$, 400 MHz): δ 2.68–2.99 (m, 4), 3.35 (m, 1), 3.67 (m, 2), 4.05 (m, 4), 5.42 (m, 1), 7.16 (m, 1), 7.52 (m, 2), 7.78 (m, 1), 7.88 (s, 1), 8.28 (m, 1), 8.62 (m, 1), 8.75 (m, 1). MS (ES+): 455 (M+H)$^+$; (ES−): 453 (M−H)$^-$.

EXAMPLE 10

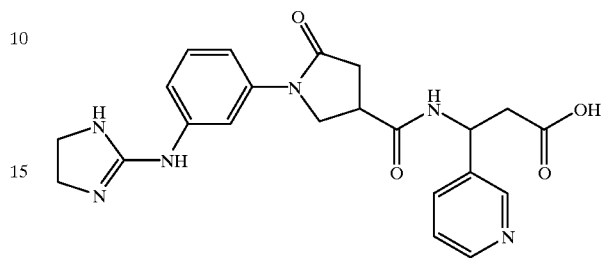

3-({1-(3-(2-imidazolin-2-ylamino)phenyl)-5-oxopyrrolidin-3-yl}carbonylamino)-3-(3-pyridyl)propanoic acid The title compound was analogously synthesized by the method described in Example 9 from 2-methylthio-2-imidazoline. This compound was obtained as an off-white solid. $^1$H NMR (MeOH-d$_4$, 400 MHz): δ 2.73–3.02 (m, 5), 3.34 (m, 4), 4.10 (m, 2), 5.47 (m, 1), 7.13 (m, 1), 7.50 (m, 2), 7.75 (m, 2), 8.29 (m, 1), 8.64 (m, 1), 8.78 (s, 1). MS (ES+): 437 (M+H)$^+$; (ES−): 435 (M−H)$^-$.

EXAMPLE 11

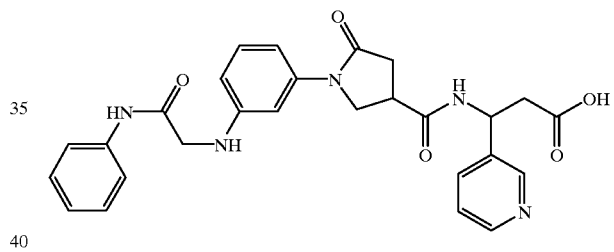

Preparation of 3-{(5-oxo-1-(3-{((N-phenylcarbamoyl)methyl)amino}phenyl)pyrrolidin-3-yl}carbonylamino}-3-(3-pyridyl)propanoic acid Step A: 2-bromo-N-phenylacetamide To a solution of 2-bromoacetyl chloride (Sigma, 0.89 g, 5.37 mmol, 1.0 eq), triethylamine (Aldrich, 0.54 g, 5.37 mmol, 1.0 eq), and CH$_2$Cl$_2$ (15 mL) in ice bath, was added aniline (Aldrich, 0.49 ml, 5.37 mmol, 1.0 eq). The mixture was warmed to room temperature and stirred overnight. The mixture was filtered, and the solvent was removed. The product was obtained as white solid from flash chromatography (15% EtOAc in hexane). MS (ES+): 216 (M+H)$^+$; (ES−): 214 (M−H)$^-$.

Step B: ethyl 3-{(5-oxo-1-(3-{((N-phenylcarbamoyl)methyl)amino}phenyl)pyrrolidin-3-yl)carbonylamino}-3-(3-pyridyl)propanoate To a suspension of ethyl 3-{(1-(3-aminophenyl)-5-oxopyrrolidin-3-yl)carbonylamino}-3-(3-pyridyl)propanoate (100 mg, 0.25 mmol, 1.1 eq), NaHCO$_3$ (20 mg, 0.23 mmol, 1.0 eq), and CH$_2$Cl$_2$ (4 mL), was added 2-bromo-N-phenyl acetamide (50 mg, 0.23 mmol, 1.0 eq) in 2 mL CH$_2$Cl$_2$ dropwise. The reaction mixture was heated up to reflux for 5 hours, then cooled to room temperature. The solid was filtered and the solvent was removed. Preparative TLC (5% MeOH-CH$_2$Cl$_2$) afforded the product as colorless oil. MS (ES+): 530 (M+H)$^+$; (ES−): 528 (M−H)$^-$.

Step C: 3-{(5-oxo-1-(3-{((N-phenylcarbamoyl)methyl)amino}phenyl)pyrrolidin-3-yl)carbonylamino}-3-(3-pyridyl)propanoic acid The title compound was analogously synthesized by the method described in step B of Example 9 from ethyl 3-{(5-oxo-1-(3-{((N-phenylcarbamoyl)methyl)amino}phenyl)pyrrolidin-3-yl)carbonylamino}-3-(3-pyridyl)propanoate as an off-white solid. $^1$H NMR (MeOH-d$_4$, 400 MHz): δ 2.70–2.99 (m, 4), 3.87–4.08 (m, 5), 5.41 (m, 1), 6.51 (m, 1), 6.81 (m, 1), 6.98 (m, 1), 7.12 (m, 2), 7.29 (m, 2), 7.53 (m, 2), 7.83 (m, 1), 8.34 (m, 1), 8.64 (m, 1), 8.77 (s, 1). MS (ES+): 502 (M+H)$^+$; (ES−): 500 (M−H)$^-$.

EXAMPLE 12

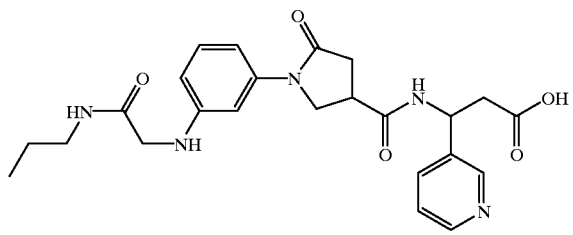

3-{(5-oxo-1-(3-{((N-propylcarbamoyl)methyl)amino}phenyl)pyrrolidin-3-yl)carbonylamino}-3-(3-pyridyl)propanoic acid The title compound was analogously synthesized by the method described in Example 11 from propylamine. This compound was obtained as an off-white solid. $^1$H NMR (MeOH-d$_4$, 400 MHz): δ 0.84 (m, 3), 1.48 (m, 2), 2.74–2.97 (m, 5), 3.16 (m, 2), 3.73 (d, 2), 4.00 (m, 2), 5.40 (m, 1), 6.44 (m, 1), 6.81 (m, 1), 6.89 (m, 1), 7.14 (m, 1), 7.66 (m, 2), 8.14 (m, 1), 8.57 (m, 1), 8.69 (s, 1). MS (ES+): 468 (M+H)$^+$; (ES−): 466 (M−H)$^-$.

EXAMPLE 13

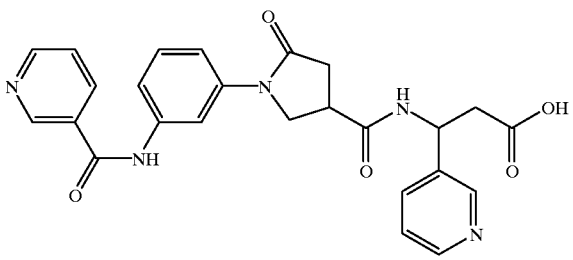

Preparation of 3-({5-oxo-1-(3-(3-pyridylcarbonylamino)phenyl)pyrrolidin-3-yl}carbonylamino)-3-(3-pyridyl)propanoic acid
Step A: ethyl 3-({5-oxo-1-(3-(3-pyridylcarbonylamino)phenyl)pyrrolidin-3-yl}carbonylamino)-3-(3-pyridyl)propanoate To a solution of ethyl 3-{(1-(3-aminophenyl)-5-oxopyrrolidin-3-yl)carbonylamino}-3-(3-pyridyl)propanoate (50 mg, 0.12 mmol, 1.0 eq), triethylamine (40 μL, 0.24 mmol, 2.0 eq), and CH$_2$Cl$_2$ (1.5 mL), was added pyridine-3-carbonyl chloride hydrochloride (Aldrich, 35 mg, 0.18 mmol, 1.5 eq). The reaction mixture was stirred at room temperature for 24 hours, then washed with 5% Na$_2$CO$_3$ solution. The organic phase was dried over Na$_2$SO$_4$. The solvent was removed and the crude product was purified by preparative TLC (10% MeOH in CH$_2$Cl$_2$). The title compound was obtained as a light yellow solid. MS (ES+): 502 (M+H)$^+$; (ES−): 500 (M−H)$^-$.

Step B: 3-({5-oxo-1-(3-(3-pyridylcarbonylamino)phenyl)pyrrolidin-3-yl}carbonylamino)-3-(3-pyridyl)propanoic acid The title compound was analogously synthesized by the method described in Example 1 step B from ethyl 3-({5-oxo-1-(3-(3-pyridylcarbonylamino)phenyl)pyrrolidin-3-yl}carbonylamino)-3-(3-pyridyl)propanoate as an off-white solid. $^1$H NMR (MeOH-d$_4$, 400 MHz): δ 2.75–3.02 (m, 4), 3.39 (m, 1), 3.93–4.19 (m, 2), 5.43 (m, 1), 7.28–7.44 (m, 3), 7.53 (m, 1), 7.88–8.09 (m, 4), 8.47 (m, 1), 8.70 (m, 1), 8.79 (m, 1), 8.84 (s, 1). MS (ES+): 474 (M+H)$^+$; (ES−): 472 (M−H)$^-$.

EXAMPLE 14

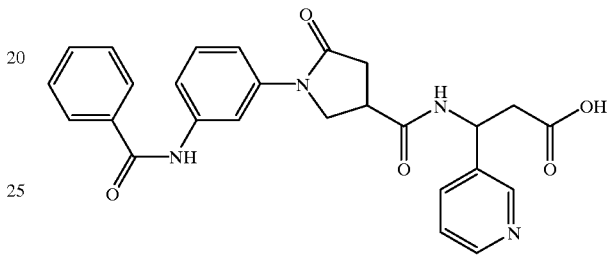

3-({5-oxo-1-(3-(phenylcarbonylamino)phenyl)pyrrolidin-3-yl}carbonylamino)-3-(3-pyridyl)propanoic acid The title compound was analogously synthesized by the method described in Example 13 from benzoyl chloride. This compound was obtained as an off-white solid. $^1$H NMR (MeOH-d$_4$, 400 MHz): δ 2.65–2.89 (m, 4), 3.41 (m, 1), 3.91–4.16 (m, 2), 5.34 (m, 1), 7.31–7.66 (m, 7), 7.85–7.95 (m, 4), 8.39 (m, 1), 8.55 (s, 1). MS (ES+): 473 (M+H)$^+$; (ES−): 471 (M−H)$^-$.

EXAMPLE 15

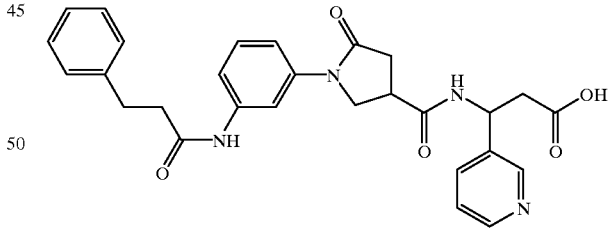

3-({5-oxo-1-(3-(3-phenylpropanoylamino)phenyl)pyrrolidin-3-yl}carbonylamino)-3-(3-pyridyl)propanoic acid The title compound was analogously synthesized by the method described in Example 13 from 3-phenylpropanoyl chloride. This compound was obtained as an off-white solid. $^1$H NMR (MeOH-d$_4$, 400 MHz): δ 2.63–2.87 (m, 6), 2.97 (m, 2), 3.37 (m, 1), 3.87–4.11 (m, 2), 5.34 (m, 1), 7.13–7.47 (m, 9), 7.72 (s, 1), 7.85 (m, 1), 8.39 (m, 1), 8.57 (m, 1). MS (ES+): 501 (M+H)$^+$; (ES−): 499 (M−H)$^-$.

EXAMPLE 16

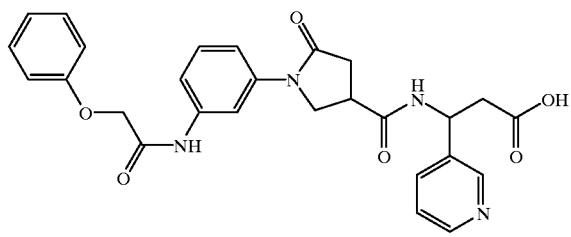

3-({5-oxo-1-(3-(2-phenoxyacetylamino)phenyl)pyrrolidin-3-yl}carbonylamino)-3-(3-pyridyl)propanoic acid The title compound was analogously synthesized by the method described in Example 13 from 2-phenoxyacetyl chloride. This compound was obtained as an off-white solid. $^1$H NMR (MeOH-d$_4$, 400 MHz): δ 2.65–2.87 (m, 4), 3.39 (m, 1), 3.90–4.11 (m, 2), 4.65 (m,2), 5.34 (m, 1), 6.86–7.06 (m, 3), 7.23 (m, 1), 7.33 (m, 4), 7.54 (m, 1), 7.85 (m, 2), 8.38 (m, 1), 8.57 (s, 1). MS (ES+): 503 (M+H)$^+$; (ES−): 501 (M−H)$^−$.

EXAMPLE 17

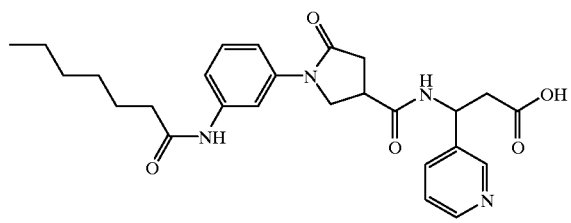

3-({1-(3-(heptanoylamino)phenyl)-5-oxopyrrolidin-3-yl}carbonylamino)-3-(3-pyridyl)propanoic acid The title compound was analogously synthesized by the method described in Example 13 from heptanoyl chloride. This compound was obtained as an off-white solid. MS (ES+): 481 (M+H)$^+$; (ES−): 479 (M−H)$^−$.

EXAMPLE 18

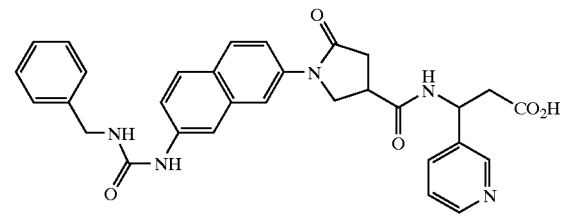

3-{(5-oxo-1-(7-{(benzylamino)carbonylamino}(2-naphthyl))pyrrolidin-3-yl)carbonylamino}-3-(3-pyridyl)propanoic acid The title compound was analogously synthesized by the method described in Example 1 from ethyl 3-{(1-(7-amino(2-naphthyl))-5-oxopyrrolidin-3-yl)carbonylamino}-3-(3-pyridyl)propanoate and phenylmethylisocyanate. This compound was obtained as a white solid. $^1$H NMR (MeOH-d$_4$, 400 MHz): δ 2.81–3.02 (m, 4), 3.41 (m, 1), 4.01–4.18 (m, 2), 4.43 (s, 2), 5.44 (m, 1), 7.28 (m, 1), 7.37 (m, 5), 7.78 (m, 4), 7.89 (m, 1), 7.99 (m, 1), 8.44 (m, 1), 8.68 (m, 1), 8.84 (s, 1). MS (ES+): 552 (M+H)$^+$; (ES−): 550 (M−H)$^−$.

EXAMPLE 19

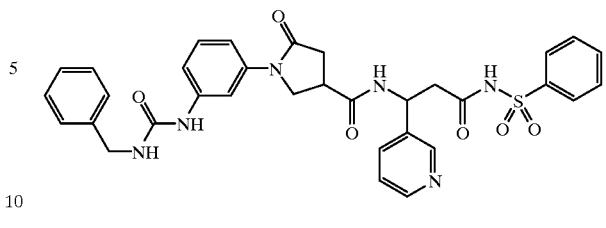

3-{(5-oxo-1-(3-{(benzylamino)carbonylamino}phenyl)pyrrolidin-3-yl)carbonylamino}-N-(phenylsulfonyl)-3-(3-pyridyl)propanamide A suspension of 3-{(5-oxo-1-(3-{(benzylamino)carbonylamino}phenyl)pyrrolidin-3-yl)carbonylamino}-3-(3-pyridyl)propanoic acid (60 mg, 0.11 mmol), benzenesulfonamide (Aldrich, 18 mg, 0.11 mmol), 1-ethyl-3-(3-(dimethylamino)propyl)carbodiimide hydrochloride (22 mg, 0.11 mmol), and dimethyl-4-pyridylamine (Aldrich, 0.22 mmol) in CH$_2$Cl$_2$ (5 mL) was stirred at room temperature for 2 days. A white solid was filtered and further purified by preparative HPLC. The title compound was obtained as a white solid. MS (ES+): 643 (M+H)$^+$; (ES−): 641 (M−H)$^−$.

EXAMPLE 20

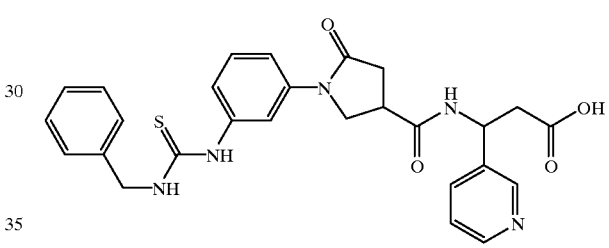

Preparation of 3-({5-oxo-1-(3-({(benzylamino)thioxomethyl}amino)phenyl)pyrrolidin-3-yl}carbonylamino)-3-(3-pyridyl)propanoic acid, sodium salt Step A: Ethyl 3-({5-oxo-1-(3-({(benzylamino)thioxomethyl}amino)phenyl)pyrrolidin-3-yl}carbonylamino)-3-(3-pyridyl)propanoate A solution of ethyl 3-{(1-(3-aminophenyl)-5-oxopyrrolidin-3-yl)carbonylamino}-3-(3-pyridyl) propanoate (100 mg, 0.25 mmol, 1.0 eq) and benzyl isothiocyanate (Aldrich, 188 mg, 1.26 mmol, 5.0 eq) in CH$_2$Cl$_2$ (2 mL) was stirred at room temperature for 72 hours. The reaction was quenched with tris(2-aminoethyl)amine, polymer-bound (Aldrich, 1 g) and the mixture was stirred at room temperature for 4 hours. After the filtration of polymer-bound reagent, the crude product was concentrated under reduced pressure. Preparative thin layer chromatography (5% MeOH-CH$_2$Cl$_2$) afforded the title compound as white sponge-like solid. MS (ES+): 546 (M+H)$^+$; (ES−): 544 (M−H)$^−$.

Step B: 3-({5-oxo-1-(3-({(benzylamino)thioxomethyl}amino)phenyl)pyrrolidin-3-yl}carbonylamino)-3-(3-pyridyl)propanoic acid, sodium salt A solution of ethyl 3-({5-oxo-1-(3-({(benzylamino)thioxomethyl}amino)phenyl)pyrrolidin-3-yl}carbonylamino)-3-(3-pyridyl)propanoate (114 mg, 0.21 mmol) in ethanol was added a solution of NaOH (0.115 mL, 2.0 M, 0.23 mmol, 1.1 eq). The reaction mixture was stirred at room temperature for 24 hours. The solvent was removed under reduced pressure. The title compound was obtained as white solid: Mp: 230° C. (dec.). MS (ES+): 540 (M+H)$^+$.

EXAMPLE 21

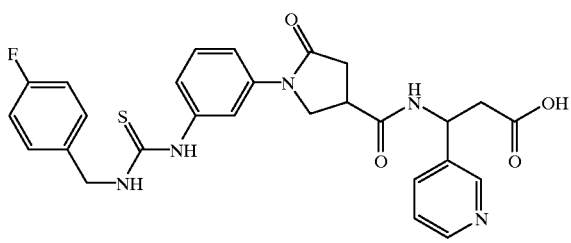

3-((1-{3-(({((4-fluorophenyl)methyl)amino}thioxomethyl)amino)phenyl}-5-oxopyrrolidin-3-yl)carbonylamino)-3-(3-pyridyl)propanoic acid, sodium salt The title compound was analogously synthesized by the method described in Example 20 from ethyl 3-{(1-(3-aminophenyl)-5-oxopyrrolidin-3-yl)carbonylamino}-3-(3-pyridyl)propanoate (100 mg, 0.25 mmol, 1.0 eq) and 4-fluorobenzyl isothiocyanate (Transworld, 1.26 mmol, 5.0 eq). The title compound was obtained as white solid. Mp: 230° C. (dec.). MS (ES+): 558 (M+H)+.

EXAMPLE 22

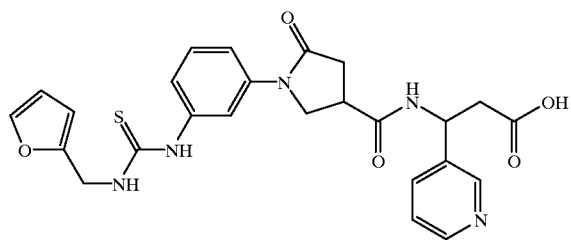

3-({1-(3-({((2-furylmethyl)amino)thioxomethyl}amino)phenyl)-5-oxopyrrolidin-3-yl}carbonylamino)-3-(3-pyridyl)propanoic acid, sodium salt The title compound was analogously synthesized by the method described in Example 20 from ethyl 3-{(1-(3-aminophenyl)-5-oxopyrrolidin-3-yl)carbonylamino}-3-(3-pyridyl)propanoate (100 mg, 0.25 mmol, 1.0 eq) and 2-furylmethyl isothiocyanate (Transworld, 1.26 mmol, 5.0 eq). The title compound was obtained as orange solid. Mp: 240° C. (dec.). MS (ES+): 530 (M+H)+.

EXAMPLE 23

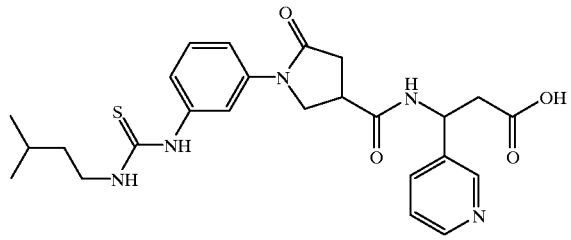

3-({1-(3-({((3-methylbutyl)amino)thiooxomethyl}amino)phenyl)-5-oxopyrroidin-3-yl}carbonylamino)-3-(3-pyridyl)propanoic acid, sodium salt The title compound was analogously synthesized by the method described in Example 20 from ethyl 3-{(1-(3-aminophenyl)-5-oxopyrrolidin-3-yl)carbonylamino}-3-(3-pyridyl)propanoate (100 mg, 0.25 mmol, 1.0 eq) and 3-methylbutyl isothiocyanate (Transworld, 1.26 mmol, 5.0 eq). The title compound was obtained as white solid. Mp: 250° C. (dec.). MS (ES+): 520 (M+H)+.

EXAMPLE 24

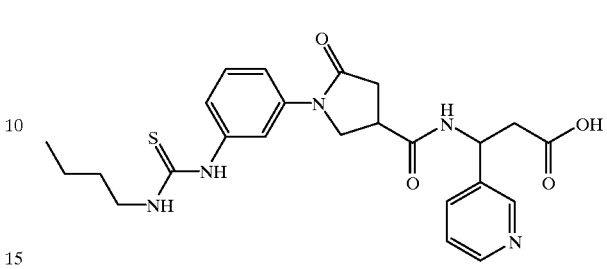

3-{(1-(3-{((butylamino)thioxomethyl)amino}phenyl)-5-oxopyrrolidin-3-yl)carbonylamino}-3-(3-pyridyl)propanoic acid, sodium salt The title compound was analogously synthesized by the method described in Example 20 from ethyl 3-{(1-(3-aminophenyl)-5-oxopyrrolidin-3-yl)carbonylamino}-3-(3-pyridyl)propanoate (100 mg, 0.25 mmol, 1.0 eq) and butyl isothiocyanate (Fluka, 1.26 mmol, 5.0 eq). The title compound was obtained as white solid. Mp: 235° C. (dec.). MS (ES+): 506 (M+H)+.

EXAMPLE 25

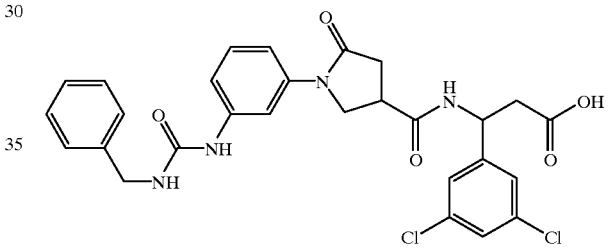

Preparation of 3-(3,5-Dichlorophenyl)-3-{(5-oxo-1-(3-{(benzylamino)carbonylamino}phenyl)pyrrolidin-3-yl)carbonylaminolyronanoic acid sodium salt Step A: methyl 3-(3,5-dichlorophenyl)-3-{(5-oxo-1-(3-{(benzylamino)carbonylamino}phenyl)pyrrolidin-3-yl)carbonylaminolpropanoate In a manner analogous to the preparation of methyl 3-(3-fluorophenyl)-3-{(5-oxo-1-(3-{(benzylamino)carbonylamino}phenyl)pyrrolidin-3-yl)carbonylamino}propanoate, the two diastereomers of the title compound (first diastereomer and second diastereomer) were prepared as white solids.

First diastereomer: $^1$H NMR (400 MHz, DMSO-$d_6$): δ 8.71 (d, 1H, J=8.1 Hz), 8.68 (s, 1H), 7.77 (s, 1H), 7.52 (t, 1H, J=1.8 Hz), 7.42 (d, 2H, J=1.8 Hz), 7.13–7.35 (m, 8H), 6.59 (t, 1H, J=5.9 Hz), 5.20 (dt, 1H, J=8.2 Hz, 6.5 Hz), 4.29 (d, 2H, J=5.9 Hz), 4.00 (t, 1H, J=9.2 Hz), 3.77 (dd, 1H, J=9.7 Hz, 5.6 Hz), 3.55 (s, 3H), 3.22–3.30 (m, 1H), 2.84 (ABX, 2H), 2.71 (dd, 1H, J=16.9 Hz, 9.3 Hz), 2.57 (dd, 1H, J=16.9 Hz, 6.6 Hz). MS: (−) 581.0 (M−H), 641.5, 643.5, 645.5 (9:6:1, M+OAc−).

Second diastereomer: $^1$H NMR (400 MHz, DMSO-$d_6$): δ 8.70 (d, 1H, J=8.1 Hz), 8.66 (s, 1H), 7.76 (s, 1H), 7.50 (t, 1H, J=1.8 Hz), 7.42 (d, 2H, J=1.8 Hz), 7.17–7.35 (m, 7H), 7.10 (d, 1H, J=8.2 Hz), 6.58 (t, 1H, J=5.9 Hz), 5.20 (td, 1H, J=8.2 Hz, 6.5 Hz), 4.29 (d, 2H, J=5.9 Hz), 3.94 (t, 1H, J=9.1 Hz), 3.78 (dd, 1H, J=9.6 Hz, 5.5 Hz), 3.58 (s, 3H), 3.23–3.31 (m, 1H), 2.85 (ABX, 2H), 2.78 (dd, 1H, J=17.0 Hz, 9.5 Hz), 2.57 (dd, 1H, J=17.0 Hz, 6.6 Hz). MS: (−) 581.0 (M−H), 641.5, 643.5, 645.5 (9:6:1, M+OAc⁻)

Step B: 3-(3.5-dichlorophenyl)-3-{(5-oxo-1-(3-{(benzylamino)carbonylamino}phenyl)pyrrolidin-3-yl) carbonylamino}propanoic acid, sodium salt In a manner analogous to the preparation of 3-(3-fluorophenyl)-3-{(5-oxo-1-(3-{(benzylamino) carbonylamino}phenyl)pyrrolidin-3-yl) carbonylamino}propanoic acid, sodium salt, the title compound was prepared, as an equimolar mixture of diastereomers, as a white solid. $^1$H NMR (400 MHz, DMSO-d$_6$): δ 9.92 (S, 1H), 9.79 (s, 1H), 9.31 (d, 1H, J=7.6 Hz), 9.27 (d, 1H, J=7.7 Hz), 8.03 (br t, 1H), 7.88 (br t, 1H), 7.69 (s, 1H), 7.58 (s, 1H), 7.47–7.49 (m, 1H), 7.03–7.39 (m, 25H), 5.04–5.10 (m, 2H), 4.23–4.26 (m, 4H), 3.89–3.96 (m, 2H), 3.82–3.86 (m, 2H), 3.42–3.45 (m, 1H), 2.50–2.78 (m, 8H). MS: (−) 567.0 (M−H).

EXAMPLE 26

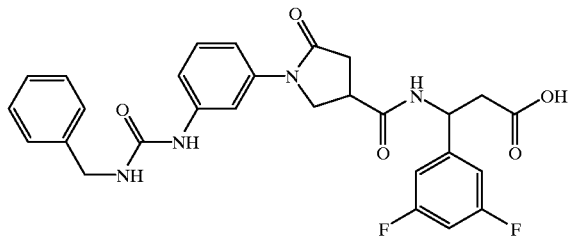

Preparation of 3-(3,5-difluorophenyl)-3-{(5-oxo-1-(3-{(benzylamino)carbonylamino}phenyl)pyrrolidin-3-yl) carbonylamino}prooanoic acid, sodium salt Step A: methyl 3-(3,5-difluorophenyl)-3-{(5-oxo-1-(3-{(benzylamino)carbonylamino}phenyl)pyrrolidin-3-yl) carbonylamino}propanoate In a manner analogous to the preparation of methyl 3-(3-fluorophenyl)-3-{(5-oxo-1-(3-{(benzylamino) carbonylamino}phenyl)pyrrolidin-3-yl) carbonylamino}propanoate, the two diastereomers of the title compound (first diastereomer and second diastereomer) were prepared as white solids.

First diastereomer: $^1$H NMR (400 MHz, DMSO-d$_6$): δ 8.70 (d, 1 H J=8.2 Hz), 8.68 (s, 1H), 7.77 (s, 1H), 7.04–7.35 (m, 12H), 6.59 (t, 1H, J=5.9 Hz), 5.21–5.27 (m, 1H), 4.29 (d, 2H, J=5.8 Hz), 4.00 (t, 1H, J=9.2 Hz), 3.77 (dd, 1H, J=9.7 Hz, 5.6 Hz), 3.55 (s, 3H), 3.22–3.27 (m, 1H), 2.67–2.89 (m, 3H), 2.59 (dd, 1H, J=17.0 Hz, 6.7 Hz). MS: (+) 568.5 (M+NH$_4$⁺); (−) 549.0 (M−H).

Second diastereomer: $^1$H NMR (400 MHz, DMSO-d$_6$): δ 8.69 (d, 1H, J=8.1 Hz), 8.66 (s, 1H), 7.76 (t, 1H, J=1.8 Hz), 7.08–7.35 (m, 11H), 6.58 (t, 1H, J=5.9 Hz), 5.24 (m, 1H), 4.29 (d, 2H, J=5.9 Hz), 3.95 (t, 1H, J=9.1 Hz), 3.79 (dd, 1H, J=9.7 Hz, 5.6 Hz), 3.59 (s, 3H), 3.22–3.30 (m, 1H), 2,72–2.87 (m, 3H), 2.57 (dd, 1H, J=17.0 Hz, 6.6 Hz). MS: (+) 568.5 (M+NH⁺); (−) 609.5 (M+OAc⁻).

Step B: 3-(3,5-Difluorophenyl)-3-{(5-oxo-1-(3-{(benzylamino)carbonylamino}phenyl)pyrrolidin-3-yl) carbonylamino}propanoic acid, sodium salt In a manner analogous to the preparation of 3-(3-fluorophenyl)-3-{(5-oxo-1-(3-{(benzylamino) carbonylamino}phenyl)pyrrolidin-3-yl) carbonylamino}propanoic acid, sodium salt, the title compound was prepared, as an equimolar mixture of diastereomers, as a white solid. $^1$H NMR (400 MHz, DMSO-d$_6$): δ 9.97 (d, 1H, J=6.6 Hz), 9.90 (s, 1H), 9.24–9.29 (m, 2H), 8.09 (m, 1H), 8.02 (m, 1H), 7.71 (s, 1H), 7.60 (m, 1H), 7.49 (d, 1H, J=7.4 Hz), 7.39 (d, 1H, J=8.0 Hz), 6.95–7.31 (m, 20H), 5.09–5.11 (m, 2H), 4.23–4.25 (m, 4H), 3.81–3.96 (m, 4H), 2.55–2.77 (m, 4H), 2.34–2.40 (m, 4H). MS: (+) 537.5 (M+H).

EXAMPLE 27

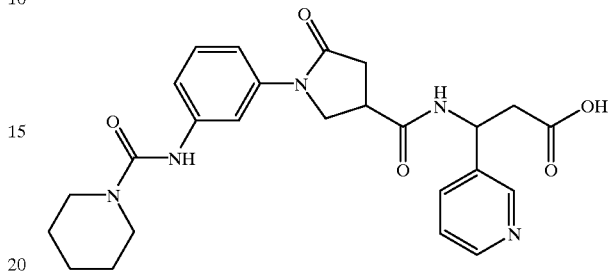

Preparation of 3-({5-oxo-1-(3-(piperidylcarbonylamino) phenyl)pyrrolidin-3-yl}carbonylamino)-3-(3-pyridyl) propanoic acid Step A: Ethyl 3-({5-oxo-1-(3-(piperidylcarbonylamino) phenyl)pyrrolidin-3-yl}carbonylamino)-3-(3-pyridyl) propanoate A solution of ethyl 3-{(1-(3-aminophenyl)-5-oxopyrrolidin-3-yl)carbonylamino}-3-(3-pyridyl) propanoate (200 mg, 0.51 mmol, 1.0 eq) and 1-((2,5-dioxopyrrolidinyl)carbonyl)pyrrolidine-2,5-dione (Aldrich, 194 mg, 0.76 mmol, 1.5 eq) in DMF (3 mL) was stirred at room temperature overnight. Piperidine (215 mg, 2.53 mmol, 5.0 eq) was added and the white precipitate was formed immediately. After removal of solvent, column chromatograpy (0–7% MeOH-CH$_2$Cl$_2$) afforded the title compound as a white solid. MS (ES+): 508 (M+H)⁺; (ES−): 506 (M−H)⁻.

Step B: 3-({5-oxo-1-(3-(piperidylcarbonylamino)phenyl) pyrrolidin-3-yl}carbonylamino)-3-(3-pyridyl)propanoic acid To a solution of ethyl 3-({5-oxo-1-(3-(piperidylcarbonylamino)phenyl)pyrrolidin-3-yl}carbonylamino)-3-(3-pyridyl)propanoate (169 mg, 0.333 mmol, 1.0 eq) was added a solution of NaOH (0.84 mL, 2.0 M, 1.67 mmol, 5.0 eq). After the reaction mixture was stirred at room temperature overnight, it was neutralized with a solution of aqueous HCl (0.84 mL, 2.0 M, 1.67 mmol). Following removal of solvent under reduced pressure, product was dissolved in 10% MeOH-CH$_2$Cl$_2$, and filtered. Concentration under reduced pressure afforded the title compound as an orange solid. $^1$H NMR (DMSO-d6, 400 MHz): δ 1.47 (m, 4), 1.56 (m, 2), 2.56–2.77 (m, 2), 2.82 (m, 2), 3.29 (m, 5), 3.73–3.83 (m, 1), 3.91–4.01 (m, 1), 5.25 (m, 1), 7.19 (m, 1), 7.28 (m, 1), 7.55 (m, 1), 7.70 (d, 1 J =12.5), 7.96 (d, 1, J =7.9), 8.50 (d, 1, J=8.7), 8.55 (m, 1), 8.65 (s, 1), 8.82 (d, 1, J=7.8), 12.4 (br s, 1). MS (ES+): 480 (M+H)⁺; (ES−) 478 (M−H)⁻.

EXAMPLE 28

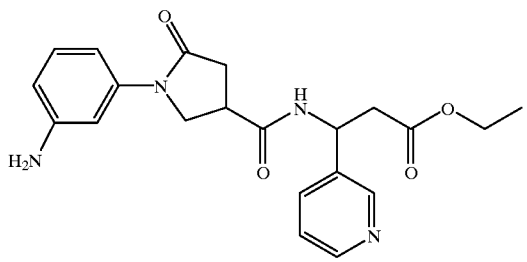

Preparation of Ethyl 3-{(1-(3-aminophenyl)-5-oxopyrrolidin-3-yl)carbonylamino}-3-(3-pyridyl)propanoate Step A: 1-(3-nitrophenyl)-5-oxopyrrolidine-3-carboxylic acid A mixture of itaconic acid (13.1 g, 0.1 mol) and 3-nitroaniline (13.8 g, 0.1 mol) was heated to 110° C. for 18 hours. The resulting solid was dissolved in 1N NaOH solution (200 mL). Undissolved solid was removed with filtration and the aqueous solution was acidified with 10% HCl to about pH 1. A yellow precipitate was collected, washed with cold water, and dried in vacuo at 50° C. The desired product was obtained as yellow solid. MS (ES+): 251.5 (M+H)$^+$.

Step B: Ethyl 3-{(1-(3-nitrophenyl)-5-oxopyrrolidin-3-yl)carbonylamino}-3-(3-pyridyl)propanoate To a mixture of 1-(3-nitrophenyl)-5-oxopyrrolidine-3-carboxylic acid (5 g, 0.02 mol), ethyl 3-amino-3-pyridylpropanoate (HCl salt) (0.03 mol) and HOAt (0.02 mol) in DMF (80 mL) at 0° C. was added i-Pr$_2$NEt (0.03 mol), followed by 1-(3-dimethylaminopropyl)-3-ethyl carbodiimide hydrochloride (EDCI) (0.04 mol), in portions. The reaction mixture was then warmed up to room temperature and stirred overnight. The reaction solution was diluted with EtOAc (150 mL) and the organic phase was washed with saturated NaHCO$_3$ and NaCl aqueous solution. The organic layer was dried over Na$_2$SO$_4$, concentrated in vacuo. The crude product was purified by flash column with 10% MeOH/EtOAc as eluent. Yellow solid was obtained. MS (ES+): 427.5 (M+H)$^+$.

Step C: Ethyl 3-{(1-(3-aminophenyl)-5-oxopyrrolidin-3-yl)carbonylamino}-3-(3-pyridyl)propanoate Ethyl 3-{(1-(3-nitrophenyl)-5-oxopyrrolidin-3-yl)carbonylamino}-3-(3-pyridyl)propanoate was dissolved in THF/MeOH/H$_2$O solution at 0° C. AcOH was added followed by activated Zn powder. The reaction was then stirred at room temperature for 5 hours. The Zn powder was filtered through a pad of celite. The filtrate was concentrated in vacuo and the residue was re-dissolved in EtOAc. A white precipitate formed and was removed by filtration. The organic solution was concentrated in vacuo to afforded yellow foam. MS (ES+): 397.0 (M+H)$^+$.

EXAMPLE 29

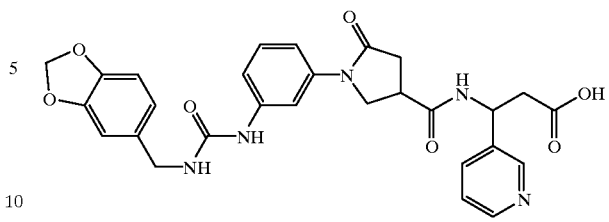

Preparation of 3-{(1-{3-((N-(1,3-benzodioxol-5-ylmethyl)aminocarbonyl)amino)phenyl}-5-oxooyrrolidin-3-yl)carbonylamino}-3-(3-pyridyl)propanoic acid, sodium salt Step A: ethyl 3-{(1-{3-((N-(1,3-benzodioxol-5-ylmethyl)aminocarbonyl)amino)phenyl}-5-oxo-pyrolidin-3-yl)carbonylamino}-3-(3-pyridyl)propanoate To a solution of ethyl 3-{(1-(3-aminophenyl)-5-oxopyrrolidin-3-yl)carbonylamino}-3-(3-pyridyl)propanoate in THF/DMF (5:2) was added N,N'-disuccinimidyl carbonate (2 eq.). The reaction was allowed to stir for 10 hours. (1,3-Benzodioxol-5-ylmethyl)amine (6 eq.) was added to the reaction mixture. After 5 hours, the reaction mixture was diluted with EtOAc, and the resulting solution was washed with saturated NaHCO$_3$ and brine solution. The organic layer was dried over Na$_2$SO$_4$ and concentrated in vacuo. The crude product was purified by flash chromatography with 10% MeOH/EtOAc provide a yellow solid. MS (ES+): 574.5 (M+H)$^+$.

Step B: 3-{(1-{3-((N-(1,3-benzodioxol-5-ylmethyl)aminocarbonyl)amino)phenyl}-5-oxopyrrolidin-3-yl)carbonylamino}-3-(3-pyridyl)prooanoic acid, sodium salt To a solution of ethyl 3-{(1-{3-((N-(1,3-benzodioxol-5-ylmethyl)aminocarbonyl)amino)phenyl}-5-oxopyrrolidin-3-yl)carbonylamino}-3-(3-pyridyl)propanoate in water/THF/MeOH was added 1.0 eq 1 N NaOH. The volume ratio of NaOH/water/THF/MeOH was 1:3:4:4. The reaction was stirred at room temperature overnight, and then concentrated in vacuo. The residue was dissolved in 5% MeOH/CH$_2$Cl$_2$. After removing the non-soluble material by filtration, the solution was concentrated in vacuo to provide a light yellow solid. MS (ES+): 568.5 (M+Na)$^+$.

EXAMPLE 30

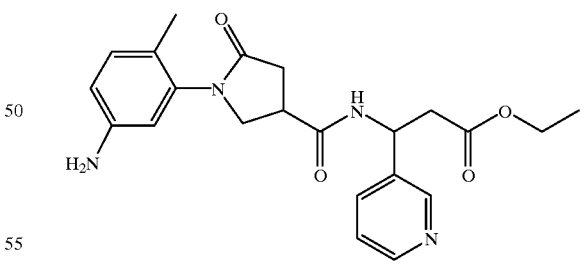

Preparation of ethyl 3-{(1-(2-methyl-5-aminophenyl)-5-oxopyrrolidin-3-yl)carbonylamino}-3-(3-pyridyl)propanoate Step A: 1-(2-methyl-5-nitrophenyl)-5-oxopyrrolidine-3-carboxylic acid A mixture of itaconic acid (30.40 g, 0.2 mol) and 2-methyl-5-nitroaniline (26.02 g, 0.2 mol) was heated to 110° C. for 18 hours. The resulted solid was dissolved in 1N NaOH solution (400 mL). Undissolved solid was removed with filtration and the aqueous solution was acidified with 10% HCl solution to about pH 1. A yellow precipitate was collected, washed with cold water, and dried in vacuo at 50° C. The desired product was obtained as yellow solid. MS (ES+): 265.0 (M+H)+.

Step B: Ethyl 3-{(1-(2-methyl-5-nitrophenyl)-5-oxopyrrolidin-3-yl)carbonylamino}-3-(3-pyridyl)propanoate To a mixture of 1-(2-methyl-5-nitrophenyl)-5-oxopyrrolidine-3-carboxylic acid (5 g), ethyl 3-amino-3-pyridylpropanoate and HOAt in DMF at 0° C. was added i-Pr$_2$NEt, followed by EDCI, in portions. The reaction mixture was then warmed up to room temperature and stirred overnight. The reaction solution was diluted with EtOAc and the organic phase was washed with saturated NaHCO$_3$ and NaCl aqueous solution. The organic layer was dried over Na$_2$SO$_4$, concentrated in vacuo. The crude product was purified by flash column chromatography with 10% MeOH/EtOAc as eluent. A yellow solid was obtained. MS (ES+): 427.5 (M+H)+.

Step C: Ethyl 3-{(1-(2-methyl-5-aminophenyl)-5-oxopyrrolidin-3-yl)carbonylamino}-3-(3-pyridyl)lpropanoate Ethyl 3-{(1-(2-methyl-5-nitrophenyl)-5-oxopyrrolidin-3-yl)carbonylamino}-3-(3-pyridyl)propanoate was dissolved in THF/MeOH/H$_2$O solution at 0° C. AcOH was added followed by activated Zn powder. The reaction was then stirred at room temperature for 5 hours. The Zn powder was filtered through a pad of celite. The filtrate was concentrated in vacuo and the residue was re-dissolved in EtOAc. A white precipitate formed and was removed by filtration. The organic solution was concentrated in vacuo to afforded yellow foam, which was further purified by silica gel chromatograph. MS (ES+): 397.5 (M+H)+.

EXAMPLE 31

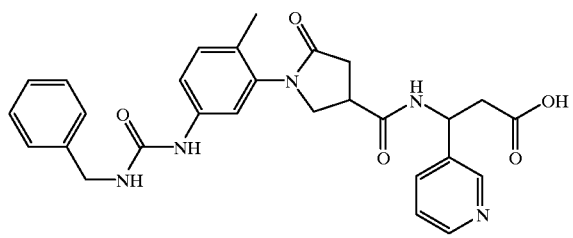

Preparation of 3-{(1-(2-methyl-5-{(benzylamino)carbonylamino}phenyl)-5-oxopyrrolidin-3-yl)carbonylamino}-3-(3-pyridyl)propanoic acid Step A: Ethyl 3-{(1-(2-methyl-5-{(benzylamino)carbonylamino}phenyl)-5-oxopyrrolidin-3-yl)carbonylamino}-3-(3-pyridyl)propanoate To a solution of Ethyl 3-{(1-(2-methyl-5-aminophenyl)-5-oxopyrrolidin-3-yl)carbonylamino}-3-(3-pyridyl)propanoate in CH$_3$CN was added 0.1 mL of acetic acid, followed by benzyl isocyanate. The reaction was allowed to stir at room temperature for 10 hours. The reaction mixture was diluted with EtOAc, and washed with saturated NaHCO$_3$ and brine solution. The organic layer was dried over Na$_2$SO$_4$ and concentrated in vacuo. The crude product was purified by flash chromatography with 10% MeOH/EtOAc provide a light yellow solid. MS (ES+): 544.5 (M+H)+.

Step B: 3-{(1-(2-methyl-5-{(benzylamino)carbonylamino}phenyl)-5-oxopyrrolidin-3-yl)carbonylamino}-3-(3-pyridyl)propanoic acid, sodium salt To a solution of ethyl 3-{(1-(2-methyl-5-{(benzylamino)carbonylamino}phenyl)-5-oxopyrrolidin-3-yl)carbonylamino}-3-(3-pyridyl)propanoate in water/THF/MeOH was added 1.1 eq 1 N NaOH. The volume ratio of NaOH/water/THF/MeOH was 1:3:4:4. The reaction was stirred at room temperature overnight, and then concentrated in vacuo. The residue was dissolved in 5% MeOH/CH$_2$Cl$_2$. After removing the non-soluble material by filtration, the solution was concentrated in vacuo to provide light yellow solid. MS (ES+): 538.5 (M+Na)+.

EXAMPLE 32

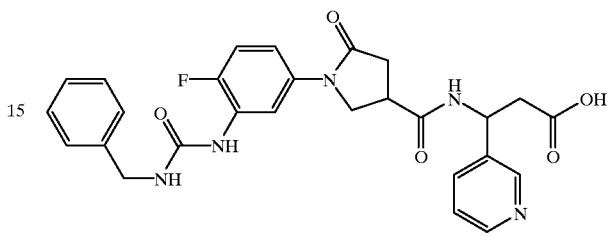

3-{(1-(4-fluoro-5-{(benzylamino)carbonylamino}phenyl)-5-oxopyrrolidin-3-yl)carbonylamino}-3-(3-pyridyl)propanoic acid, sodium salt The title compound was prepared analogously to Examples 30 and 31. MS (ES+) 542.5 (M+Na)+.

EXAMPLE 33

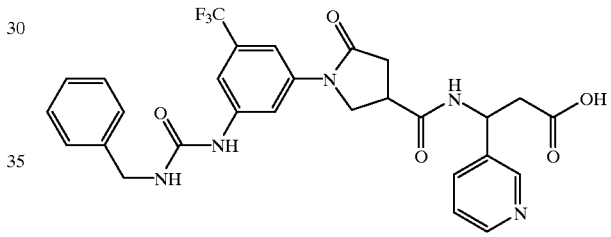

Preparation of 3-{(5-oxo-1-(3-{(benzylamino)carbonylamino}-5-(trifluoromethyl)phenyl)pyrrolidin-3-yl)carbonylamino}-3-(3-pyridyl)propanoic acid Step A: N-(3-amino-5-(trifluoromethyl)phenyl)(benzylamino)carboxamide To a solution of 1-trifluoromethyl-3,5-diaminobenzene (5 g, 0.028 mol) in 25 mL of acetonitrile and acetic acid (0.5 mL) was added a solution of benzyl isocyanate (3.5 mL, 0.028 mol) in acetonitrile (25 mL). The reaction was allowed to stirred at room temperature for 10 hours. The reaction mixture was diluted with EtOAC and washed with saturated NaHCO3, then brine. The organic phase was dried over Na2SO4 and concentrated in vacuo. The product was purified by silica gel chromatograph (EtOAc to 10% MeOH/EtOAc). MS (ES+): 310.5 (M+H)+.

Step B: 5-oxo-1-(3-{(benzylamino)carbonylamino}-5-(trifluoromethyl)phenyl)pyrrolidine-3-carboxylic acid A mixture of N-(3-amino-5-(trifluoromethyl)phenyl)(benzylamino)carboxamide and itaconic acid was fused at 110° C. for 10 hours. The resulted solid was washed with methanol and then dried at 50° C. for 12 hours.

Step C: ethyl 3-{(5-oxo-1-(3-{(benzylamino)carbonylamino}-5-(trifluoromethyl)phenyl)pyrrolidin-3-yl)carbonylamino}-3-(3-pyridyl)pronanoate To a mixture of 5-oxo-1-(3-{(benzylamino)carbonylamino}-5-(trifluoromethyl)phenyl)pyrrolidine-3-carboxylic acid (5 g), ethyl 3-amino-3-pyridylpropanoate and HOAt in DMF at 0° C. was added i-Pr$_2$NEt, followed by EDCI, in portions. The reaction mixture was then stirred overnight at room temperature. The reaction solution was diluted with EtOAc and the organic phase was washed with saturated NaHCO$_3$ and NaCl aqueous solution. The organic layer was dried over Na$_2$SO$_4$ and concentrated in vacuo. The crude product was purified by flash column chromatography with 10% MeOH/EtOAc as eluent. A yellow solid was obtained. MS (ES+): 598.5 (M+H)$^+$.

Step D: 3-{(5-oxo-1-(3-{(benzylamino)carbonylamino}-5-(trifluoromethyl)phenyl)pyrrolidin-3-yl)carbonylamino}-3-(3-pyridyl)propanoic acid, sodium salt To a solution of ethyl 3-{(5-oxo-1-(3-{(benzylamino)carbonylamino}-5-(trifluoromethyl)phenyl)pyrrolidin-3-yl)carbonylamino}-3-(3-pyridyl)propanoate in water/THF/MeOH was added 1.0 eq 1N NaOH. The volume ratio of NaOH/water/THF/MeOH was 1:3:4:4. The reaction was stirred at room temperature overnight, and then concentrated in vacuo. The residue was dissolved in 5% MeOH/CH$_2$Cl$_2$. After removing the non-soluble material by filtration, the solution was concentrated in vacuo to provide a light yellow solid. MS (ES+): 592.5 (M+Na)$^+$.

EXAMPLE 34

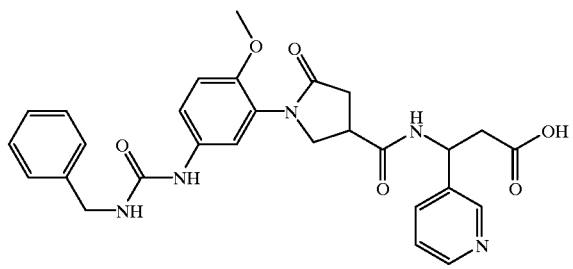

3-{(1-(2-methoxy-5-{(benzylamino)carbonylamino}phenyl)-5-oxo-pyrolidin-3-yl)carbonylamino}-3-(3-pyridyl)propanoic acid, sodium salt The title compound was prepared analogously to Examples 30 and 31. MS (ES+) 554.0 (M+Na)$^+$.

EXAMPLE 35

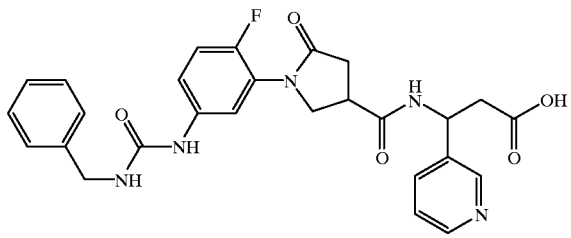

3-{(1-(2-fluoro-5-{(benzylamino)carbonylamino}phenyl)-5-oxopyrrolidin-3-yl)carbonylamino}-3-(3-pyridyl)propanoic acid, sodium salt The title compound was prepared analogously to Examples 30 and 31. MS (ES+) 542.5 (M+Na)$^+$.

EXAMPLE 36

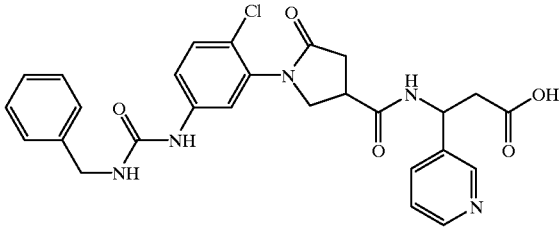

3-{(1-(2-chloro-5-{(benzylamino)carbonylamino}phenyl)-5-oxopyrrolidin-3-yl)carbonylamino}-3-(3-pyridyl)propanoic acid, sodium salt The title compound was prepared analogously to Examples 30 and 31. MS (ES+) 558.0 (M+Na)$^+$.

EXAMPLE 37

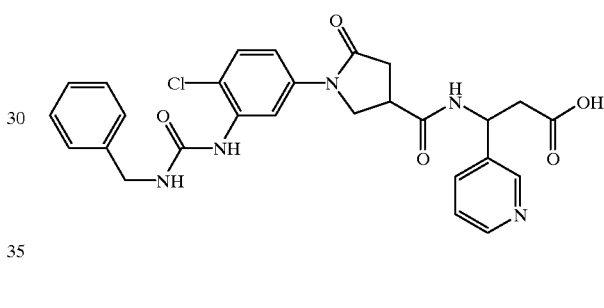

3-{(1-(4-chloro-3-{(benzylamino)carbonylamino}phenyl)-5-oxo-pyrolidin-3-yl)carbonylamino}-3-(3-pyridyl)propanoic acid, sodium salt The title compound was prepared analogously to Examples 30 and 31. MS (ES+) 558.0 (M+Na)$^+$.

EXAMPLE 38

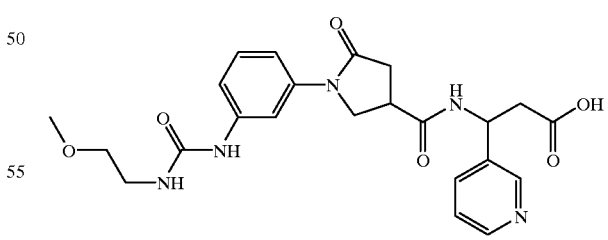

3-{(1-(3-{(2-methoxyethylamino)carbonylamino}phenyl)-5-oxopyrrolidin-3-yl)carbonylamino}-3-(3-pyridyl)propanoic acid, sodium salt The title compound was prepared analogously to Examples 28 and 29. MS (ES+) 492.5 (M+Na+)$^+$.

EXAMPLE 39

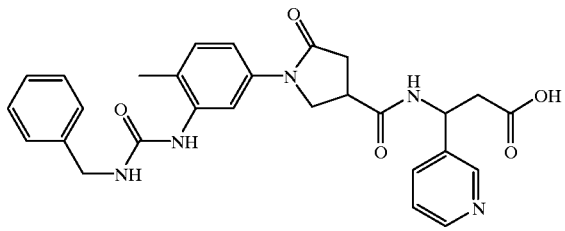

3-{(1-(4-methyl-3-{(benzylamino)carbonylamino}phenyl)-5-oxo-pyrolidin-3-yl)carbonylamino}-3-(3-pyridyl) propanoic acid, sodium salt The title compound was prepared analogously to Examples 30 and 31. MS (ES+) 538.5 (M+Na+)$^+$.

EXAMPLE 40

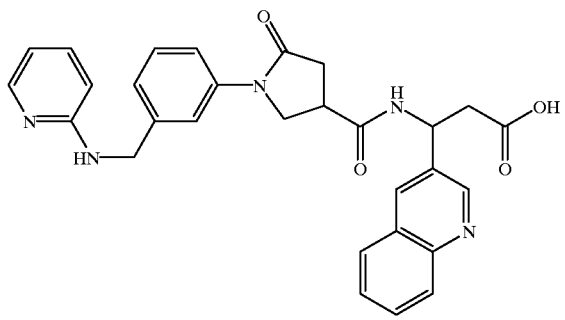

Preparation of 3-{(5-oxo-1-{3-((2-pyridylamino)methyl) phenyl}pyrrolidin-3-yl)carbonylamino}-3-(3-quinolyl) propanoic acid Step A: 1-(3-(hydroxymethyl)phenyl)-5-oxopyrrolidine-3-carboxylic acid A mixture of itaconic acid (13.1 g, 0.1 mol) and 3-aminobenzyl alcohol (12.3 g, 0.1 mol) was heated to 110° C. for 8 hours. The resulted solid was dissolved in MeOH (200 mL). Undissolved solid was removed with filtration and the organic solution was concentrated in vacuo. The off-white solid was collected and dried in vacuo at 50° C. The desired product was obtained as off-white solid. MS (ES−): 234.0 (M−H)$^−$.

Step B: methyl 1-(3-(hydroxymethyl)phenyl)-5-oxopyrrolidine-3-carboxylate 1-(3-(hydroxymethyl)phenyl)-5-oxopyrrolidine-3-carboxylic acid (10 g) was dissolved in methanol. HCl gas was then bubbled through the solution for 10 minutes. The reaction was stirred at room temperature for 6 hours. The reaction solution was concentrated in vacuo to afford the crude product as off-white solid. The desired product was further purified by silica gel chromatograph. MS (ES+): 250.0 (M+H)$^+$.

Step C: methyl (3-formylphenyl)-5-oxopyrrolidine-3-carboxylate

To a solution of methyl 1-(3-(hydroxymethyl)phenyl)-5-oxopyrrolidine-3-carboxylate in CH$_2$Cl$_2$ was added pyridinium chlorochromate (PCC). The reaction was stirred at room temperature overnight. The mixture was then filtered through a pad of celite. The filtrate was concentrated in vacuo and the desired product was obtained after silica gel chromatograph. MS (ES+): 248.0 (M+H)$^+$.

Step D: methyl 5-oxo-1-{3-((2-pyridylamino)methyl) phenyl}pyrrolidine-3-carboxylate A solution of methyl (3-formylphenyl)-5-oxopyrrolidine-3-carboxylate, 2-aminopyridine, and AcOH in trimethylorthoformate was stirred at room temperature overnight. The reaction mixture was concentrated in vacuo and the residue was re-dissolved in methanol. The solution was then cooled to 0° C. AcOH was added followed by NaBH$_3$CN solid in portions. The reaction was allowed to stirred at room temperature for 8 hours. The reaction solution was then concentrated in vacuo. The residue was dissolved in EtOAc and organic solution was washed with saturated NaHCO3 twice. The organic layer was dried over Na$_2$SO$_4$ and concentrated in vacuo. The crude product was purified by silica gel chromatograph (10% meOH/EtOAc) to provide an orange oil.

Step E: 5-oxo-1-{3-((2-pyridylamino)methyl) phenyl}pyrrolidine-3-carboxylic acid To a solution of methyl 5-oxo-1-{3-((2-pyridylamino)methyl)phenyl}pyrrolidine-3-carboxylate in water/THF/MeOH was added 1.0 eq 1N NaOH. The volume ratio of NaOH/water/THF/MeOH was 1:3:4:4. The reaction was stirred at room temperature overnight, and then concentrated in vacuo. The compound was used in the next step without further purification.

Step F: methyl 3-{(5-oxo-1-{3-((2-pyridylamino)methyl) phenyl}pyrrolidin-3-yl)carbonylamino}-3-(3-quinolyl) pronanoate To a mixture of 5-oxo-1-{3-((2-pyridylamino)methyl) phenyl}pyrrolidine-3-carboxylic acid (5 g), ethyl 3-amino-3-pyridylpropanoate and HOAt in DMF at 0° C. was added EDCI, in portions. The reaction mixture was then warmed up to room temperature and stirred overnight. The reaction solution was diluted with EtOAc and the organic phase was washed with saturated NaHCO$_3$ and NaCl aqueous solution. The organic layer was dried over Na$_2$SO$_4$ and concentrated in vacuo. The crude product was purified by flash column with 10% MeOH/EtOAc as eluent. A yellow solid was obtained. MS (ES+): 566.5 (M+H)$^+$.

Step G: 3-{(5-oxo-1-{3-((2-pyridylamino)methyl) phenyl}pyrrolidin-3-yl)carbonylamino}-3-(3-quinolyl) propanoic acid, sodium salt To a solution of methyl 3-{(5-oxo-1-{3-((2-pyridylamino) methyl)phenyl}pyrrolidin-3-yl)carbonylamino}-3-(3-quinolyl)propanoate in water/THF/MeOH was added 1.0 eq 1N NaOH. The volume ratio of NaOH/water/THF/MeOH was 1:3:4:4. The reaction was stirred at room temperature overnight and then concentrated in vacuo. The residue was dissolved in 5% MeOH/CH$_2$Cl$_2$. After removing the non-soluble material by filtration, the solution was concentrated in vacuo to provide a light yellow solid. MS (ES+): 574.5 (M+Na)$^+$.

EXAMPLE 41

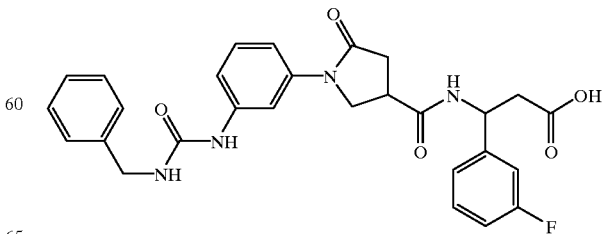

Preparation of 3-(3-Fluorophenyl)-3-{(5-oxo-1-(3-{(benzylamino)carbonylamino}phenyl)pyrrolidin-3-yl)carbonylamino}propanoic acid, sodium salt Step A: methyl 1-(3-nitrophenyl)-5-oxopyrrolidine-3-carboxylate Thionyl chloride (1.7 mL, 23.3 mmol, 1.2 equiv) was added dropwise over 5 min to a suspension of 1-(3-nitrophenyl)-5-oxopyrrolidine-3-carboxylic acid (5.0006 g, 20.0 mmol, 1 equiv) in methanol (71 mL) at −15° C. The resulting suspension was stirred at −15° C. for 50 min, was allowed to warm to 23° C., and was stirred at 23° C. for 72 hr. The reaction was concentrated to dryness in vacuo, and the residue dissolved in dichloromethane (100 mL). The resulting solution was washed sequentially with an aqueous solution of sodium hydroxide (2.0 N, 75 mL) and an aqueous solution of hydrochloric acid (1.5 N, 75 mL). The organic layer was dried over sodium sulfate, was filtered, and was concentrated in vacuo. The residue was purified by flash column chromatography (50% ethyl acetate in hexanes), to give the title compound as a waxy yellow solid. $^1$H NMR (400 MHz, CDCl$_3$) : δ 8.38 (t, 1H, J=2.2 Hz), 8.14 (dd, 1H, J=8.4 Hz, 2.2 Hz), 8.00 (dd, 1H, J=8.2 Hz, 2.0 Hz), 7.55 (t, 1H, J=8.2 Hz), 4.09–4.21 (m, 2H), 3.81 (s, 3H), 3.40–3.48 (m, 1H), 2.97 (ABX, 2H). MS: (+) 265.0 (M+H), 282.0, 287.0; (−) 323.0.

Step B: Methyl 1-(3-aminophenyl)-5-oxopyrrolidine-3-carboxylate

Platinum oxide (202.6 mg, 0.89 mmol, 0.05 equiv) was added to a solution of methyl 1-(3-nitrophenyl)-5-oxopyrrolidine-3-carboxylate (4.2014 g, 15.9 mmol, 1 equiv) in ethyl acetate (170 mL). The resulting suspension was placed under a hydrogen balloon and was stirred at 23° C. for 18 hr. The reaction was filtered through celite and was concentrated in vacuo to give the title compound as a white solid. $^1$H NMR (400 MHz, CDCl$_3$): δ 7.15 (t, 1H, J=2.1 Hz), 7.13 (t, 1H, J=8.1 Hz), 6.78 (dd, 1H, J=8.1 Hz, 1.5 Hz), 6.49 (dd, 1H, J=8.0 Hz, 1.7 Hz), 4.07 (dd, 1H, J=10.0 Hz, 6.8 Hz), 3.99 (dd, 1H, J=10.0 Hz, 8.7 Hz), 3.77 (s, 3H), 3.75 (br s, 2H), 3.29–3.38 (m, 1H), 2.92 (dd, 1H, J=17.3 Hz, 7.8 Hz), 2.84 (dd, 1H, J=17.3 Hz, 9.7 Hz). MS: (+) 235.0 (M+H), 469.5, 703.5; (−) 293.5, 527.0.

Step C: Methyl 5-oxo-1-(3-{(benzylamino)carbonylamino}phenyl)pyrrolidine-3-carboxylate Benzyl isocyanate (2.3 mL, 18.6 mmol, 1.2 equiv) was added to a solution of methyl 1-(3-aminophenyl)-5-oxopyrrolidine-3-carboxylate (3.6169 g, 15.4 mmol, 1 equiv) in dichloromethane (77 mL). The resulting solution was stirred at 23° C. for 27 hr, during which time a white precipitate formed. The reaction was filtered, and the solid was collected to give the title compound as a white solid. $^1$H NMR (400 MHz, DMSO-d$_6$): δ 8.68 (s, 1H), 7.76 (t, 1H, J=1.8 Hz), 7.13–7.36 (m, 8H), 6.59 (t, 1H, J=5.9 Hz), 4.30 (d, 2H, J=5.9 Hz), 4.03 (dd, 1H, J=9.7 Hz, 8.7 Hz), 3.94 (dd, 1H, J=9.5 Hz, 6.1 Hz), 3.68 (s, 3H), 3.41–3.50 (m, 1H), 2.80 (dd, 1H, J=17.0 Hz, 9.5 Hz), 2.71 (dd, 1H, J=17.0 Hz, 7.0 Hz). MS: (+) 368.0 (M+H), 385.5, 390.0, 735.5; (−) 366.0 (M−H), 426.0, 733.5, 793.5.

Step D: 5-Oxo-1-(3-{(benzylamino)carbonylamino}phenyl)pyrrolidine-3-carboxylic acid An aqueous solution of sodium hydroxide (2.0 N, 5.70 mL, 11.4 mmol, 1.01 equiv) was added to a suspension of methyl 5-oxo-1-(3-{(benzylamino)carbonylamino}phenyl)pyrrolidine-3-carboxylate (4.1313 g, 11.2 mmol, 1 equiv) in ethanol (112 mL). The resulting solution was stirred at 23° C. for 22 hr, during which time a white precipitate formed. The reaction was filtered, and the solid was collected to give the sodium salt of the desired product. The solid was partitioned between an aqueous solution of hydrochloric acid (1.5 N, 50 mL), and ethyl acetate (3×100 mL). The combined organic layers were dried over sodium sulfate, were filtered, and were concentrated in vacuo to give the title compound as a white solid. $^1$H NMR (400 MHz, DMSO-d$_6$): δ 12.66 (br s, 1H), 8.68 (s, 1H), 7.76 (m, 1H), 7.13–7.35 (m, 8H), 6.59 (t, 1H, J=6.0 Hz), 4.30 (d, 2H, J=5.9 Hz), 3.98–4.05 (m, 1H), 3.92 (dd, 1H, J=9.8 Hz, 5.7 Hz), 3.30–3.36 (m, 1H), 2.78 (dd, 1H, J=17.0 Hz, 9.5 Hz), 2.69 (dd, 1H, J=17.0 Hz, 6.8 Hz). MS: (+) 354.0 (M+H), 371.0, 707.5; (−) 352.0 (M−H), 705.5.

Step E: Methyl 3-(3-fluorophenyl)-3-{(5-oxo-1-(3-{(benzylamino)carbonylamino}phenyl)pyrrolidin-3-yl)carbonylamino}propanoate 1-(3-(Dimethylamino)propyl)-3-ethylcarbodiimide hydrochloride (99.5 mg, 0.52 mmol, 1.2 equiv), 1-hydroxy-7-azabenzotriazole (12.2 mg, 0.090 mmol, 0.2 equiv), methyl 3-amino-3-(3-fluorophenyl)propanoate hydrochloride (118.8 mg, 0.51 mmol, 1.2 equiv), and N,N-diisopropylethylamine (0.18 mL, 1.03 mmol, 2.4 equiv) were added sequentially to a solution of 5-oxo-1-(3-{(benzylamino)carbonylamino}phenyl)pyrrolidine-3-carboxylic acid (152.2 mg, 0.43 mmol, 1 equiv) in N,N-dimethylformamide (3.0 mL). The resulting solution was stirred at 23° C. for 92 hr. The reaction was partitioned between an aqueous solution of hydrochloric acid (1.5 N, 20 mL) and ethyl acetate (3×25 mL). The combined organic layers were dried over sodium sulfate, were filtered, and were concentrated in vacuo. The residue was purified by flash column chromatography (90% ethyl acetate in hexanes) to give two diastereomers of the title compound (first diastereomer and second diastereomer) as white solids.

First diastereomer: $^1$H NMR (400 MHz, DMSO-d$_6$): δ 8.70 (d, 1H, J=8.3 Hz), 8.68 (s, 1H), 7.77 (s, 1H), 7.05–7.40 (m, 13H), 6.59 (t, 1H, J=6.0 Hz), 5.20–5.27 (m, 1H), 4.29 (d, 1H, J=5.9 Hz), 4.00 (t, 1H, J=9.2 Hz), 3.78 (dd, 1H, J=9.7 Hz, 5.7 Hz), 3.54 (s, 3H), 3.23–3.28 (m, 1H), 2.51–2.77 (m, 4H).

Second diastereomer: $^1$H NMR (400 MHz, DMSO-d$_6$): δ 8.69 (d, 1H, J=8.3 Hz), 8.66 (s, 1H), 7.75 (s, 1H), 7.05–7.40 (m, 12H), 6.58 (t, 1H, J=5.9 Hz), 5.25 (q, 1H, J=7.6 Hz), 4.29 (d, 2H, J=5.8 Hz), 3.94 (t, 1H, J=9.1 Hz), 3.77 (dd, 1H, J=9.6 Hz, 4.6 Hz), 3.58 (s, 3H), 3.23–3.29 (m, 1H), 2.57–2.87 (m, 4H).

Step F: 3-(3-Fluorophenyl)-3-{(5-oxo-1-(3-{(benzylamino)carbonylamino}phenyl)pyrrolidin-3-yl)carbonylamino}propanoic acid, sodium salt An aqueous solution of sodium hydroxide (2.0 N, 77.2 mL, 0.15 mmol, 1.00 equiv) was added to a solution of an equimolar mixture of diastereomers of methyl 3-(3-fluorophenyl)-3-{(5-oxo-1-(3-{(benzylamino)carbonylamino}phenyl)pyrrolidin-3-yl)carbonylamino}propanoate (82.2 mg, 0.15 mmol, 1 equiv) in ethanol (1.5 mL). The resulting solution was stirred at 23° C. for 42 hr. Ethanol (3.0 mL) was added to dissolve the solids that had formed, and the resulting solution was filtered and was concentrated in vacuo to give the title compound as an equimolar mixture of diastereomers, as a white solid. $^1$H NMR (400 MHz, DMSO-d$_6$): δ 9.98 (m, 2H), 9.30 (m, 2H), 8.12 (br s, 2H), 7.73 (s, 1H), 7.62 (s, 1H), 7.46 (d, 1H, J=7.8 Hz), 7.38 (d, 1H, J=8.1 Hz), 6.94–7.29 (m, 26H), 5.07–5.12 (m, 2H), 4.24 (m, 4H), 3.77–3.96 (m, 4H), 3.43 (m, 2H), 2.54–2.75 (m, 8H). MS: (+) 519.5 (M+H)

EXAMPLE 42

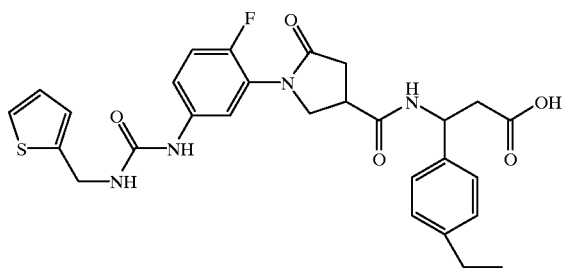

3-(4-ethylphenyl)-3-{(1-(2-fluoro-5-{((2-thienylmethyl)amino)carbonylamino}phenyl)-5-oxopyrrolidin-3-yl)carbonylamino}propanoic acid, sodium salt The title compound was prepared analogously to Example 41. $^1$H NMR (400 MHz, DMSO-$d_6$): δ 10.6 (s, 1H), 8.92 (t, 1H), 8.77 (m, 1H), 6.79–7.95 (m, 8H), 5.14 (dd, 1H, J=7.2Hz, 3.4Hz Hz), 4.36 (d, 2H, J=5.3 Hz), 3.82 (m, 1H), 3.77 (m, 2H), 3.17 (d, 2H, J=5.2Hz), 2.54–2.64 (m, 2H), 2.42 (q, 2H), 1.32 (t, 3H). MS (ES+) 575.5 (M+Na)$^+$.

EXAMPLE 32

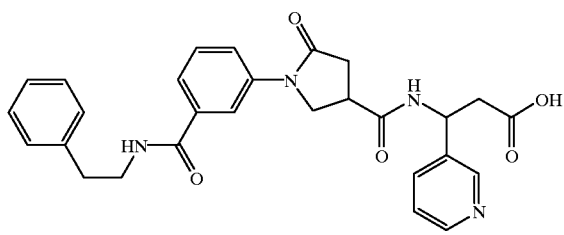

3-{(5-oxo-1-(3-{((2-phenylethyl)amino)carbonyl}phenyl)pyrrolidin-3-yl)carbonylamino}-3-(3-pyridyl)propanoic acid The title compound was prepared analogously to Example 33. MS (ES+) 614.6 (M+TFA)$^+$.

EXAMPLE 44

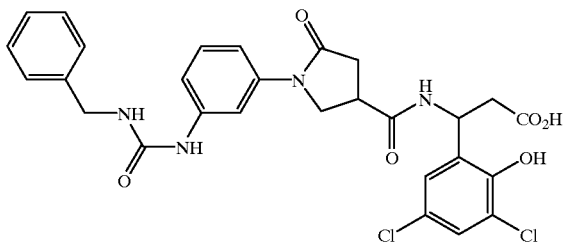

3-(3,5-dichloro-2-hydroxyohenyl)-3-{(5-oxo-1-(3-{(benzylamino)carbonylamino}phenyl)pyrrolidin-3-yl)carbonylamino}propanoic acid The title compound was analogously synthesized to the preparation of 3-(3-fluorophenyl)-3-{(5-oxo-1-(3-{(benzylamino)carbonylamino}phenyl)pyrrolidin-3-yl)carbonylamino}propanoic acid from ethyl 3-amino-3-(3,5-dichloro-2-hydroxyphenyl)propanoate and benzylamine. MS (ES+): 585 (M+H)$^+$; (ES−) : 583 (M−H)$^-$.

EXAMPLE 45

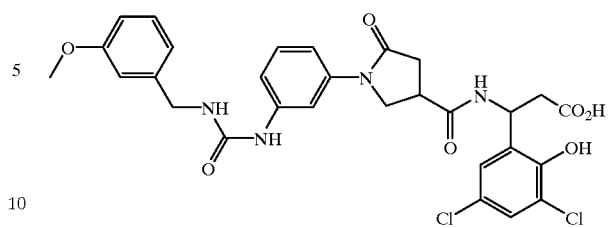

3-(3,5-dichloro-2-hydroxyphenyl)-3-({1-(3-({(3-methoxyohenyl)methyl)amino}carbonylamino)phenyl)-5-oxopyrrolidin-3-yl}carbonylamino)propanoic acid The title compound was analogously synthesized to the preparation of 3-(3-fluorophenyl)-3-{(5-oxo-1-(3-{(benzylamino)carbonylamino}phenyl)pyrrolidin-3-yl)carbonylamino}propanoic acid from ethyl 3-amino-3-(3,5-dichloro-2-hydroxyphenyl)propanoate and 2-methoxybenzylamine. MS (ES+): 615 (M+H)$^+$; (ES−): 613 (M−H)$^-$.

EXAMPLE 45

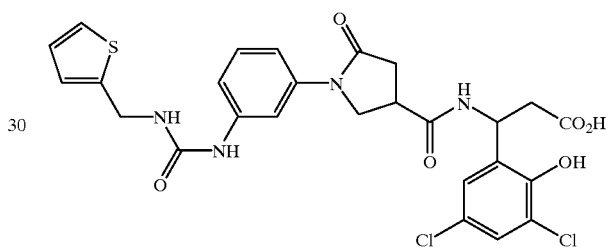

3-(3,5-dichloro-2-hydroxyphenyl)-3-{(5-oxo-1-(3-{((2-thienylmethyl)amino)carbonylamino}phenyl)pyrrolidin-3-yl)carbonylamino}propanoic acid The title compound was analogously synthesized to the preparation of 3-(3-fluorophenyl)-3-{(5-oxo-1-(3-{(benzylamino)carbonylamino}phenyl)pyrrolidin-3-yl)carbonylamino}propanoic acid from ethyl 3-amino-3-(3,5-dichloro-2-hydroxyphenyl)propanoate and 2-thienylmethyl amine. MS (ES+): 591 (M+H)$^+$; (ES−): 589 (M−H)$^-$.

EXAMPLE 47

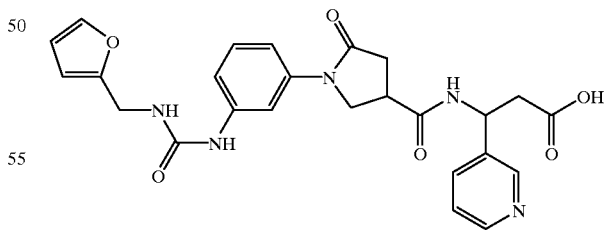

Preparation of 3-{(1-(3-{(N-(2-furylmethyl)carbamoyl)methyl}phenyl)-5-oxopyrrolidin-3-yl)carbonylamino}-3-(3-pyridyl)propanoic acid Step A: phenylmethyl 2-(3-nitrophenyl)acetate To a mixture of 2-(3-nitrophenyl)acetic acid (Aldrich, 9.0 g, 49.68 mmol, 1.0 eq), triethylamine (7.62 mL, 54.65 mmol, 1.1 eq) and $CH_2Cl_2$ (150 mL) in ice bath, was added benzyl chloroformate (Aldrich, 7.46 mL, 49.68 mmol, 1.0 eq) slowly. 4-(N, N-dimethylamino)pyridine (6.07 g, 49.68 mmol, 1.0 eq) was added 5 min. later. The reaction was stirred for 3 hours. The mixture was washed with saturated NaHCO$_3$, then 0.1 N HCl, and saturated NaCl. The organic phase was dried over Na$_2$SO$_4$, filtered, and concentrated on rotary evaporator. Flash chromatography (10% EtOAc in hexane) afforded a white solid. MS (ES–): 270 (M–H)$^-$.

Step B: ethyl 3-{(5-oxo-1-(3-{(benzyloxycarbonyl)methyl}phenyl)pyrrolidin-3-yl)carbonylamino}-3-(3-pyridyl)propanoate The title compound was analogously synthesized by the method described in steps C, A and B of Example 28 from phenylmethyl 2-(3-nitrophenyl)acetate. This compound was obtained as a white solid. MS (ES+): 530 (M+H)$^+$; (ES–) : 528 (M–H)$^-$.

Step C: 2-(3-(4-{N-(2-(ethoxycarbonyl)-1-(3-pyridyl)ethyl)carbamoyl}-2-oxopyrrolidinyl)phenyl)acetic acid To a solution of ethyl 3-{(5-oxo-1-(3-{(benzyloxycarbonyl)methyl}phenyl)pyrrolidin-3-yl)carbonylamino}-3-(3-pyridyl)propanoate (2.6 g, 5.0 mmol, 1.0 eq), triethylamine (1.5 mL) in methanol (20 mL), was added 10% Pd/C (Aldrich, 0.5 g, 0.5 mmol, 0.1 eq). Hydrogenation was carried out under a pressure of 1 atm. After stirring for 5 hours, the catalyst was filtered through a pad of celite and the filtrate was concentrated with rotary evaporator. The title compound was obtained as an off-white solid. MS (ES+): 440 (M+H)$^+$; (ES–): 438 (M–H)$^-$.

Step D: 3-{(1-(3-{(N-(2-furylmethyl)carbamoyl)methyl}phenyl)-5-oxopyrrolidin-3-yl)carbonylamino}-3-(3-pyridyl)propanoic acid The title compound was analogously synthesized by the method described in step B of Example 28 and step B of Example 29 from 2-furylmethylamine and 2-(3-(4-{N-(2-(ethoxycarbonyl)-1-(3-pyridyl)ethyl)carbamoyl}-2-oxopyrrolidinyl)phenyl) acetic acid. This compound was obtained as a white solid. $^1$H NMR (MeOH-d$_4$, 400 MHz): δ 2.73–2.99 (m, 4), 3.37 (m, 1), 3.52 (s, 1), 3.53 (s,1), 4.03 (m, 2), 4.34 (d, 2), 5.42 (m, 1), 6.19 (m, 1), 6.31 (m, 1), 7.12 (m, 1), 7.28–7.54 (m, 4), 7.77 (m, 1), 8.28 (m, 1), 8.61 (m, 1), 8.75 (s, 1). MS (ES+): 491 (M+H)$^+$; (ES–) : 489 (M–H)$^-$.

EXAMPLE 48

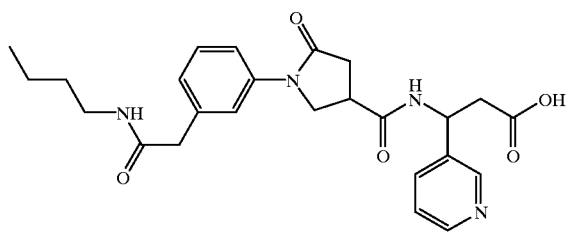

3-((1-{3-((N-butylcarbamoyl)methyl)phenyl}-5-oxopyrrolidin-3-yl)carbonylamino)-3-(3-pyridyl)propanoic acid The title compound was analogously synthesized by the method described in Example 47 from butylamine. This compound was obtained as a white solid. $^1$H NMR (MeOH-d$_4$, 400 MHz): δ 0.91 (m, 3), 1.30–1.51 (m, 4), 2.71–2.97 (m, 4), 3.16 (m, 2), 3.34 (m, 1), 3.49 (d, 2), 4.03 (m, 2), 5.40 (m, 1), 7.11 (m, 1), 7.31 (m, 1), 7.43–7.55 (m, 2), 7.68 (m, 1), 8.17 (m, 1), 8.56 (m, 1), 8.70 (m, 1). MS (ES+): 467 (M+H)$^+$; (ES–): 465(M–H)$^-$.

EXAMPLE 49

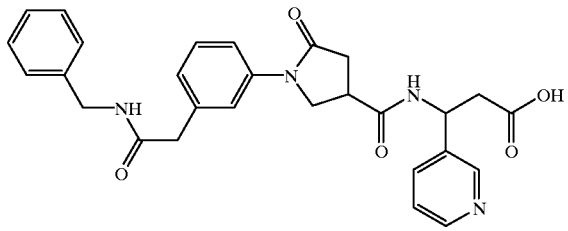

3-{(5-oxo-1-(3-{(N-benzylcarbamoyl)methyl}phenyl)pyrrolidin-3-yl)carbonylamino}-3-(3-pyridyl)propanoic acid The title compound was analogously synthesized by the method described in Example 47 from phenylmethylamine. This compound was obtained as a white solid. $^1$H NMR (MeOH-d$_4$, 400 MHz): δ 2.73–2.98 (m, 4), 3.36 (m, 1), 3.55 (d, 2), 4.03 (m, 2), 4.35 (d, 2), 5.42 (m, 1), 7.19–7.33 (m, 7), 7.49 (m, 2), 7.74 (m, 1), 8.26 (m, 1), 8.60 (m, 1), 8.74 (s, 1). MS (ES+): 501 (M+H)$^+$; (ES–): 499 (M–H)$^-$.

EXAMPLE 50

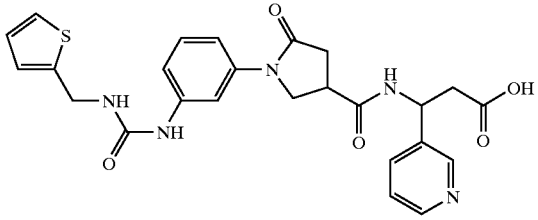

3-{(5-oxo-1-(3-{(N-(2-thienylmethyl)carbamoyl)methyl}phenyl)pyrrolidin-3-yl)carbonylamino}-3-(3-pyridyl)propanoic acid The title compound was analogously synthesized by the method described in Example 47 from 2-thienylmethyl amine. This compound was obtained as a white solid. $^1$H NMR (MeOH-d$_4$, 400 MHz): δ 2.72–3.00 (m, 4), 3.36 (m, 1), 3.53 (d, 2), 4.03 (m, 2), 4.52 (d, 2), 5.42 (m, 1), 6.88–6.94 (m, 2), 7.12 (m, 1), 7.22–7.34 (m, 2), 7.43–7.55 (m, 2), 7.81 (m, 1), 8.34 (m, 1), 8.63 (m, 1), 8.78 (s, 1). MS (ES+): 507 (M+H)$^+$; (ES–): 505 (M–H)$^-$.

EXAMPLE 51

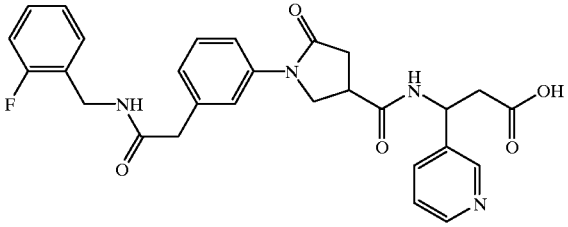

3-({1-(3-({N-((2-fluorophenyl)methyl)carbamoyl}methyl)phenyl)-5-oxopyrrolidin-3-yl}carbonylamino)-3-(3-pyridyl)propanoic acid The title compound was analogously synthesized by the method described in Example 47 from (2-fluorophenylmethyl)amine. This compound was obtained as a white solid. MS (ES+): 520 (M+H)$^+$; (ES–) 518 (M–H)$^-$.

EXAMPLE 52

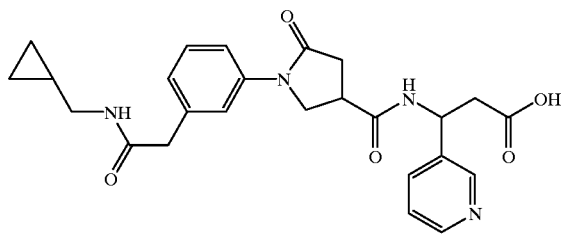

3-{(1-(3-{ (N-(cycloproylmethyl)carbamoyl) methyl}phenyl)-5-oxopyrrolidin-3-yl)carbonylamino}-3-(3-pyridyl)propanoic acid The title compound was analogously synthesized by the method described in Example 47 from cyclopropylmethylamine. This compound was obtained as a white solid. MS (ES+) 466 (M+H)⁺; (ES−): 464 (M−H)⁻.

EXAMPLE 53

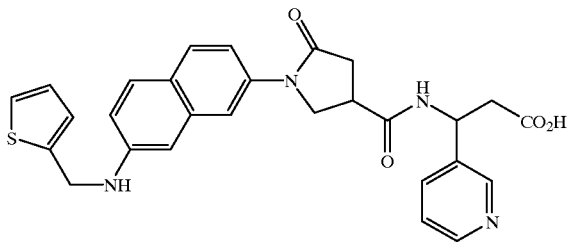

Preparation of 3-((5-oxo-1-{7-((2-thienylmethyl)amino)(2-naphthyl)l}pyrrolidin-3-yl)carbonylamino)-3-(3-pyridyl)propanoic acid Step A: naphthalene-2,7-diamine To a solution of 2,7-dinitronaphthalene (2.1 g, 10.0 mmol, 1.0 eq) in ethanol (80 mL), was added 10% Pd/C (Aldrich, 1.0 g, 1.0 mmol, 0.1 eq). Hydrogenation was carried out under a pressure of 1 atm. After stirring for 4 hours, the catalyst was filtered through a pad of celite, the filtrate was concentrated with rotary evaporator. The title compound was obtained as an off-white solid. MS (ES+): 159 (M+H)⁺.

Step B: N-(7-amino-naphth-2-yl) (phenylmethoxy) carboxamide

The title compound was prepared by the method described in step A of Example 47. This compound was obtained as a white solid. MS (ES+): 293 (M+H)⁺; (ES−): 291 (M−H)⁻.

Step C: Ethyl 3-((5-oxo-1-{7-((phenylmethoxy) carbonylamino)naphth-2-yl}pyrrolidin-3-yl) carbonylamino)-3-(3-pyridyl)propanoate The title compound was analogously synthesized by the method described in steps A and B of Example 28 from N-(7-amino-naphth-2-yl) (phenylmethoxy)carboxamide. This compound was obtained as a white solid. MS (ES+): 581 (M+H)⁺; (ES−): 579 (M−H)⁻.

Step D: ethyl 3-{(1-(7-amino-naphth-2-yl)-5-oxopyrrolidin-3-yl)carbonylamino}-3-(3-pyridyl)propanoate The title compound was analogously synthesized by the method described in step C of Example 47 from ethyl 3-((5-oxo-1-{7-((phenylmethoxy)carbonylamino)naphth-2-yl)}pyrrolidin-3-yl)carbonylamino)-3-(3-pyridyl) propanoate. This compound was obtained as a white solid. MS (ES+) : 447 (M+H)⁺; (ES−) : 445 (M−H)⁻.

Step E: 3-((5-oxo-1-{7-((2-thienylmethyl)amino)naphth-2-yl)}pyrrolidin-3-yl)carbonylamino)-3-(3-pyridyl)propanoic acid A mixture of 2-thiophenecarboxaldehyde (Aldrich, 20 μL, 0.2 mmol), ethyl 3-{(1-(7-amino-naphth-2-yl)-5-oxopyrrolidin-3-yl)carbonylamino}-3-(3-pyridyl) propanoate (94 mg, 0.2 mmol), acetic acid (13 μL, 0.2 mmol), triacetoxy sodium borohydride (Aldrich, 67 mg, 0.3 mmol) in CH₂Cl₂ (2 mL) was stirred at room temperature overnight. Then the mixture was added CH₂Cl₂ and washed with NaHCO₃. The organic phase was dried over Na₂SO₄. filtered, and concentrated on rotary evaporator. Preparative TLC in 10% MeOH-CH₂Cl₂ afforded ethyl 3-((5-oxo-1-{7-((2-thienylmethyl)amino)naphth-2-yl)}pyrrolidin-3-yl)carbonylamino)-3-(3-pyridyl)propanoate as an off-white solid. The title compound, a off-white solid, was analogously synthesized by the method described in step B of Example 1. $^1$H NMR (MeOH-d₄, 400 MHz): δ 2.76–3.02 (m, 4), 3.40 (m, 1), 3.99–4.08 (m, 2), 4.61 (s, 2), 5.44 (m, 1), 6.94–7.07 (m, 3), 7.26 (m, 1), 7.47 (m, 1), 7.61 (m, 3), 7.88 (m, 2), 8.41 (m, 1), 8.64 (m, 1), 8.82 (s, 1). MS (ES+): 515 (M+H)⁺; (ES−) : 513 (M−H)⁻.

EXAMPLE 54

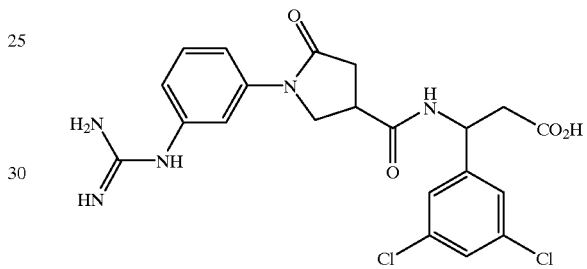

Preparation of 3-({1-(3-(amidinoamino)phenyl)-5-oxopyrrolidin-3-yl}carbonylamino)-3-(3.5-dichlorophenyl) propanoic acid, trifluoroacetate Step A: methyl 3-{(1-(3-aminophenyl)-5-oxopyrrolidin-3-yl)carbonylamino}-3-(3 5-dichlorophenyl)propanoate The title compound was analogously synthesized by the method described in Example 28 from methyl 3-amino-3-(3,5-dichlorophenyl)propanoate. The title compound was obtained as a yellow solid. MS (ES+): 450 (M+H)⁺; (ES−): 448 (M−H)⁻.

Step B: tert-butyl (2 E)-2-aza-3-{(3-(4-{N-(1-(3,5-dichlorophenyl)-2-(methoxycarbonyl)ethyl)carbamoyl}-2-oxoyrrolidinyl)phenyl)amino}-3-((tert-butoxy) carbonylamino)prop-2-enoate A mixture of methyl 3-{(1-(3-aminophenyl)-5-oxopyrrolidin-3-yl)carbonylamino}-3-(3,5-dichlorophenyl) propanoate (300 mg, 0.67 mmol, 1.0 eq), (tert-butoxy)-N-{((tert-butoxycarbonyl)amino)thioxomethyl}carboxamide (222 mg, 0.80 mmol, 1.2 eq), mercury (II) chloride (255 mg, 0.94 mmol, 1.4 eq) and triethylamine (271 mg, 2.68 mmol, 4.0 eq) in DMF (4 mL) was stirred at room temperature overnight. The reaction mixture was diluted with ethyl acetate and passed through a pad of celite. Water was added and the product was extracted with ethyl acetate (80 mL×3). The organic extractant was washed with brine, dried with MgSO4, filtered and concentrated. Column chromatography (0–50% EtOAc-hexane) afforded the title compound as a white solid. MS (ES+): 692 (M+H)⁺.

Step C: 3-({1-(3-({(1 E)-2-aza-2-(tert-butoxycarbonyl)-1-((tert-butoxycarbonyl)amino)vinyl}amino)phenyl)-5-oxopyrrolidin-3-yl}carbonylamino)-3-(3,5-dichlorophenyl) propanoic acid The title compound was analogously synthesized by the method described in Step B of Example 27 from tert-butyl (2 E)-2-aza-3-{(3-(4-{N-(1-(3,5-dichlorophenyl)-2-(methoxycarbonyl)ethyl)carbamoyl}-2-oxopyrrolidinyl)phenyl)amino)-3-((tert-butoxycarbonyl)amino)prop-2-enoate (238 mg, 0.344 mmol, 1.0 eq). The title compound was obtained as a colorless sticky solid. MS (ES+): 678 (M+H)⁺; (ES–): 676 (M–H)⁻.

Step D: 3-({1-(3-(amidinoamino)phenyl)-5-oxopyrrolidin-3-yl}carbonylamino)-3-(3,5-dichlorophenyl)propanoic acid, trifluoroacetate A solution of 3-({1-(3-({(1E)-2-aza-2-(tert-butoxycarbonyl)-1-((tert-butoxycarbonyl)amino)vinyl}amino)phenyl)-5-oxopyrrolidin-3-yl}carbonylamino)-3-(3,5-dichlorophenyl)propanoic acid in trifluoroacetic acid (2 mL) was stirred at room temperature for 1 hour. Solvent was removed under reduced pressure. Reverse phase high-performance liquid chromatography (CH₃CN—H₂O/01% TFA) afforded the title compound as a white solid. ¹H NMR (CD₃OD, 400 MHz) δ 2.72–2.97 (m, 4), 3.39 (m, 1), 3.80 (m, 4), 3.97–4.18 (m, 3), 5.32 (m, 1), 7.11 (m, 1), 7.39 (m, 3), 7.48 (m, 2), 7.76 (m, 1). MS (ES+): 478 (M+H)⁺.

EXAMPLE 55

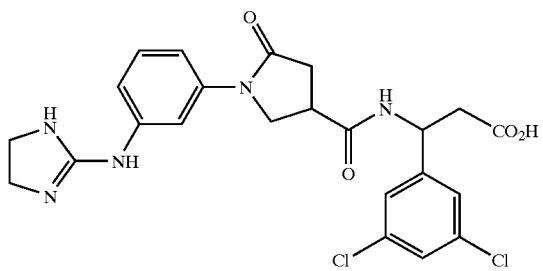

3-(3,5-dichlorophenyl)-3-({1-(3-(2-imidazolin-2-ylamino)phenyl)-5-oxopyrrolidin-3-yl}carbonylamino)propanoic acid, trifluoroactate The title compound was analogously synthesized by the method described in Example 54 from methyl 3-{(1-(3-aminophenyl)-5-oxopyrrolidin-3-yl)carbonylamino}-3-(3,5-dichlorophenyl)propanoate and tert-butyl 3-(tert-butoxycarbonyl)-2-thioxoimidazolidinecarboxylate. The title compound was obtained as a colorless semisolid. ¹H NMR (CD₃OD, 400 MHz) δ 2.71–2.97 (m, 4), 3.38 (m, 1), 3.97–4.19 (m, 2), 5.32 (m, 1), 7.14 (m, 1), 7.38 (m, 3), 7.51 (m, 2), 7.75 (m, 1). MS (ES+): 504 (M+H)⁺; (ES–) 502 (M–H)⁻.

EXAMPLE 56

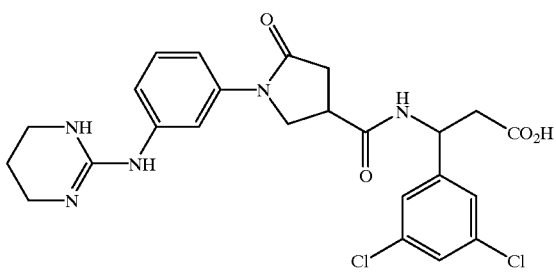

3-(3,5-dichlorophenyl)-3-({5-oxo-1-(3-(3,4,5,6-tetrahydropyrimidin-2-ylamino)phenyl)pyrrolidin-3-yl}carbonylamino)propanoic acid, trifluoroacetate The title compound was analogously synthesized by the method described in Example 54 from methyl 3-{(1-(3-aminophenyl)-5-oxopyrrolidin-3-yl)carbonylamino}-3-(3,5-dichlorophenyl)propanoate and tert-butyl 3-(tert-butoxycarbonyl)-2-thioxo-1,3-diazaperhydroine carboxylate. The title compound was obtained as a white solid. MS (ES+): 518 (M+H)⁺; (ES–): 516 (M–H)⁻.

EXAMPLE 57

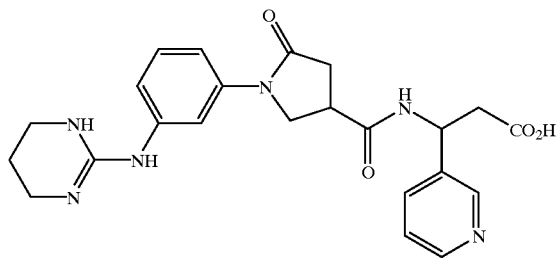

3-({5-oxo-1-(3-(3,4,5,6-tetrahydropyrimidin-2-ylamino)phenyl)pyrrolidin-3-yl}carbonylamino)-3-(3-pyridyl)propanoic acid, trifluoroacetate The title compound was analogously synthesized by the method described in Example 54 from ethyl 3-{(1-(3-aminophenyl)-5-oxopyrrolidin-3-yl)carbonylamino}-3-(3-pyridyl)propanoate and tert-butyl 3-(tert-butoxycarbonyl)-2-thioxo-1,3-diazaperhydroinecarboxylate. The title compound was obtained as a white solid. MS (ES+): 451 (M+H)⁺; (ES–): 449 (M–H)⁻.

EXAMPLE 58

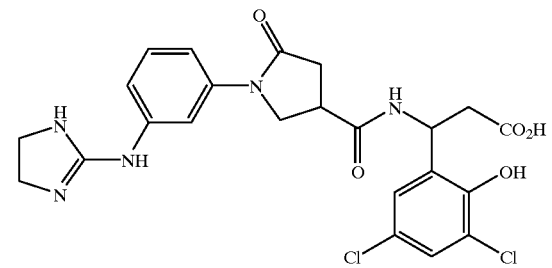

Preparation of 3-(3,5-dichloro-2-hydroxyphenyl)-3-({1-(3-(2-imidazolin-2-ylamino)phenyl)-5-oxopyrrolidin-3-yl}carbonylamino)propanoic acid, trifluoroacetate Step A: Ethyl 3-({1-(3-(aza{1,3-bis(tert-butoxycarbonyl)imidazolidin-2-ylidene}methyl)phenyl)-5-oxopyrrolidin-3-yl}carbonylamino)-3-(3,5-dichloro-2-hydroxyphenyl)propanoate The title compound was analogously synthesized by the method described in the Step B of Example 54 from ethyl 3-{(1-(3-aminophenyl)-5-oxopyrrolidin-3-yl)carbonylamino}-3-(3,5-dichloro-2-hydroxyphenyl)propanoate and tert-butyl 3-(tert-butoxycarbonyl)-2-thioxoimidazolidine carboxylate. MS (ES+): 748 (M+H)⁺; (ES–) : 746 (M–H)⁻.

Step B: Ethyl 3-(3,5-dichloro-2-hydroxyphenyl)-3-({1-(3-(2-imidazolin-2-ylamino)phenyl)-5-oxopyrrolidin-3-yl}carbonylamino)propanoate The title compound was analogously synthesized by the method described in the Step D of Example 54 from ethyl 3-({1-(3-(aza{1,3-bis(tert-butoxycarbonyl)imidazolidin-2-ylidene}methyl)phenyl)-5-oxopyrrolidin-3-yl}carbonylamino)-3-(3,5-dichloro-2-hydroxyphenyl)propanoate. MS (ES+): 548 (M+H)⁺.

Step C: 3-(3,5-dichloro-2-hydroxyphenyl)-3-({1-(3-(2-imidazolin-2-ylamino)phenyl)-5-oxopyrrolidin-3-yl}carbonylamino)propanoic acid, trifluoroacetate The title compound was analogously synthesized by the method described in the Step C of Example 54 from ethyl 3-(3,5-dichloro-2-hydroxyphenyl)-3-({1-(3-(2-imidazolin-2-ylamino)phenyl)-5-oxopyrrolidin-3-yl}carbonylamino)propanoate. MS (ES+): 520 (M+H)$^+$; (ES–): 518 (M–H)$^-$.

EXAMPLE 59

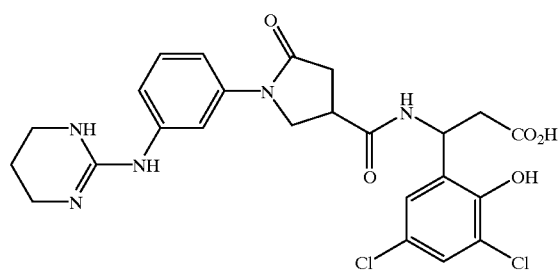

3-(3,5-dichloro-2-hydroxyphenyl)-3-({5-oxo-1-(3-(3,4,5,6-tetrahydropyrimidin-2-ylamino)phenyl)pyrrolidin-3-yl}carbonylamino)propanoic acid, trifluoroacetate:

The title compound was analogously synthesized by the method described in Example 58 from ethyl 3-{(1-(3-aminophenyl)-5-oxopyrrolidin-3-yl)carbonylamino1-3-(3,5-dichloro-2-hydroxyphenyl)propanoate and tert-butyl3-(tert-butoxycarbonyl)-2-thioxo-1,3-diazaperhydroine carboxylate. MS (ES+): 534 (M+H)$^+$; (ES–): 532 (M–H)$^-$.

EXAMPLE 60

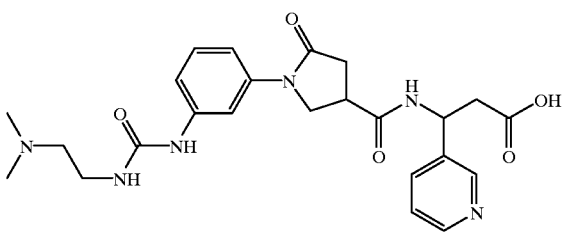

3-({1-(3-({N-(2-(dimethylamino)ethyl)carbamoyl}amino)phenyl)-5-oxopyrrolidin-3-yl}carbonylamino)-3-(3-pyridyl)propanoic acid The title compound was analogously synthesized by the method described in Example 1 from (2-aminoethyl)dimethylamine. This compound was obtained as a white solid. $^1$H NMR (MeOH-d$_4$, 400 MHz) : δ 2.70–3.06 (m, 13), 3.56 (m, 2), 4.04 (m, 2), 5.41 (m, 1), 7.10–7.30 (m, 3), 7.68–7.82 (m, 2), 8.21 (m, 1), 8.60 (m, 1), 8.72 (m, 1). MS (ES+): 483 (M+H)$^+$; (ES–) : 481 (M–H)$^-$.

EXAMPLE 61

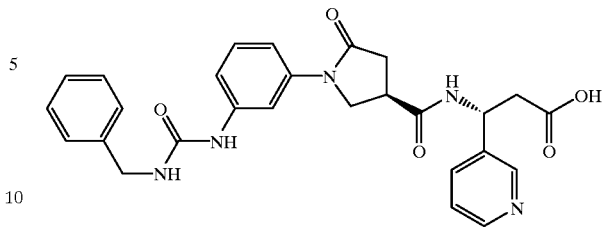

(3R)-3-{((3R)-5-oxo-1-(-{(benzylamino)carbonylamino}phenyl)pyrrolidin-3-yl)carbonylamino}-3-(3-pyridyl)propanoic acid, trifluoroacetate This compound was analogously synthesized by the method described in Examples 28 and 29 from ethyl (3 R)-3-amino-3-pyridylpropanoate. The title compound was obtained as a white solid. MS (ES+): 502 (M+H)$^+$; (ES–): 500 (M–H)$^-$.

EXAMPLE 62

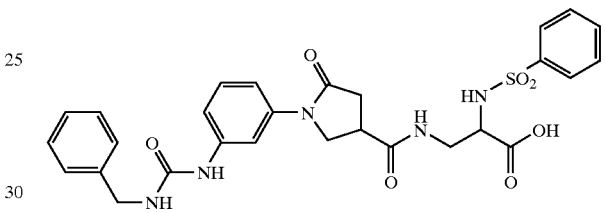

Preparation of L-2-(phenylsulfonylamino)-3-{(5-oxo-1-(3-(benzylamino)carbonylamino}phenyl)pyrrolidin-3-yl)carbonylaminolpropionic acid, sodium salt Step A: Methyl L-2-(benzyloxycarbonylamino)-3-aminopropionate Hydrochloride To a chilled (–11° C. wet ice/acetone) suspension of L-2-(benzyloxycarbonylamino)-3-aminopropionic acid (Bachem 10.0 g, 42 mmol, 1.0 equiv) in 150 mL anhydrous methanol was added thionyl chloride (3.37 mL, 46.2 mmol, 1.1 equiv) at a rate of 0.3 mL/min via a syringe pump. Resulting solution was warmed to room temperature overnight. Solvents were stripped in-vacuo, and the resulting foam triturated with diethylether and the desired product was filtered.

Step B: Methyl L-2-(benzyloxycarbonylamino)-3-{(5-oxo-1-(3-{(benzylamino)carbonylamino}phenyl)pyrrolidin-3-yl)carbonylamino}propionate To a solution of 5-oxo-1-(3-((benzylamino)carbonylaminophenyl)pyrrolidine-3-carboxylic acid (100 mg, 0.28 mmol, 1 equiv) in N,N-dimethylformamide (1.0 mL) at 60° C. was added carbodiimidizole (50 mg, 0.31 mmol, 1.1 equiv) and stirred for 30 min. Methyl L-2-(benzyloxy carbonylamino)-3-aminopropionate hydrochloride (101 mg, 0.35 mmol, 1.25 equiv) and N,N-diisopropylethyl amine (61 μL, 0.35 mmol, 1.25 equiv) in N,N-dimethyl formamide (1.0 mL) was then added and stirred for an additional 90 min at 60° C. The DMF was stripped in-vacuo. The residue was dissolved in ethyl acetate, washed twice with 5% NaHCO$_3$, brine, dried over MgSO$_4$, filtered and stripped in-vacuo to yield the desired product as a white solid.

Step C: Methyl L-2-amino-3-{(5-oxo-1-(3-{(benzylamino)carbonylamino}phenyl)pyrrolidin-3-yl)carbonylamino}propionate To a solution of methyl L-2-(benzyloxycarbonylamino)-3-{(5-oxo-1-(3-{(benzylamino)carbonylamino}phenyl)

pyrrolidin-3-yl)carbonylamino}propionate (154 mg) in MeOH (10 mL) under nitrogen was added Pd/C (10 mg). The vessel was charged with hydrogen under balloon pressure. After 45 min., the mixture was filtered through a bed of celite and the solvents stripped in-vacuo to yield the desired product as a solid. MS: (+) 454.5 (M+H).

Step D: Methyl L-2-(phenylsulfonylamino)-3-{(5-oxo-1-(3-{(benzylamino)carbonylamino}phenyl)pyrrolidin-3-yl)carbonylamino}propionate A suspension of methyl L-2-amino-3-{(5-oxo-1-(3-{(benzylamino)carbonylamino}phenyl)pyrrolidin-3-yl) arbonylamino}propionate (118 mg, 0.26 mmol, 1 equiv.), benzenesulfonylchloride (66 μL, 0.52 mmol, 2.0 equiv) and N,N-Diisopropylethylamine (91 μL, 0.52 mmol, 2.0 equiv) in 15 mL methylene chloride and 10 mL tetrahydrofuran was heated to 35° C. for 16 hrs. Solvents stripped in-vacuo, dissolved in methylene chloride, washed twice with 5% NaHCO$_3$, brine, dried over MgSO$_4$ and preloaded onto silica. Product separated on silica eluting with 5% methanol in methylene chloride. The solvent was striped in-vacuo to yield the desired product as a white foam. MS: (+) 594.5 (M+H).

Step E: L-2-(phenylsulfonylamino)-3-{(5-oxo-1-(3-{(benzylamino)carbonylamino}phenyl)pyrrolidin-3-yl) carbonylamino)propionic acid. sodium salt A solution of methyl L-2-(phenylsulfonylamino)-3-{(5-oxo-1-(3-{(benzylamino)carbonylamino}phenyl)pyrrolidin-3-yl)carbonylamino}propionate (105 mg, 0.18 mmol, 1.0 equiv) and sodium hydroxide (53 μL of 5 M, 0.27 mmol, 1.5 equiv) was stirred overnight. The solvent was stipped in-vacuo. The residue was re-dissolved in 0.5 mL methanol and the product precipitated by the introduction of diethylether. Product was isolated by filtration. MS: (+) 602.5 (M+H).

EXAMPLE 63

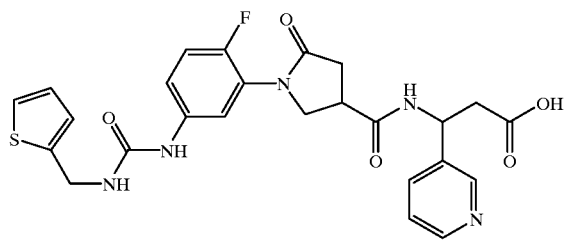

3-{(1-(2-fluoro-5-{((2-thienylmethyl)amino) carbonylamino}phenyl)-5-oxopyrrolidin-3-yl) carbonylamino}-3-(3-pyridyl)propanoic acid. sodium salt The title compound was prepared analogously to Examples 30 and 31. MS (ES+) 548.5 (M+Na)$^+$.

EXAMPLE 64

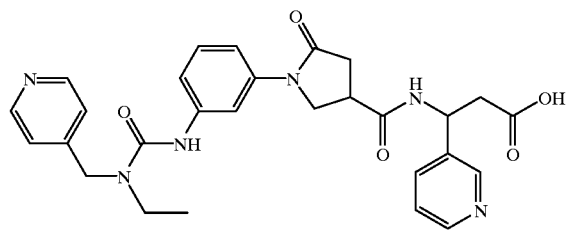

3-{(1-(3-{(N-ethyl-N-(4-pyridylmethyl)amino) carbonylamino}phenyl)-5-oxopyrrolidin-3-yl) carbonylamino}-3-(3-pyridyl)propanoic acid, sodium salt The title compound was prepared analogously to Examples 28 and 29. MS (ES+) 553.5 (M+Na)$^+$.

EXAMPLE 65

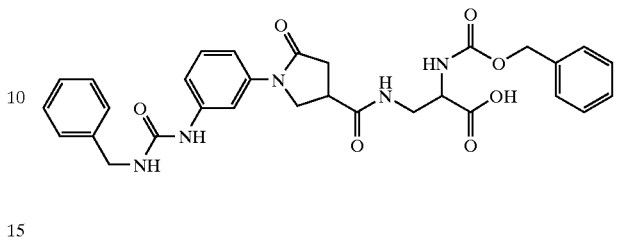

3-{(5-oxo-1-(3-{(benzylamino)carbonylamino}phenyl) pyrrolidin-3-yl)carbonylamino}-2-((phenylmethoxy) carbonylamino)propanoic acid, sodium salt The title compound was prepared analogously to Example 41. MS (ES+) 596.5 (M+Na)$^+$.

EXAMPLE 66

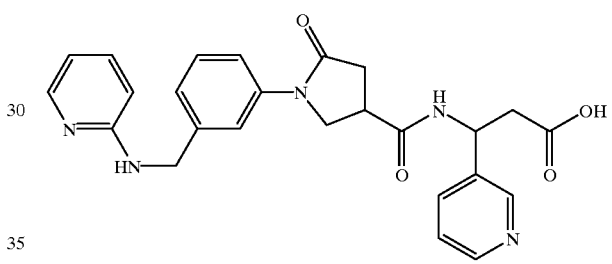

3-{(5-oxo-1-{3-((2-pyridylamino)methyl) phenyl}pyrrolidin-3-yl)carbonylamino}-3-(3-pyridyl) propanoic acid, sodium salt The title compound was prepared analogously to Example 40. MS (ES+) 482.5 (M+Na)$^+$.

EXAMPLE 67

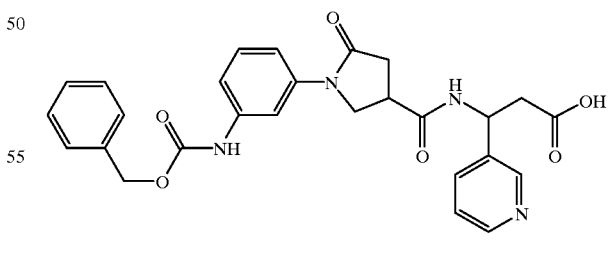

3-((5-oxo-1-{3-(((phenylmethoxy)carbonylamino) phenyl}pyrrolidin-3-yl)carbonylamino}-3-(3-pyridyl) propanoic acid, sodium salt The title compound was prepared analogously to Examples 30 and 31. MS (ES+) 542.5 (M+Na)$^+$.

EXAMPLE 68

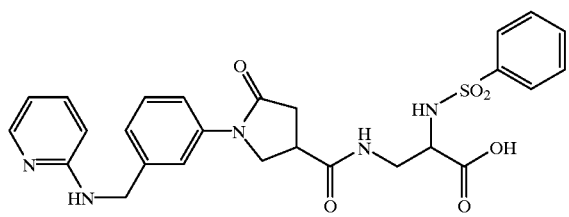

3-((5-oxo-1-{3-((2-pyridylamino)methyl)phenyl}pyrrolidin-3-yl)carbonylamino)-2-(phenylsulfonylamino)propanoic acid, sodium salt The title compound was prepared analogously to Example 40. MS (ES+) 560.0 (M+Na)+.

EXAMPLE 69

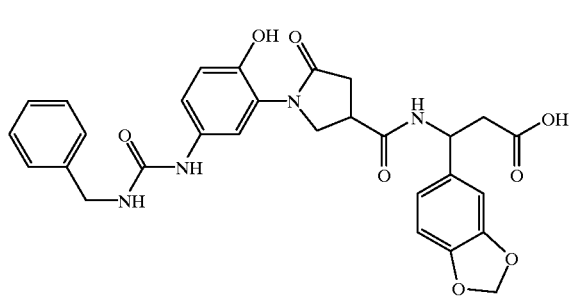

3-(1,3-benzodioxol-5-yl)-3-{(5-oxo-1-(2-hydroxy-5-{(benzylamino)carbonylamino}phenyl)pyrrolidin-3-yl)carbonylamino}propanic acid The title compound was prepared analogously to Example 41. MS (ES+) 561.5 (M+H)+.

EXAMPLE 70

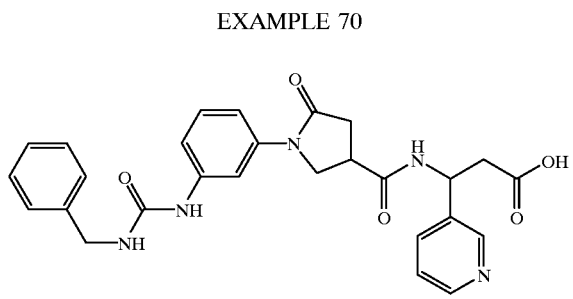

3-{(5-oxo-1-(3-{(benzylamino)carbonylamino}phenyl)pyrrolidin-3-yl)carbonylamino}-3-(3-pyridyl)propanic acid, sodium salt The title compound was prepared analogously to Examples 30 and 31. MS (ES+) 524.5 (M+Na)+.

EXAMPLE 71

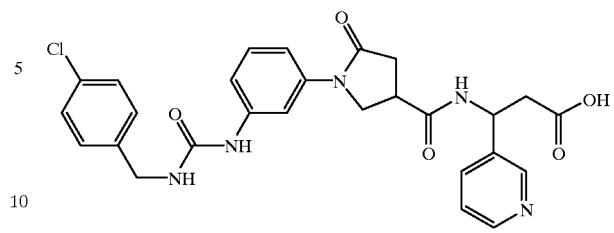

3-({1-(3-({((4-chlorophenyl)methyl)amino}carbonylamino)phenyl)-5-oxopyrrolidin-3-yl}carbonylamino)-3-(3-pyridyl)propanic acid sodium salt The title compound was prepared analogously to Examples 28 and 29. MS (ES+) 558.0 (M+Na)+.

EXAMPLE 72

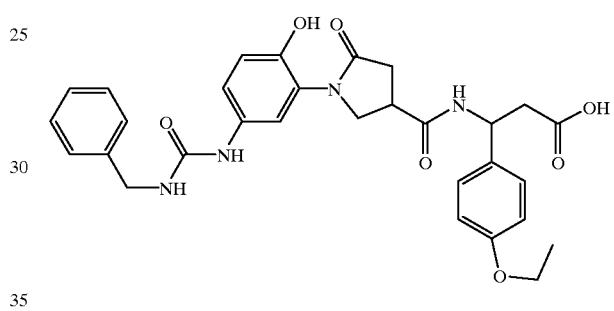

3-(4-ethoxyphenyl)-3-{(1-(2-hydroxy-5-{(benzylamino)carbonylamino}phenyl)-5-oxopyrrolidin-3-yl)carbonylamino}propanic acid The title compound was prepared analogously to Example 41. MS (ES+) 561.5 (M+H)+.

EXAMPLE 73

3-(4-ethoxyohenyl)-3-((5-oxo-1-{3-((2-pyridylamino)methyl)phenyl)pyrrolidin-3-yl)carbonylamino}propanic acid, sodium salt The title compound was prepared analogously to Example 40. MS (ES+) 525.5 (M+Na)+.

EXAMPLE 74

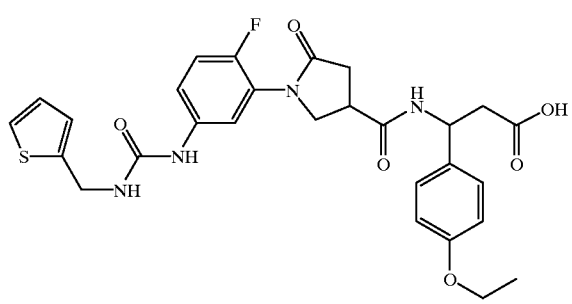

3-(4-ethoxyohenyl)-3-{(1-(2-fluoro-5-{((2-thienylmethyl)amino)carbonylamino}phenyl)-5-oxopyrrolidin-3-yl)carbonylamino}propanoic acid, sodium salt The title compound was prepared analogously to Example 41. $^1$H NMR (400 MHz, DMSO-$d_6$): δ 10.8 (b, 1H), 9.16 (dd, 1H, J=7.7 Hz, 2.7 Hz), 7.48 (m, 2H), 7.33 (dd, 1H, J=3.1 Hz, 1.6 Hz), 7.22 (m, 1H), 7.06 (dt, 1H, J=10.7 Hz, 0.6 Hz, 2.2 Hz), 6.94 (m, 2H), 6.86 (dd, 2H, J=8.7 Hz, 4.5 Hz), 5.04 (m, 1H), 4.38 (d, 2H, J=5.7 Hz), 3.82 (m, 2H), 3.69 (m, 1H), 3.56 (m, 2H), 2.61 (m, 2H), 2.31 (m, 2H), 1.29 (td, 3H, J=6.9 Hz, 2.4 Hz, 4.6 Hz). MS (ES+) 591.5 (M+Na)$^+$.

EXAMPLE 75

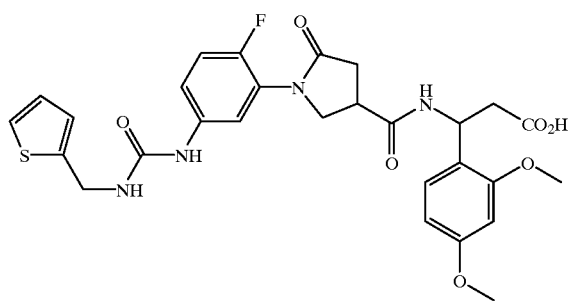

3-(2,4-dimethoxyphenyl)-3-{(1-(2-fluoro-5-{((2-thienylmethyl)amino)carbonylamino}phenyl)-5-oxopyrrolidin-3-yl)carbonylamino}propanoic acid sodium salt The title compound was prepared analogously to Example 41. $^1$H NMR (400 MHz, DMSO-$d_6$): δ 10.7 (d, 1H), 8.74 (b, 1H), 8.50 (s, 1H), 6.88–7.95 (m, 7H), 5.12 (m, 1H), 4.38 (s, 2H), 3.86 (m, 1H), 3.82 (m, 2H), 3.75 (s, 3H), 3.69 (s, 3H), 3.19 (d, 2H, J=5.2 Hz), 2.52–2.64 (m, 2H). MS (ES+) 607.5 (M+Na)$^+$.

EXAMPLE 76

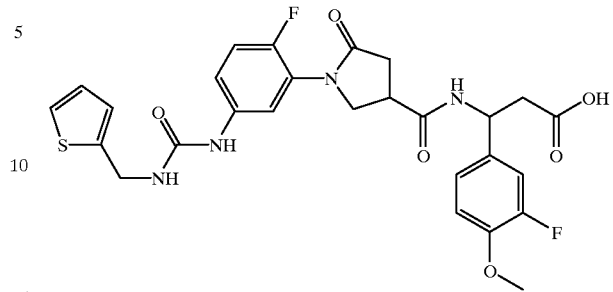

3-(3-fluoro-4-methoxyphenyl)-3-{(1-(2-fluoro-5-{((2-thienylmethyl)amino)carbonylamino}phenyl)-5-oxopyrrolidin-3-yl)carbonylamino}propanoic acid, sodium salt The title compound was prepared analogously to Example 41. $^1$H NMR (400 MHz, DMSO-$d_6$): δ 10.8 (b, 1H), 9.02 (m, 2H), 8.84 (m, 1H), 6.91–7.59 (m, 7H), 5.10 (dd, 1H, J=7.3 Hz, 3.2 Hz Hz), 4.38 (d, 2H, J=5.3 Hz), 3.88 (m, 1H), 3.83 (s, 3H), 3.33 (b, 2H), 3.19 (d, 2H, J=5.2 Hz), 2.54–2.64 (m, 2H). MS (ES+) 595.5 (M+Na)$^+$.

EXAMPLE 77

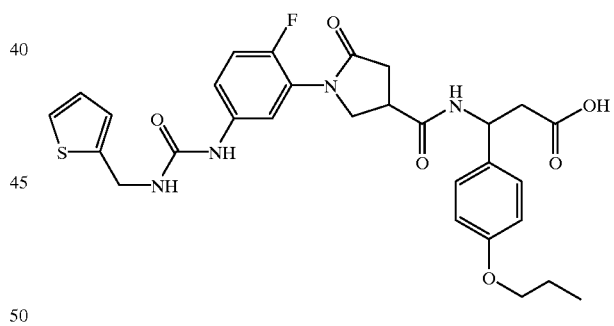

3-(4-propoxyphenyl)-3-{(1-(2-fluoro-5-{((2-thienylmethyl)amino)carbonylamino}phenyl)-5-oxopyrrolidin-3-yl)carbonylamino}propanoic acid, sodium salt The title compound was prepared analogously to Example 41. $^1$H NMR (400 MHz, MeOH-$d_4$): δ 10.6 (d, 1H), 8.87 (m, 1H), 8.84 (m, 1H), 7.48 (m, 1H), 7.33 (dd, 1H, J=3.1 Hz, 1.6 Hz), 7.22 (m, 1H), 7.06 (dt, 1H, J=10.7 Hz, 0.6 Hz, 2.2 Hz), 6.94 (m, 2H), 6.86 (dd, 2H, J=8.7 Hz, 4.5 Hz), 5.00 (dd, 1H, J=7.2 Hz, 3.4 Hz Hz), 4.34 (d, 2H, J=5.2 Hz), 3.84 (m, 1H), 3.62 (m, 2H), 3.56 (t, 2H), 3.16 (d, 2H, J=5.0 Hz), 2.52–2.64 (m, 2H), 1.55 (m, 2H), 1.26 (t, 3H). MS (ES+) 605.5 (M+Na)$^+$.

EXAMPLE 78

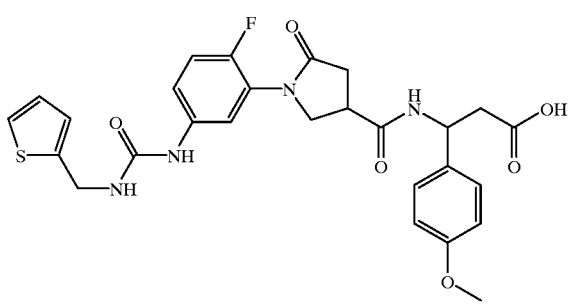

3-(4-methoxyphenyl)-3-{(1-(2-fluoro-5-{((2-thienylmethyl)amino)carbonylamino}phenyl)-5-oxopyrrolidin-3-yl)carbonylamino}propanoic acid, sodium salt The title compound was prepared analogously to Example 41. $^1$H NMR (400 MHz, DMSO-$d_6$): δ 10.9 (d, 1H), 8.97 (t, 1H), 8.84 (m, 1H), 6.88–7.95 (m, 8H), 5.12 (dd, 1H, J=7.2 Hz, 3.4 Hz Hz), 4.38 (d, 2H, J=5.3 Hz), 3.86 (m, 1H), 3.82 (s, 2H), 3.75 (s, 3H), 3.19 (d, 2H, J=5.2 Hz), 2.52–2.64 (m, 2H). MS (ES+) 577.5 (M+Na)$^+$.

EXAMPLE 79

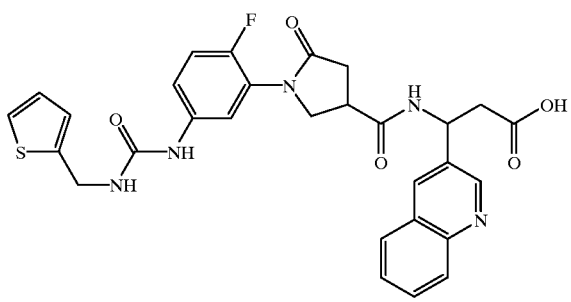

3-{(1-(2-fluoro-5-((2-thienylmethyl)amino)carbonylamino}phenyl)-5-oxopyrrolidin-3-yl)carbonylamino}-3-(3-quinolyl)propanoic acid The title compound was prepared analogously to Example 33. $^1$H NMR (400 MHz, DMSO-$d_6$): δ 10.9 (b, 1H), 9.09 (t, 1H), 8.87 (dd, 1H, J=5.1 Hz, 2.4 Hz), 8.75 (d, 1H, J=15.7 Hz), 8.56 (d, 1H, J=5.7 Hz), 8.08 (m, 1H), 7.85 (dd, 1H, J=7.9 Hz, 6.8 Hz), 7.62 (dd, 1H, J=7.3 Hz, 5.8 Hz), 7.50 (ddd, 1H, J=4.2 Hz, 3.6 Hz, 1.5 Hz), 7.38 (m, 1H), 7.25 (m, 1H), 7.15 (td, 1H, J=5.3Hz, 10.2 Hz), 6.96 (m, 1H), 5.42 (dd, 1H, J=7.3 Hz, 1.2 Hz) 4.44 (t, 2H), 3.88 (m, 1H), 3.71 (m, 1H), 3.37 (p, 1H), 2.94 (d, J=2.6 Hz), 2.67 (m, 2H). MS (ES+) 576.5 (M+H)$^+$.

EXAMPLE 80

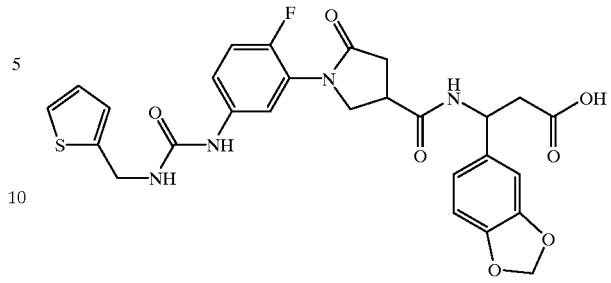

3-(1,3-benzodioxol-5-yl)-3-{(1-(2-fluoro-5-{((2-thienylmethyl)amino)carbonylamino}phenyl)-5-oxopyrrolidin-3-yl)carbonylamino}propanoic acid, sodium salt The title compound was prepared analogously to Example 41. $^1$H NMR (400 MHz, DMSO-$d_6$): δ 10.7 (b, 1H), 9.09 (dd, 1H, J=16.7 Hz, 7.8 Hz), 7.50 (m, 1H), 7.08 (dd, 1H, J=3.5 Hz, 1.3 Hz), 6.92 (dt, 1H, J=10.7 Hz, 0.6 Hz, 2.2 Hz), 6.83 (m, 2H), 6.78 (dd, 1H, J=7.1 Hz, 3.3 Hz), 6.65 (m, 2H), 5.93 (dd, 2H, J=3.8 Hz, 4.2 Hz), 5.17 (m, 1H), 4.37 (d, 2H, 5.7 Hz), 3.81 (m, 2H), 2.60 (m, 2H), 2.48 (d, 2H, J=5.2 Hz). MS (ES+) 591.5 (M+Na)$^+$.

EXAMPLE 81

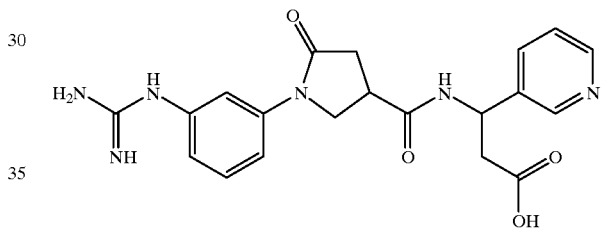

3-({1-(3-(amidinoamino)phenyl)-5-oxopyrrolidin-3-yl}carbonylamino)-3-(3-pyridyl)propanoic acid trifluoroacetate The title compound was analogously synthesized by the method described in Example 54 from ethyl 3-{(1-(3-aminophenyl)-5-oxopyrrolidin-3-yl)carbonylamino}-3-(3-pyridyl)propanoate and (tert-butoxy)-N-{((tert-butoxycarbonyl)amino)thioxomethyl}carboxamide. The title compound was obtained as white solid. MS (ES+): 411 (M+H)$^+$; (ES−): 409 (M−H)$^−$.

EXAMPLE 82

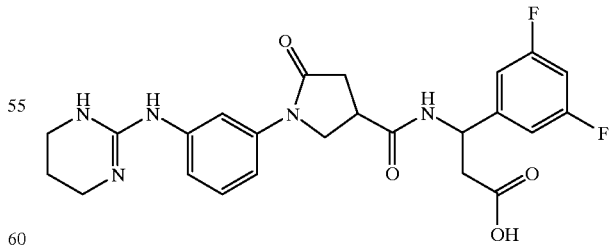

3-(3,5-difluorophenyl)-3-({5-oxo-1-(3-(3,4,5,6-tetrahydropyrimidin-2-ylamino)phenyl)pyarrolidin-3-yl}carbonylamino)propanoic acid trifluoroacetate The title compound was analogously synthesized by the method described in Example 54 from methyl 3-((1-(3- aminophenyl)-5-oxopyrrolidin-3-yl)carbonylamino)-3-(3,5-difluorophenyl)propanoate and tert-butyl 3-((tert-butyl)oxycarbonyl)-2-thioxo-1,3-diazaperhydroinecarboxylate. The title compound was obtained as a colorless solid. MS (ES+): 486 (M+H)+; (ES−): 484 (M−H)−.

EXAMPLE 83

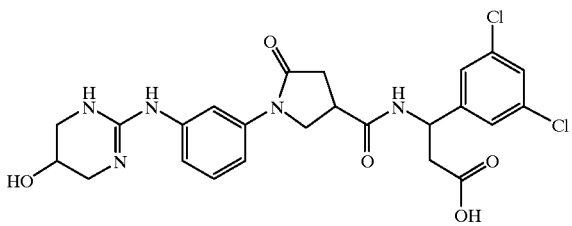

3-(3,5-dichlorophenyl)-3-((1-{3-((5-hydroxy(3,4,5,6-tetrahydropyrimidin-2-yl))amino)phenyl-5-oxopyrrolidin-3-yl)carbonylamino)propanoic acid trifluoroacetate The title compound was analogously synthesized by the method described in Example 54 from methyl 3-((1-(3-aminophenyl)-5-oxopyrrolidin-3-yl)carbonylamino)-3-(3,5-dichlorophenyl)propanoate and tert-butyl 3-((tert-butyl)oxycarbonyl)-5-(tert-butoxycarbonyloxy)-2-thioxo-1,3-diazaperhydroinecarboxylate. The title compound was obtained as a white solid. MS (ES+): 534 (M+H)+; (ES−): 432 (M−H)−.

EXAMPLE 84

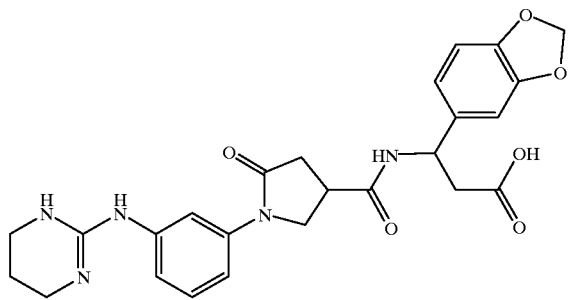

3-(2 H-benzo[3,4-d]1,3-dioxolen-5-yl)-3-({5-oxo-1-(3-(3,4,5,6-tetrahydropyrimidin-2-ylamino)phenyl)pyrrolidin-3-yl}carbonylamino)propanoic acid
Step A: phenylmethyl 1-(3-nitrophenyl)-5-oxopyrrolidine-3-carboxylate The title compound was analogously synthesized by the method described in Step A of Example 47 from 1-(3-nitrophenyl)-5-oxopyrrolidine-3-carboxylic acid. The title compound was obtained as a yellow solid. MS (ES+): 341 (M+H)+.

Step B: phenylmethyl 1-(3-aminophenyl)-5-oxopyrrolidine-3-carboxylate

The title compound was analogously synthesized by the method described in Step C of Example 28 from phenylmethyl 1-(3-nitrophenyl)-5-oxopyrrolidine-3-carboxylate The title compound was obtained as a yellow solid. MS (ES+): 311 (M+H)+.

Step C: phenylmethyl 1-(3-(aza{1,3-bis((tert-butyl)oxycarbonyl)(1,3-diazaperhydroin-2-ylidene)}methyl)phenyl)-5-oxopyrrolidine-3-carboxylate The title compound was analogously synthesized by the method described in Step B of Example 54 from phenylmethyl 1-(3-aminophenyl)-5-oxopyrrolidine-3-carboxylate and tert-butyl 3-((tert-butyl)oxycarbonyl)-2-thioxo-1,3-diazaperhydroinecarboxylate. The title compound was obtained as a white solid. MS (ES+): 593 (M+H)+.

Step D: 1-(3-(aza{1,3-bis((tert-butyl)oxycarbonyl)(1,3-diazaperhydroin-2-ylidene)}methyl)phenyl)-5-oxopyrrolidine-3-carboxylic acid To a solution of phenylmethyl 1-(3-(aza{1,3-bis((tert-butyl)oxycarbonyl)(1,3-diazaperhydroin-2-ylidene))methyl)phenyl)-5-oxopyrrolidine-3-carboxylate (1.17 g, 1.98 mmol, 1.0 eq) in THF (10 mL) and trace MeOH, was added 0.25 M $K_2CO_3$ aqeous solution (15.8 mL, 2.0 eq). The mixture was stirred at room temperature overnight. Then the solution was neutralized with 0.5 N HCl until the PH=8–9. The crude was concentrated, dried, and used in next step without further purification. MS (ES+): 503 (M+H)+; (ES−): 501 (M−H)−.

Step E: methyl 3-(2 H-benzo[3,4-d]1,3-dioxolen-5-yl)-3-({1-(3-(aza{1,3-bis((tert-butyl)oxycarbonyl)(1,3-diazaperhydroin-2-ylidene)}methyl)phenyl)-5-oxopyrrolidin-3-yl}carbonylamino)propanoate The title compound was analogously synthesized by the method described in Step B of Example 28 from methyl 3-(2 H-benzo[3,4-d]1,3-dioxolen-5-yl)-3-aminopropanoate and 1-[3-(aza{1,3-bis((tert-butyl)oxycarbonyl](1,3-diazaperhydroin-2-ylidene)}methyl)phenyl)-5-oxopyrrolidine-3-carboxylic acid. The title compound was obtained as a white solid. MS (ES+): 708 (M+H)+; (ES−) : 706 (M−H)−.

Step F: methyl 3-(2 H-benzo[3,4-d]1,3-dioxolen-5-yl)-3-({5-oxo-1-(3-(3,4,5,6-tetrahydropyrimidin-2-ylamino)phenyl)pyrrolidin-3-yl}carbonylamino)propanoate A solution of methyl 3-(2 H-benzo[3,4-d]1,3-dioxolen-5-yl)-3-({1-[3-(aza{1,3-bis[(tert-butyl)oxycarbonyl](1,3-diazaperhydroin-2-ylidene)}methyl)phenyl]-5-oxopyrrolidin-3-yl}carbonylamino)propanoate (64.7 mg, 0.09 mmol) was dissolved in $CH_2Cl_2$ (1 mL) and trifluoroacetic acid (1 mL) was stirred at room temperature overnight. Solvent was removed under reduced pressure. MS (ES+): 508 (M+H)+.

Step G: 3-(2H-benzo[3,4-d]1,3-dioxolen-5-yl)-3-({5-oxo-1-(3-(3,4,5,6-tetrahydrolyrimidin-2-ylamino)phenyl)pyrrolidin-3-yl}carbonylamino)propanoic acid The title compound was analogously synthesized by the method described in Step B of Example 9 from methyl 3-(2H-benzo[3,4-d]1,3-dioxolen-5-yl)-3-({5-oxo-1-[3-(3,4,5,6-tetrahydropyrimidin-2-ylamino)phenyl]pyrrolidin-3-yl}carbonylamino)propanoate. The title compound was obtained as a white solid. MS (ES+): 494 (M+H)+; (ES−): 492 (M−H)−.

EXAMPLE 85

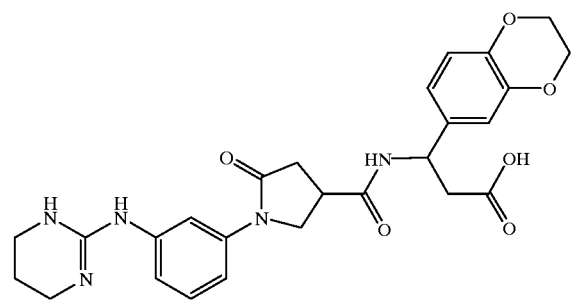

3-(2H,3 H-benzo[3,4-e]1,4-dioxin-6-yl)-3-({5-oxo-1-(3-(3,4,5,6-tetrahydropyrimidin-2-ylamino)phenyl)pyrrolidin-3-yl}carbonylamino)propanoic acid The title compound was analogously synthesized by the method described in Example 84 from methyl 3-(2H,3H-benzo[3,4-e]1,4-dioxin-6-yl)-3-aminopropanoate and 1-[3-(aza{1,3-bis[(tert-butyl)oxycarbonyl](1,3-diazaperhydroin-2-ylidene)}methyl)phenyl]-5-oxopyrrolidine-3-carboxylic acid. The title compound was obtained as a white solid. MS (ES+): 508 (M+H)$^+$.

EXAMPLE 86

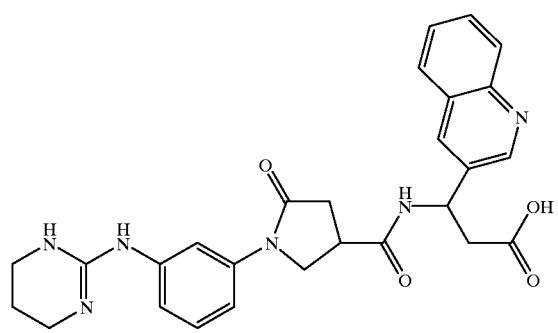

3-({5-oxo-1-[3-(3,4,5,6-tetrahydropyrimidin-2-ylamino)phenyl]pyrrolidin-3-yl}carbonylamino)-3-(3-quinolyl)propanoic acid The title compound was analogously synthesized by the method described in Example 84 from methyl 3-amino-3-(3-quinolyl)propanoate and 1-[3-(aza{1,3-bis[(tert-butyl)oxycarbonyl](1,3-diazaperhydroin-2-ylidene)}methyl)phenyl]-5-oxopyrrolidine-3-carboxylic acid. The title compound was obtained as a white solid. MS (ES+): 501 (M+H)$^+$.

EXAMPLE 87

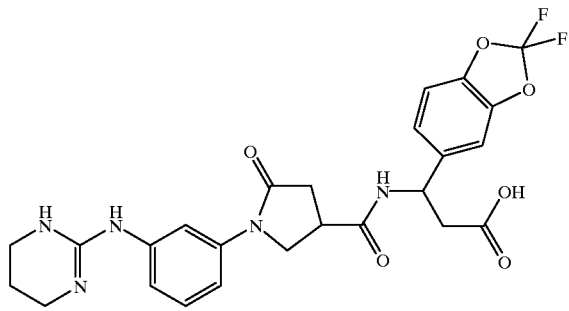

3-(2,2-difluorobenzo[3,4-d]1,3-dioxolen-5-yl)-3-({5-oxo-1-[3-(3,4,5,6-tetrahydropyrimidin-2-ylamino)phenyl]pyrrolidin-3-yl}carbonylamino)propanoic acid The title compound was analogously synthesized by the method described in Example 84 from methyl 3-amino-3-(2,2-difluorobenzo[3,4-d]1,3-dioxolen-5-yl)propanoate and 1-[3-(aza{1,3-bis[(tert-butyl)oxycarbonyl](1,3-diazaperhydroin-2-ylidene)}methyl)phenyl]-5-oxopyrrolidine-3-carboxylic acid. The title compound was obtained as a white solid. MS (ES+): 530 (M+H)$^+$.

EXAMPLE 88

Using the procedures of the above general description and the above examples, the compounds of Table 1 were prepared.

TABLE 1

| $R_1$ | $R_{15}$ | MS (M + Na)$^+$ |
|---|---|---|
| 2-thienylmethyl | 3-quinolinyl | 580.5 |
| 2-thienylmethyl | 3-pyridyl | 508.5 (M + H)$^+$ |
| benzyl | 3-quinolinyl | 574.6 |
| cyclopropylmethyl | 3-pyridyl | 488.5 |
| 2-thienylmethyl | 4-methoxyphenyl | 559.5 |
| 3-methoxyphenylmethyl | 3-pyridyl | 554.5 |
| 2-thienylmethyl | 3-ethoxy-4-methoxyphenyl | 581.5 (M + H)$^+$ |
| 2-furylmethyl | 3-pyridyl | 514.5 |
| 2-thienylmethyl | 3-fluoro-4-methoxyphenyl | 577.5 |
| 2-thienylmethyl | 3-fluorophenyl | 547.0 |
| 3-fluorophenylmethyl | 3-pyridyl | 520.5 (M + H)$^+$ |
| 2-biphenylmethyl | 3-pyridyl | 600.5 |
| 2-chlorophenylmethyl | 3-pyridyl | 558.0 |
| 2,4-dichlorophenylmethyl | 3-pyridyl | 592.0 |
| CF$_3$—CH$_2$— | 3-pyridyl | 494.5 (M + H)$^+$ |
| 2-thienylmethyl | 3,5-difluorophenyl | 565.0 |
| 2-methylphenylmethyl | 3-pyridyl | 538.5 |
| 5-methylfur-2-ylmethyl | 3-pyridyl | 528.5 |
| 3-methylphenylmethyl | 3-pyridyl | 516.5 (M + H)$^+$ |
| 3-methylbutyl | 3-pyridyl | 504.5 |
| benzyl | 3,5-dimethoxyphenyl | 583.5 |
| 2-(CF$_3$)phenylmethyl | 3-pyridyl | 592.5 |
| CF$_3$—CF$_2$—CH$_2$— | 3-pyridyl | 544.5 (M + H)$^+$ |
| 3-(CF$_2$)phenylmethyl | phenyl | 592.5 |
| 2-fluorophenylmethyl | 3-pyridyl | 542.5 |
| benzyl | phenyl | 523.5 |
| CF$_3$—CF$_2$—CF$_2$—CH$_2$— | 3-pyridyl | 594.5 (M + H)$^+$ |
| 4-chlorophenylmethyl | 3-pyridyl | 558.0 |
| 3-(CF$_3$O)phenylmethyl | 3-pyridyl | 586.5 (M + H)$^+$ |
| 2-methoxyphenylmethyl | 3-pyridyl | 554.5 |
| cyclohexylmethyl | 3-pyridyl | 530.5 |
| 3-chlorophenylmethyl | 3-pyridyl | 536.5 (M + H)$^+$ |
| benzyl | 4-ethylphenyl | 551.5 |
| 3,3-dimethylbutyl | 3-pyridyl | 518.5 |
| benzyl | cyclopropyl | 465.5 (M + H)$^+$ |
| 4-(CF$_3$)phenylmethyl | phenyl | 592.5 |
| 2,4-difluorophenylmethyl | 3-pyridyl | 538.5 (M + H)$^+$ |
| 3,4-dichlorophenylmethyl | 3-pyridyl | 569.0 (M + H)$^+$ |
| benzyl | cyclohexyl | 529.5 |
| benzyl | 4-(CF$_3$O)phenyl | 607.5 |
| benzyl | 3-thienyl | 529.0 |
| 2-thienylmethyl | 3,4-dimethoxyphenyl | 589.5 |

Using the procedures of the above general description and the above examples, the compounds of Tables 2–6 can be prepared.

TABLE 2

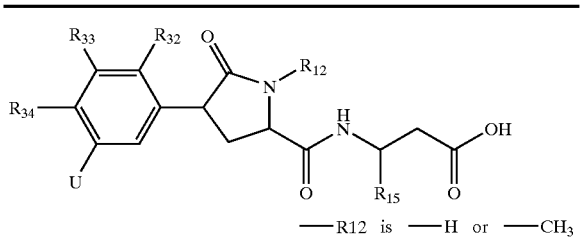

—R12 is —H or —CH₃

| U | $R_{15}$ | $R_{32}$ | $R_{33}$ | $R_{34}$ |
|---|---|---|---|---|
| PhCH₂NHC(O)NH— | 3-pyridylNHSO₂— | F | H | H |
| butylNHC(O)NH— | 3,4-(F)₂Ph— | CF₃ | H | H |
| 2-thienyl-CH₂NHC(O)NH— | 3-pyridyl | MeO | H | H |
| 3-pyridyl-CH₂NHC(O)NH— | 4-pyridyl | H | H | MeS |
| 2-pyridyl-NH— | 3-quinolinyl | H | H | Me |

TABLE 2-continued

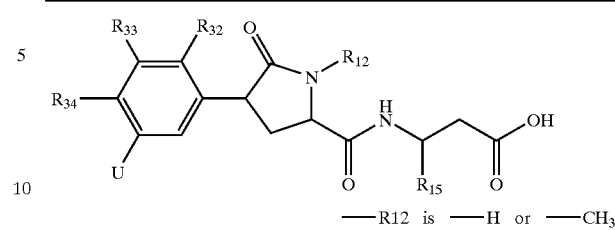

—R12 is —H or —CH₃

| U | $R_{15}$ | $R_{32}$ | $R_{33}$ | $R_{34}$ |
|---|---|---|---|---|
| imidazolin-2-yl-NH— | 3,4,5-(MeO)₃Ph— | H | H | Cl |
| 1,3-oxazolin-2-yl-NH— | 3-pyridylCONH— | MeO | MeO | H |
| 3-(MeO)Ph—CH₂NHCO₂— | 3-ClPhCH₂— | Me | H | F |
| NH₂C(NCH₃)NH— | PhNHSO₂— | H | H | H |
| 2-(6-amino-pyrid-2-yl)ethylthio- | 2-(3-quinolinyl)ethyl | H | CO₂H | H |

TABLE 3

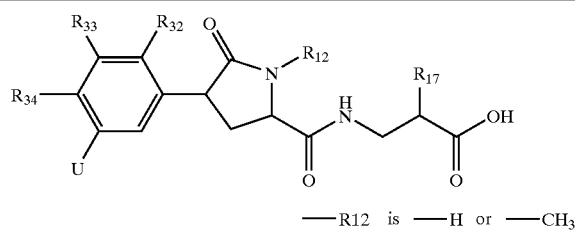

—R12 is —H or —CH₃

| U | $R_{17}$ | $R_{32}$ | $R_{33}$ | $R_{34}$ |
|---|---|---|---|---|
| PhCH₂NHC(O)NH— | 3-pyridylSO₂NH— | H | H | F |
| butylNHC(O)NH— | 3,4-(F)₂PhNHSO₂— | H | H | CF₃ |
| 2-thienyl-CH₂NHC(O)NH— | 3-(3-pyridyl)-propyl | H | H | MeO |
| 3-pyridyl-CH₂NHC(O)NH— | 4-pyridyl | MeS | H | H |
| 2-pyridyl-NH— | 3-quinolinyl | Me | H | H |
| imidazolin-2-yl-NH— | 3,4,5-(MeO)₃Ph— | Cl | H | H |
| 1,3-oxazolin-2-yl-NH— | 3-pyridylCONH— | Me | Me | H |
| 3,4-(MeO)₂Ph—CH₂NHCO₂— | 3-ClPhCH₂— | H | 4-MeOPh | H |
| NH₂C(NCH₃)NH— | PhSO₂NH— | H | H | H |
| 2-(6-aminopyrid-2-yl)ethoxy- | 2-(3-quinolinyl)ethyl | H | H | H |

TABLE 4

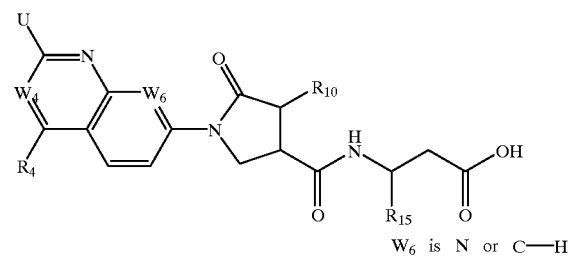

$W_6$ is N or C—H

| U | $R_{15}$ | $R_4$ | $R_{10}$ | $W_4$ |
|---|---|---|---|---|
| PhCH₂NH— | 3-pyridyl | H | Me | C—H |
| 2-pyridyl-NH— | 3,4-(Cl)₂Ph— | H | H | C—OMe |
| 3,4,5,6-tetrahydropyrimidin-2-yl-NH— | 3-pyridylmethyl | Me | Et | C—H |
| 1,3-oxazolin-2-yl-NH— | 4-pyridyl | MeO | H | N |
| 3,4-(MeO)₂Ph—CH₂NHCO₂— | 3-quinolinyl-methyl | H | Me | C—H |
| NH₂C(NCH₃)NH— | 3,5-(MeO)₂Ph— | F | H | C—H |

TABLE 4-continued

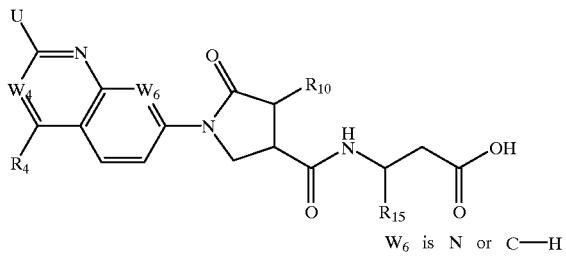

W$_6$ is N or C—H

| U | R$_{15}$ | R$_4$ | R$_{10}$ | W$_4$ |
|---|---|---|---|---|
| 2-pyridyl-NH— | 3-pyridylNHCO— | Ph | Et | N |
| PhNH— | 3-(Me$_2$N)PhCH$_2$— | Cl | H | N |
| 4-(F)Ph—NH— | Ph— | H | Me | C—H |
| isopropyl-NH— | 3-quinolinyl | OH | H | C—H |

TABLE 5

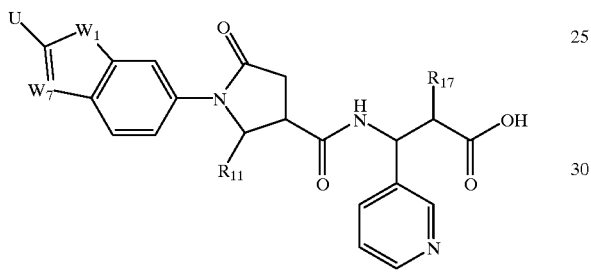

| U | W$_1$ | W$_7$ | R$_{11}$ | R$_{17}$ |
|---|---|---|---|---|
| PhCH$_2$NH— | NH | C—CH$_3$ | H | H |
| 2-pyridyl-NH— | O | C—H | H | H |
| imidazolin-2-yl-NH— | S | C—H | Me | Me |
| 1,3-oxazolin-2-yl-NH— | N—CH$_3$ | C—H | Me | Et |
| 4-(F)Ph—CH$_2$NHCO$_2$— | NH | C—H | H | Me |
| NH$_2$C(NCH$_3$)NH— | NH | C—H | H | H |
| 2-pyridyl-NH— | NH | C—H | Me | H |
| PhNH—CO | O | N | Et | H |
| 4-(F)Ph—NH— | NH | C—CF$_3$ | H | H |
| isopropyl-NH— | NH | N | H | Me |
| 5-Me-thien-2-yl-CH$_2$NH— | NH | C—H | H | Me |
| Me$_2$NCH$_2$CH$_2$O— | NH | N | Me | H |

TABLE 6

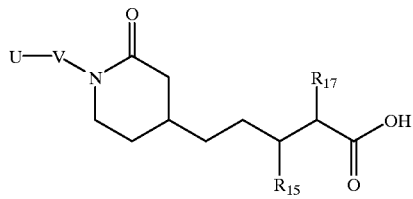

| U—V— | R$_{15}$ | R$_{17}$ |
|---|---|---|
| 2-(PhCH$_2$NHC(O)NH)pyrrol-5-yl | 3-pyridyl | H |
| 4-(butylNHC(O)NH)pyrimid-2-yl | 3,4-(Cl)$_2$Ph— | Et |
| 4-(2-thienyl-CH$_2$NHC(NH)NH)phenyl- | 6-Cl-3-pyridyl-CH$_2$— | Me |
| 2-(3-pyridyl-CH$_2$NHC(S)NH)fur-4-yl | H | 6-Me-3-pyridylSO$_2$NH— |
| 6-(2-pyridyl-NH)pyrid-2-yl | 3-quinolinyl-CH$_2$— | H |

TABLE 6-continued

| U—V— | R$_{15}$ | R$_{17}$ |
|---|---|---|
| 7-(imidazolin-2-yl-NH)quinolin-2-yl | H | 3,4-(F)$_2$PhNHSO$_2$— |
| 1-(1,3-oxazolin-2-yl-NH—CH$_2$CH$_2$)indol-3-yl | 6-MeO-3-pyridylCONH— | H |
| 1-(3-(MeO)PhCH$_2$NHCO$_2$)-8-(MeO)naphth-3-yl | 3-(Me$_2$N)PhCH$_2$CH$_2$— | H |
| 3-(1,2,3,4-tetrahydro-1,8-naphthyridin-7-ylmethoxy)4-(F)phenyl | H | 3-pyridyl-CH$_2$CH$_2$CH$_2$— |
| 3-(2-(6-aminopyrid-2-yl)ethylthio)phenyl | 3-quinolinyl | 4-pyridyl |
| 1-(3-pyridyl-CH$_2$NHC(O)NH)isoquinolin-3-yl | H | 3-quinolinyl-CH$_2$CH$_2$— |
| 6-(2-pyridyl-NH)benzofur-2-yl | 5-pyrimidyl | H |
| 6,6-(Me)$_2$-4-(imidazolin-2-yl-NH—CH$_2$CH$_2$O)-5-aza-6,7-dihydroindol-2-yl | Me | 3-pyridyl-CH$_2$CONH— |
| 6-(1,3-oxazolin-2-yl-NH)-7-aza-4,5-dihydroindol-2-yl | 4-imidazolyl | H |
| 5-carboxy-3-(3-(MeO)Ph—CH$_2$NHCO$_2$)phenyl | H | PhCH$_2$CH$_2$—SO$_2$NH— |
| 3-(NH$_2$C(NCH$_3$)NH—CH$_2$CH$_2$—NHCOCH$_2$)phenyl | 5-CF$_3$-3-thienyl | 2-propyl |

TABLE 7

| U—V— | R$_{15}$ | R$_{17}$ |
|---|---|---|
| 2-(PhCH$_2$NHC(O)NH)pyrrol-5-yl | 3-pyridyl | H |
| 4-(butylNHC(O)NH)pyrimid-2-yl | 3,4-(Cl)$_2$Ph— | Et |
| 4-(2-thienyl-CH$_2$NHC(NH)NH)phenyl- | 6-Cl-3-pyridyl-CH$_2$— | Me |
| 2-(3-pyridyl-CH$_2$NHC(S)NH)fur-4-yl | H | 6-Me-3-pyridylSO$_2$NH— |
| 6-(2-pyridyl-NH)pyrid-2-yl | 3-quinolinyl-CH$_2$— | H |
| 7-(imidazolin-2-yl-NH)quinolin-2-yl | H | 3,4-(F)$_2$PhNHSO$_2$— |
| 1-(1,3-oxazolin-2-yl-NH—CH$_2$CH$_2$)indol-3-yl | 6-MeO-3-pyridylCONH— | H |
| 1-(3-(MeO)PhCH$_2$NHCO$_2$)-8-(MeO)naphth-3-yl | 3-(Me$_2$N)PhCH$_2$CH$_2$— | H |
| 3-(1,2,3,4-tetrahydro-1,8-naphthyridin-7-ylmethoxy)4-(F)phenyl | H | 3-pyridyl-CH$_2$CH$_2$CH$_2$— |
| 3-(2-(6-aminopyrid-2-yl)ethylthio)phenyl | 3-quinolinyl | 4-pyridyl |
| 1-(3-pyridyl-CH$_2$NHC(O)NH)isoquinolin-3-yl | H | 3-quinolinyl-CH$_2$CH$_2$— |
| 6-(2-pyridyl-NH)benzofur-2-yl | 5-pyrimidyl | H |
| 6,6-(Me)$_2$-4-(imidazolin-2-yl-NH—CH$_2$CH$_2$O)-5-aza-6,7-dihydroindol-2-yl | Me | 3-pyridyl-CH$_2$CONH— |
| 6-(1,3-oxazolin-2-yl-NH)-7-aza-4,5-dihydroindol-2-yl | 4-imidazolyl | H |
| 5-carboxy-3-(3-(MeO)Ph—CH$_2$NHCO$_2$)phenyl | H | PhCH$_2$CH$_2$—SO$_2$NH— |
| 3-(NH$_2$C(NCH$_3$)NH—CH$_2$CH$_2$—NHCOCH$_2$)phenyl | 5-CF$_3$-3-thienyl | 2-propyl |

TABLE 8 q is 1 or 2

| U | —X$_1$—Y$_1$—Z— | E |
|---|---|---|
| PhCH$_2$NHC(O)NH— | —N—C(O)—O— | 1-tetrazolyl |
| butylNHC(O)NH— | —C(H)—C(O)—N(CH$_3$)— | —CO$_2$Et |
| 2-thienyl-CH$_2$NHC(NH)NH— | —C(H)—S(O)$_2$—NH— | —CO$_2$H |
| 6-NH$_2$-pyrid-3-yl-CH$_2$NHC(S)NH— | —N—C(O)—C(CH$_3$)$_2$—O— | —C(O)—NH—S(O)$_2$—(4-MeOPh) |
| 2-pyridyl-NH— | —N—C(O)—CH$_2$—C(CH$_3$)$_2$— | —C(O)—NH—CH$_2$CH$_2$CO$_2$H |
| 2-imidazolinyl-NH— | —C(H)—S(O)$_2$—N(CH$_3$)— | —CO$_2$H |

TABLE 8-continued

[Structure diagram: U-phenyl-X1(Y1-Z ring with q CH2)-C(O)-NH-CH(CH2-pyridyl)-E]

q is 1 or 2

| U | —X$_1$—Y$_1$—Z— | E |
|---|---|---|
| 1,3-oxazolin-2-yl-NH—CH$_2$CH$_2$— | —C(H)—C(O)—CH(CH$_3$)—O— | —C(O)—NH—CH(CH$_2$CH$_2$CO$_2$H)—CO$_2$H |
| 3-(MeO)PhCH$_2$NHCO$_2$— | —N—C(S)—CH$_2$— | —CO$_2$CH$_2$CO$_2$H |
| 1,2,3,4-tetrahydro-1,8-naphthyridin-7-ylmethoxy- | —N—S(O)$_2$—NH— | —C(O)—NH—S(O)—CH$_2$CH(NH$_2$)—CO$_2$H |
| 2-(6-aminopyrid-2-yl)ethylthio- | —C(H)—S(O)—NH— | —C(O)—NH—C(O)—CH(NH$_2$)—CH$_2$CO$_2$H |
| 3-pyridyl-CH$_2$NHC(O)NH— | —N—C(O)—NH—CH$_2$— | —C(O)—NH—CH(CH$_2$OH)—CO$_2$H |
| 2-pyridyl-NH— | —N—C(O)—N(CH$_3$)— | —CO$_2$(2-(HO)Ph) |
| 2-imidazolinyl-NH—CH$_2$CH$_2$O— | —N—S(O)$_2$—CH$_2$—NH— | —C(O)—NH-(4-(NO$_2$)Ph) |
| 1,3-oxazolin-2-yl-NH— | —C(H)—C(O)—CH(CH$_3$)—N(butyl)- | —C(O)—NH—C(O)-piperidin-1-yl |
| 3-(MeO)Ph—CH$_2$NHCO$_2$— | —N—C(O)—CH$_2$—NH— | —CO$_2$CH$_2$(4-MeO)Ph) |
| NH$_2$C(NCH$_3$)NH—CH$_2$CH$_2$—NHCOCH$_2$O— | —N—S(O)$_2$—C(CH$_3$)$_2$—CH$_2$— | —C(O)—NH—CH(CH$_2$-imidazol-4-yl)-CO$_2$H |

TABLE 9

[Structure diagram: U-phenyl-N(piperazinone)-N-X3-C(O)-N(NH)-X4-CH(R15)-CO2H]

| U | R$_{15}$ | X$_3$ | X$_4$ |
|---|---|---|---|
| PhCH$_2$NH— | 3-pyridylC(O)NH— | CH$_2$ | CH$_2$ |
| 2-pyridyl-NH— | 3,4-(Cl)$_2$Ph—S(O)$_2$NH— | bond | CH$_2$CH$_2$ |
| 3,4,5,6-tetrahydropyrimidin-2-yl-NH— | 3-pyridylmethyl-NHC(O)NH— | CH$_2$CH$_2$ | CH$_2$ |
| 1,3-oxazolin-2-yl-NH— | 2-(NH$_2$)-4-pyridyl-C(O)NH | CH$_2$ | CH(CH$_3$) |
| 3,4-(MeO)$_2$Ph—CH$_2$NHCO$_2$— | 3-quinolinyl-methyl-O$_2$C—NH— | bond | CH(CH$_3$)CH$_2$ |
| NH$_2$C(NCH$_3$)NH— | 3,5-(MeO)$_2$Ph— | CH$_2$CH$_2$ | bond |
| 2-pyridyl-NH— | 3-pyridylNHCO— | CH(CH$_3$) | bond |
| PhNH— | 3-(Me$_2$N)PhCH$_2$— | CH$_2$ | CH$_2$ |
| 4-(F)Ph—NH— | 3-quinolinyl-NHS(O)$_2$NH— | CH$_2$ | CH$_2$C(CH$_3$)$_2$ |
| isopropyl-NH— | 3-quinolinyl | CH$_2$CH$_2$CH$_2$ | bond |

EXAMPLE 90

Biological Studies

The following assays can be used to characterize the biological activity properties of compounds of the invention. Purified integrin $\alpha_v\beta_3$ may be obtained using the methods of Marcinkiewicz et al. (Protein Expression Purif. 8:68–74, 1996) and Pytela et al. (Meth. Enzymol. 144:475–489, 1987). Purified integrin $\alpha_v\beta_5$ may be obtained using the methods of Smith et al. (J. Biol. Chem. 265:11008–13, 1990). Purified integrin $\alpha_v\beta_6$ may be obtained using the methods of Busk et al. (J. Biol. Chem. 267:5790–6, 1992).

Primary human umbilical cord endothelial cells (HUVEC) can be used to show that the compounds of the invention inhibit cellular proliferation and/or cellular adhesion.

HUVEC Proliferation Assay

1. Coat 3 NUNC polystyrene 96 well plate (VWR, 62409-120; lids 62409-118) with vitronectin (purified internally), fibronectin (Collaborative Biomed 40008 A) or fibrinogen (Calbiochem 341578) 50 ng/well in 50 µl PBS, 1 hr @RT.
2. Trypsinize HUVEC's:
   a. rinse with 5 mls PBS (no Ca, Mg)
   b. 2 ml trypsin, remove
   c. 10 ml growth medium
3. Rinse vitronectin plates 1× in 200 µl PBS −/− and add 3000 cells per well in 100 ul growth medium (EBM2 (Clonetics, CC-3156)+EGM2 bullet kit (CC-4176)).
4. Incubate 24 hours at 37° C. to allow attachment.
5. Remove growth medium and add 100 µl growth medium+drugs (25 µM and down by five fold steps in DMSO-0.25% final DMSO concentration).
6. Incubate for 3 days changing media (+drugs).
7. Remove non-adherent cells on Friday with Raindance 12 well plate washer.
8. Wash twice with 200 µl PBS (+Mg & Ca).
9. Tap out excess liquid.
10. Freeze @ −70° C. for 30 minutes.
11. Thaw plate and add 150 µl CyQuant fluorescent dye (Molecular Probes C-7026).
12. Read after 4 minutes @ 485 λ (excitation), 530 λ (emission).

HUVEC Adhesion Assay

1. Coat 2 NUNC polystyrene 96 well plates (VWR, 62409-120; lids 62409-118) with 50 µl vitronectin (purified internally) at 50 ng/well in PBS (-Mg & Ca), for 1 hour @ 37° C.
2. Rinse with PBS & block with 150 µl PBS/1% BSA (Sigma A8918), 1 hour at @ 37° C.
3. Prepare drug dilutions:
   a. 400 fold concentrate in 100% DMSO
   b. 0.25% DMSO [assay]$_{final}$
   c. 10 mM & down (25 µM$_{final}$ & down)
   d. dilute 1 µl of 400 fold conc into 200 µl adhesion media
   e. use 50 µl/well
4. Trypsinize HUWEC's:
   a. rinse with 5 ml PBS (no Ca, Mg)
   b. 2 ml trypsin, remove
   c. 10 ml growth medium
5. Spin @ 1200 rpm for 10 minutes.
6. Rinse blocking buffer from assay plate and add 50 µl of drug dilutions.
7. Resuspend cells in adhesion media, count and add 2e4 cells/well in 50 µl (4e5/ml).
8. Incubate 60 minutes @ 37° C.
9. Remove non-adherent cells with Raindance 12 well plate washer.
10. Wash twice with 200 µl PBS (+Mg & Ca)
11. Tap out excess liquid.
12. Freeze @ -70° C. for 30 minutes to overnite.
13. Thaw plate and add 150 µl CyQuant fluorescent dye (Molecular Probes C-7026).
14. Read after 2–5 minutes @ 485 λ (excitation), 530 λ (emission).

Adhesion medium: Media 199 (which contains 36 mM CaCl$_2$ and 0.8 mM MgSO$_4$), 0.5% BSA, 10 mM HEPES, 1 mM MgCl$_2$, and 1 mM MnCl$_2$

Intecfrin Binding Assay

Purification of Vitronectin

Vitronectin was prepared from out-dated human plasma as described by Yatohgo et al. (Cell Struct. Funct. 13:281–292, 1988) with modifications. Normal human blood collected in citrate tubes was centrifuged and clotted overnight with the addition of CaCl$_2$. The clot was centrifuged, filtered at 0.45 µm, and applied to a Heparin Sepharose column that was equilibrated with 10 mM NaPO$_4$, 5 mM EDTA, 0.13 M NaCl pH 7.7. The column flow through was collected as a single pool, urea was added to a final concentration of 8 M, and mixed overnight. The sample was then incubated with Heparin Sepharose which had been equilibrated with 10 mM NaPO$_4$, 5 mM EDTA, 8 M urea pH 7.7 (buffer A) overnight. The Heparin Sepharose was separated from the liquid by centrifugation and washed once with buffer A, buffer A+0.13 M NaCl, and buffer A+0.13 NaCl and 10 mM BME. The vitronectin was eluted from the column with buffer A+0.5 M NaCl. The fractions containing Vitronectin were buffer exchanged into PBS and stored at -70° C.

Ruthenylation of Vitronectin and Fibrinogen

Purified human vitronectin or purified human fibrinogen (Calbiochem) was dialyzed into 50 mM borate, 100 mM NaCl pH 8.0. A stock solution of ruthenium (II) tris bipyridine N-hydroxysuccinimide ester (Origen TAG® Ester, Igen Inc. Gaithersburg, Md.) was freshly prepared by adding 50 µL DMSO to 150 µg of the Origen TAG-NHS ester. Fifty microliters of the Origen TAG-NHS ester was added to one fifth molar ratio of the matrix protein. After one hour incubation at 25° C., the reaction was quench by the addition of 50 µL of 2 M glycine. Unincorporated ruthenium and excess glycine were removed by dialysis into PBS, 0.05% NaN$_3$. Protein concentrations were determined using Micro-BCA (Pierce, Rockford, Ill.). Origen TAG incorporation was assessed at 455 nm (e=13,700 M$^{-1}$cm$^{-1}$). Vitronectin-Ru and Fibrinogen-Ru were stored at -70° C. until needed.

Purification of Platelet Fibrinogen Receptor αIIbβ3

Twelve units of outdated platelets were washed with PBS and centrifuged at low speed to remove RBCs. The washed platelets were lysed in, 20 mM Tris-HCl pH 7.4, 140 mM NaCl, 2 mM CaCl$_2$, 1 mM pefabloc, 3% octylglucoside with gentle stirring for two hours at 4° C. The lysate was centrifuged at 100,000×g for 1 hour to pellet insoluble cellular debris. The resulting supernatant was applied to a lentil lectin (EY labs) column and washed with lysis buffer containing 1% octylglucoside (binding buffer) until a stable UV baseline was reached. Purified αIIbβ3 was eluted from the column with binding buffer containing 10% dextrose. Purified αIIbβ3 was stored at -70° C. until needed.

Purification of αvβ3 and αvβ5

Frozen placentas were thawed overnight at 4° C., cut into 1 cm sections, and washed with 50 mM Tris-HCl, 100 mM NaCl, 1 mM PMSF pH 7.5 (buffer A). The placentas were then incubated overnight in buffer A with the addition of 3% (w/v) octyglucoside. Extracted protein was separated from whole tissue by centrifugation. The extract was then 0.45 µm filtered and NaN$_3$ was added to a final concentration of 0.02%. The sample was then loaded on to an anti-αvβ3 or anti-αvβ5 affinity column, washed with buffer A plus 1% (w/v) octylglucoside, and eluted with Gentle Elution Buffer (Pierce). The fractions containing αvβ3 or αvβ5 were exchanged into buffer A plus 1% octylglucoside and stored at -70° C. Purified αvβ3 and αvβ5 were also purchased from Chemicon International Inc.

Incorporation of αvβ3, αvβ5, or αIIbβ3 on paramagnetic beads

αvβ3, αvβ5, or αIIbβ3 paramagnetic beads were prepared from 4.5µ uncoated Dynabeads® (Dynal®, Lake Success, N.Y.). Uncoated Dynabeads® were washed three times in phosphate buffered saline pH 7.4 (PBS) and resuspended in 50 mM Tris-HCl, 100 mM NaCl, 1 mM MgCl$_2$, 1 mM CaCl$_2$, and 1 mM MnCl$_2$ pH 7.5 (Buffer A). Purified receptor αvβ3, αvβ5 (Chemicon), or αIIbβ3 were quickly diluted in buffer A and added to the uncoated Dynabeads® at a ratio of 50 µg protein to 10$^7$ beads. The bead suspension was incubated with agitation overnight at 4° C. The beads were washed three times in buffer A, 0.1% bovine serum albumin (BSA) and resuspended buffer A+3% BSA. After three hours at 4° C. the beads were wash three times in Buffer A, 1% BSA, 0.05% azide and stored at -70° C. until needed.

Solid Phase Binding Assay

All compounds were dissolved and serially diluted in 100% DMSO prior to a final dilution in assay buffer (50 mM Tris-HCl pH 7.5, 100 mM NaCl, 1 mM CaCl$_2$, 1 mM MgCl$_2$, 1 mM MnCl$_2$, 1% BSA, 0.05% Tween-20) containing Vitronectin-Ru or Fibrinogen-Ru and appropriate integrin coated paramagnetic beads. The assay mixture was incubated at 25° C. for two hours with agitation and subsequently read on an Origen Analyzer® (Igen Inc. Gaithersburg, Md.) Non-specific binding was determined using 1 µM Vitronectin, 1 µM Fibrinogen or 5 mM EDTA. The data was prepared using a four-parameter fit by the Levenburg Marquardt algorithm (XLfit® ID Business Solutions.) Ki values were calculated using the equation of Cheng and Prusoff (Biochem. Pharmacology 22:3099–3108, 1973).

The following compounds exhibit activities in the binding assay with $IC_{50}$ values of 30 μM or less:

3-((5-oxo-1-{3-((N-phenylcarbamoyl)amino)phenyl}pyrrolidin-3-yl)carbonylamino)-3-(3-pyridyl)propanoic acid;

3-{(5-oxo-1-(3-{(N-(2-phenylethyl)carbamoyl)amino}phenyl)pyrrolidin-3-yl)carbonylamino}-3-(3-pyridyl)propanoic acid;

3-({1-[3-({N-((4-methoxyphenyl)methyl)carbamoyl}amino)phenyl]-5-oxopyrrolidin-3-yl}carbonylamino)-3-(3-pyridyl)propanoic acid;

3-((1-{3-((N-methylcarbamoyl)amino)phenyl}-5-oxopyrrolidin-3-yl)carbonylamino)-3-(3-pyridyl)propanoic acid;

3-((1-{3-((N-butylcarbamoyl)amino)phenyl}-5-oxopyrrolidin-3-yl)carbonylamino)-3-(3-pyridyl)propanoic acid;

3-((1-{3-((N-hexylcarbamoyl)amino)phenyl}-5-oxopyrrolidin-3-yl)carbonylamino)-3-(3-pyridyl)propanoic acid;

3-((5-oxo-1-{3-((N-propylcarbamoyl)amino)phenyl}pyrrolidin-3-yl)carbonylamino)-3-(3-pyridyl)propanoic acid;

3-{(1-(3-{(N-(1-methylethyl)carbamoyl)amino}phenyl)-5-oxopyrrolidin-3-yl)carbonylamino}-3-(3-pyridyl)propanoic acid;

3-({5-oxo-1-(3-(1,3-thiazolin-2-ylamino)phenyl)pyrrolidin-3-yl}carbonylamino)-3-(3-pyridyl)propanoic acid;

3-({1-(3-(2-imidazolin-2-ylamino)phenyl)-5-oxopyrrolidin-3-yl}carbonylamino)-3-(3-pyridyl)propanoic acid;

3-{(5-oxo-1-(3-{((N-phenylcarbamoyl)methyl)amino}phenyl)pyrrolidin-3-yl)carbonylamino}-3-(3-pyridyl)propanoic acid;

3-({5-oxo-1-(3-(3-pyridylcarbonylamino)phenyl)pyrrolidin-3-yl}carbonylamino)-3-(3-pyridyl)propanoic acid;

3-({5-oxo-1-(3-(phenylcarbonylamino)phenyl)pyrrolidin-3-yl}carbonylamino)-3-(3-pyridyl)propanoic acid;

3-{(5-oxo-1-(3-{(benzylamino)carbonylamino}phenyl)pyrrolidin-3-yl)carbonylamino}-N-(phenylsulfonyl)-3-(3-pyridyl)propanamide;

3-({5-oxo-1-(3-({(benzylamino)thioxomethyl}amino)phenyl)pyrrolidin-3-yl}carbonylamino)-3-(3-pyridyl)propanoic acid;

3-((1-{3-(({((4-fluorophenyl)methyl)amino}thioxomethyl)amino)phenyl}-5-oxopyrrolidin-3-yl)carbonyl amino)-3-(3-pyridyl)propanoic acid;

3-({1-(3-({((2-furylmethyl)amino)thioxomethyl}amino)phenyl)-5-oxopyrrolidin-3-yl}carbonylamino)-3-(3-pyridyl)propanoic acid;

3-({1-(3-({((3-methylbutyl)amino)thiooxomethyl}amino)phenyl)-5-oxopyrroidin-3-yl}carbonylamino)-3-(3-pyridyl)propanoic acid;

3-{(1-(3-{((butylamino)thioxomethyl)amino}phenyl)-5-oxopyrrolidin-3-yl)carbonylamino}-3-(3-pyridyl)propanoic acid;

3-({5-oxo-1-(3-(piperidylcarbonylamino)phenyl)pyrrolidin-3-yl}carbonylamino)-3-(3-pyridyl)propanoic acid;

3-{(1-{3-((N-(1,3-benzodioxol-5-ylmethyl)aminocarbonyl)amino}phenyl}-5-oxopyrrolidin-3-yl)carbonylamino}-3-(3-pyridyl)propanoic acid;

3-{(1-(2-methyl-5-((benzylamino)carbonylaminol)phenyl)-5-oxopyrrolidin-3-yl)carbonylamino}-3-(3-pyridyl)propanoic acid;

3-{(1-(4-fluoro-5-{(benzylamino)carbonylamino}phenyl)-5-oxopyrrolidin-3-yl)carbonylamino}-3-(3-pyridyl)propanoic acid;

3-{(5-oxo-1-(3-((benzylamino)carbonylamino}-5-(trifluoromethyl)phenyl)pyrrolidin-3-yl)carbonylamino}-3-(3-pyridyl)propanoic acid;

3-{(1-(2-methoxy-5-{(benzylamino)carbonylamino}phenyl)-5-oxo-pyrolidin-3-yl)carbonylamino}-3-(3-pyridyl)propanoic acid;

3-{(1-(2-fluoro-5-{(benzylamino)carbonylamino}phenyl)-5-oxopyrrolidin-3-yl)carbonylamino}-3-(3-pyridyl)propanoic acid;

3-{(1-(2-chloro-5-{(benzylamino)carbonylamino}phenyl)-5-oxopyrrolidin-3-yl)carbonylamino}-3-(3-pyridyl)propanoic acid;

3-{(1-(4-chloro-3-{(benzylamino)carbonylamino}phenyl)-5-oxo-pyrolidin-3-yl)carbonylamino}-3-(3-pyridyl)propanoic acid;

3-{(1-(3-{(2-methoxyethylamino)carbonylamino}phenyl)-5-oxopyrrolidin-3-yl)carbonylamino}-3-(3-pyridyl)propanoic acid;

3-{(1-(4-methyl-3-{(benzylamino)carbonylamino}phenyl)-5-oxo-pyrolidin-3-yl)carbonylamino}-3-(3-pyridyl)propanoic acid;

3-((5-oxo-1-{3-((2-pyridylamino)methyl)phenyl}pyrrolidin-3-yl)carbonylamino}-3-(3-quinolyl)propanoic acid;

3-(3-Fluorophenyl)-3-{(5-oxo-1-(3-{(benzylamino)carbonylamino}phenyl)pyrrolidin-3-yl)carbonylamino}propanoic acid;

3-(3,5-difluorophenyl)-3-{(5-oxo-1-(3-{(benzylamino)carbonylamino}phenyl)pyrrolidin-3-yl)carbonylamino}propanoic acid;

3-(3,5-dichlorophenyl)-3-{(5-oxo-1-(3-{(benzylamino)carbonylamino}phenyl)pyrrolidin-3-yl)carbonylamino}propanoic acid;

3-(3,5-dichloro-2-hydroxyphenyl)-3-{(5-oxo-1-(3-{(benzylamino)carbonylamino}phenyl)pyrrolidin-3-yl)carbonylamino}propanoic acid;

3-(3,5-dichloro-2-hydroxyphenyl)-3-{(5-oxo-1-(3-{((2-thienylmethyl)amino)carbonylamino}phenyl)pyrrolidin-3-yl)carbonylamino}propanoic acid;

3-{(1-(3-{(N-(2-furylmethyl)carbamoyl)methyl}phenyl)-5-oxopyrrolidin-3-yl)carbonylamino}-3-(3-pyridyl)propanoic acid;

3-((1-{3-((N-butylcarbamoyl)methyl)phenyl}-5-oxopyrrolidin-3-yl)carbonylamino)-3-(3-pyridyl)propanoic acid;

3-{(5-oxo-1-(3-{(N-benzylcarbamoyl)methyl}phenyl)pyrrolidin-3-yl)carbonylamino}-3-(3-pyridyl)propanoic acid;

3-{(5-oxo-1-(3-{(N-(2-thienylmethyl)carbamoyl)methyl}phenyl)pyrrolidin-3-yl)carbonylamino}-3-(3-pyridyl)propanoic acid;

3-({1-(3-(amidinoamino)phenyl)-5-oxopyrrolidin-3-yl}carbonylamino)-3-(3,5-dichlorophenyl)propanoic acid;

3-(3,5-dichlorophenyl)-3-({1-(3-(2-imidazolin-2-ylamino)phenyl)-5-oxopyrrolidin-3-yl}carbonylamino)propanoic acid;

3-(3,5-dichlorophenyl)-3-({5-oxo-1-(3-(3,4,5,6-tetrahydropyrimidin-2-ylamino)phenyl)pyrrolidin-3-yl}carbonylamino)propanoic acid;

3-({5-oxo-1-(3-(3,4,5,6-tetrahydropyrimidin-2-ylamino)phenyl)pyrrolidin-3-yl}carbonylamino)-3-(3-pyridyl)propanoic acid;

3-(3,5-dichloro-2-hydroxyphenyl)-3-({1-(3-(2-imidazolin-2-ylamino)phenyl)-5-oxopyrrolidin-3-yl}carbonylamino)propanoic acid;

3-(3,5-dichloro-2-hydroxyphenyl)-3-({5-oxo-1-(3-(3,4,5,6-tetrahydropyrimidin-2-ylamino)phenyl)pyrrolidin-3-yl}carbonylamino)propanoic acid;

3-({1-(3-({N-(2-(dimethylamino)ethyl)carbamoyl}amino)phenyl)-5-oxopyrrolidin-3-yl}carbonylamino)-3-(3-pyridyl)propanoic acid;

(3R)-3-{((3R)-5-oxo-1-(-{(benzylamino)carbonylamino}phenyl)pyrrolidin-3-yl)carbonylamino}-3-(3-pyridyl)propanoic acid;

L-2-(phenylsulfonylamino)-3-{(5-oxo-1-(3-{(benzylamino)carbonylamino}phenyl)pyrrolidin-3-yl)carbonylamino}propionic acid;

3-{(1-(2-fluoro-5-{((2-thienylmethyl)amino)carbonylamino}phenyl)-5-oxopyrrolidin-3-yl)carbonylamino}-3-(3-pyridyl)propanoic acid;

3-{(1-(3-{(N-ethyl-N-(4-pyridylmethyl)amino)carbonylamino}phenyl)-5-oxopyrrolidin-3-yl)carbonylamino}-3-(3-pyridyl)propanoic acid;

3-{(5-oxo-1-(3-{(benzylamino)carbonylamino}phenyl)pyrrolidin-3-yl)carbonylamino}-2-((phenylmethoxy)carbonylamino)propanoic acid;

3-{(5-oxo-1-{3-((2-pyridylamino)methyl)phenyl}pyrrolidin-3-yl)carbonylamino}-3-(3-pyridyl)propanoic acid;

3-((5-oxo-1-{3-((phenylmethoxy)carbonylamino)phenyl}pyrrolidin-3-yl)carbonylamino)-3-(3-pyridyl)propanoic acid;

3-((5-oxo-1-{3-((2-pyridylamino)methyl)phenyl}pyrrolidin-3-yl)carbonylamino)-2-(phenylsulfonylamino)propanoic acid;

3-(1,3-benzodioxol-5-yl)-3-{(5-oxo-1-(2-hydroxy-5-{(benzylamino)carbonylamino}phenyl)pyrrolidin-3-yl)carbonylamino}propanic acid;

3-{(5-oxo-1-(3-{(benzylamino)carbonylamino}phenyl)pyrrolidin-3-yl)carbonylamino}-3-(3-pyridyl)propanic acid;

3-({1-(3-({((4-chlorophenyl)methyl)amino}carbonylamino)phenyl)-5-oxopyrrolidin-3-yl}carbonylamino)-3-(3-pyridyl)propanic acid;

3-(4-ethoxyphenyl)-3-{(1-(2-hydroxy-5-{(benzylamino)carbonylamino}phenyl)-5-oxopyrrolidin-3-yl)carbonylamino}propanic acid;

3-(4-ethoxyphenyl)-3-((5-oxo-1-{3-((2-pyridylamino)methyl)phenyl}pyrrolidin-3-yl)carbonylamino}propanic acid;

3-(4-ethoxyphenyl)-3-{(1-(2-fluoro-5-{((2-thienylmethyl)amino)carbonylamino}phenyl)-5-oxopyrrolidin-3-yl)carbonylamino}propanoic acid;

3-(2,4-dimethoxyphenyl)-3-{(1-(2-fluoro-5-{((2-thienylmethyl)amino)carbonylamino}phenyl)-5-oxopyrrolidin-3-yl)carbonylamino}propanoic acid;

3-(3-fluoro-4-methoxyphenyl)-3-{(1-(2-fluoro-5-{((2-thienylmethyl)amino)carbonylamino}phenyl)-5-oxopyrrolidin-3-yl)carbonylamino}propanoic acid;

3-(4-propoxyphenyl)-3-{(1-(2-fluoro-5-{((2-thienylmethyl)amino)carbonylamino}phenyl)-5-oxopyrrolidin-3-yl)carbonylamino}propanoic acid;

3-(4-methoxyphenyl)-3-{(1-(2-fluoro-5-{((2-thienylmethyl)amino)carbonylamino}phenyl)-5-oxopyrrolidin-3-yl)carbonylamino}propanoic acid;

3-{(1-(2-fluoro-5-((2-thienylmethyl)amino)carbonylamino}phenyl)-5-oxopyrrolidin-3-yl)carbonylamino}-3-(3-quinolyl)propanoic acid;

3-(1,3-benzodioxol-5-yl)-3-{(1-(2-fluoro-5-{((2-thienylmethyl)amino)carbonylamino}phenyl)-5-oxopyrrolidin-3-yl)carbonylamino}propanoic acid;

3-(4-ethylphenyl)-3-{(1-(2-fluoro-5-{((2-thienylmethyl)amino)carbonylamino}phenyl)-5-oxopyrrolidin-3-yl)carbonylamino}propanoic acid;

3-{(5-oxo-1-(3-{(2-thienylmethylamino)carbonylamino}phenyl)pyrrolidin-3-yl)carbonylamino}-3-(3,4-dimethoxyphenyl)propanic acid;

3-{(5-oxo-1-(3-{(benzylamino)carbonylamino}phenyl)pyrrolidin-3-yl)carbonylamino}-3-(3-thienyl)propanic acid;

3-{(5-oxo-1-(3-{(benzylamino)carbonylamino}phenyl)pyrrolidin-3-yl)carbonylamino}-3-(4-(trifluoromethoxy)phenyl)propanic acid;

3-{(5-oxo-1-(3-{(benzylamino)carbonylamino}phenyl)pyrrolidin-3-yl)carbonylamino}-3-(cyclohexyl)propanic acid;

3-{(5-oxo-1-(3-{(3,4-dichlorophenylmethylamino)carbonylamino}phenyl)pyrrolidin-3-yl)carbonylamino}-3-(3-pyridyl)propanic acid;

3-{(5-oxo-1-(3-{(2,4-difluorophenylmethylamino)carbonylamino}phenyl)pyrrolidin-3-yl)carbonylamino}-3-(3-pyridyl)propanic acid;

3-{(5-oxo-1-(3-{(4-(trifluoromethyl)phenylmethylamino)carbonylamino}phenyl)pyrrolidin-3-yl)carbonylamino}-3-(phenyl)propanic acid;

3-{(5-oxo-1-(3-{(benzylamino)carbonylamino}phenyl)pyrrolidin-3-yl)carbonylamino}-3-(4-ethylphenyl)propanic acid;

3-{(5-oxo-1-(3-{(benzylamino)carbonylamino}phenyl)pyrrolidin-3-yl)carbonylamino}-3-(cyclopropyl)propanic acid;

3-{(5-oxo-1-(3-{(3,3-dimethylbutylamino)carbonylamino}phenyl)pyrrolidin-3-yl)carbonylamino}-3-(3-pyridyl)propanic acid;

3-{(5-oxo-1-(3-{((perfluoropropyl)methyl)amino)carbonylamino}phenyl)pyrrolidin-3-yl)carbonylamino}-3-(3-pyridyl)propanic acid;

3-{(5-oxo-1-(3-{(3-chlorophenylmethylamino)carbonylamino}phenyl)pyrrolidin-3-yl)carbonylamino}-3-(3-pyridyl)propanic acid;

3-{(5-oxo-1-(3-{(cyclohexylmethylamino)carbonylamino}phenyl)pyrrolidin-3-yl)carbonylamino}-3-(3-pyridyl)propanic acid;

3-{(5-oxo-1-(3-{(2-methoxyphenylmethylamino)carbonylamino}phenyl)pyrrolidin-3-yl)carbonylamino}-3-(3-pyridyl)propanic acid;

3-{(5-oxo-1-(3-{(3-(trifluoromethoxy)phenylmethylamino)carbonylamino}phenyl)pyrrolidin-3-yl)carbonylamino}-3-(3-pyridyl)propanic acid;

3-{(5-oxo-1-(3-{(4-chlorophenylmethylamino)carbonylamino}phenyl)pyrrolidin-3-yl)carbonylamino}-3-(3-pyridyl)propanic acid;

3-{(5-oxo-1-(3-{(2-fluorophenylmethylamino)carbonylamino}phenyl)pyrrolidin-3-yl)carbonylamino}-3-(3-pyridyl)propanic acid;

3-{(5-oxo-1-(3-{(benzylamino)carbonylamino}phenyl)pyrrolidin-3-yl)carbonylamino}-3-(phenyl)propanic acid;

3-{(5-oxo-1-(3-{(3-(trifluoromethyl)phenylmethylamino)carbonylamino}phenyl)pyrrolidin-3-yl)carbonylamino}-3-(phenyl)propanic acid;

3-{(5-oxo-1-(3-{(benzylamino)carbonylamino}phenyl)pyrrolidin-3-yl)carbonylamino}-3-(3,5-dimethoxyphenyl)propanic acid;

3-{(5-oxo-1-(3-{(2-thienylmethylamino)carbonylamino}phenyl)pyrrolidin-3-yl)carbonylamino}-3-(3,5-difluorophenyl)propanic acid;

3-{(5-oxo-1-(3-{(2-furylmethylamino)carbonylamino}phenyl)pyrrolidin-3-yl)carbonylamino}-3-(3-pyridyl)propanic acid;

3-{(5-oxo-1-(3-{(3-fluorophenylmethylamino)carbonylamino}phenyl)pyrrolidin-3-yl)carbonylamino}-3-(3-pyridyl)propanic acid;

3-{(5-oxo-1-(3-{(2-biphenylmethylamino)
carbonylamino}phenyl)pyrrolidin-3-yl)carbonylamino}-
3-(3-pyridyl)propanic acid;

3-{(5-oxo-1-(3-{(2-chlorophenylmethylamino)
carbonylamino}phenyl)pyrrolidin-3-yl)carbonylamino}-
3-(3-pyridyl)propanic acid;

3-{(5-oxo-1-(3-{(2,4-dichlorophenylmethylamino)
carbonylamino}phenyl)pyrrolidin-3-yl)carbonylamino}-
3-(3-pyridyl)propanic acid;

3-{(5-oxo-1-(3-{(2-methylphenylmethylamino)
carbonylamino}phenyl)pyrrolidin-3-yl)carbonylamino}-
3-(3-pyridyl)propanic acid;

3-{(5-oxo-1-(3-{(5-methylfur-2-ylmethylamino)
carbonylamino}phenyl)pyrrolidin-3-yl)carbonylamino}-
3-(3-pyridyl)propanic acid;

3-{(5-oxo-1-(3-{(3-methylphenylmethylamino)
carbonylamino}phenyl)pyrrolidin-3-yl)carbonylamino}-
3-(3-pyridyl)propanic acid;

3-{(5-oxo-1-(3-{(3-methylbutylamino)
carbonylamino}phenyl)pyrrolidin-3-yl)carbonylamino}-
3-(3-pyridyl)propanic acid;

3-{(5-oxo-1-(3-{(2,2,2-trifluoroethylamino)
carbonylamino}phenyl)pyrrolidin-3-yl)carbonylamino}-
3-(3-pyridyl)propanic acid;

3-{(5-oxo-1-(3-{(2-(trifluoromethyl)phenylmethylamino)
carbonylamino}phenyl)pyrrolidin-3-yl)carbonylamino}-
3-(3-pyridyl)propanic acid;

3-{(5-oxo-1-(3-{(((perfluoroethyl)methyl)amino)
carbonylamino}phenyl)pyrrolidin-3-yl)carbonylamino}-
3-(3-pyridyl)propanic acid;

3-{(5-oxo-1-(3-{(2-thienylmethylamino)
carbonylamino}phenyl)pyrrolidin-3-yl)carbonylamino}-
3-(3-fluorophenyl)propanic acid;

3-{(5-oxo-1-(3-{(2-thienylmethylamino)
carbonylamino}phenyl)pyrrolidin-3-yl)carbonylamino}-
3-(3-fluoro-4-methoxyphenyl)propanic acid;

3-{(5-oxo-1-(3-{(2-thienylmethylamino)
carbonylamino}phenyl)pyrrolidin-3-yl)carbonylamino}-
3-(3-ethoxy-4-methoxyphenyl)propanic acid;

3-{(5-oxo-1-(3-{(2-thienylmethylamino)
carbonylamino}phenyl)pyrrolidin-3-yl)carbonylamino}-
3-(4-methoxyphenyl)propanic acid;

3-{(5-oxo-1-(3-{(2-thienylmethylamino)
carbonylamino}phenyl)pyrrolidin-3-yl)carbonylamino}-
3-(3-pyridyl)propanic acid;

3-{(5-oxo-1-(3-{(2-thienylmethylamino)
carbonylamino}phenyl)pyrrolidin-3-yl)carbonylamino}-
3-(3-quinolinyl)propanic acid;

3-{(5-oxo-1-(3-{(benzylamino)carbonylamino}phenyl)
pyrrolidin-3-yl)carbonylamino}-3-(3-quinolinyl)
propanic acid;

3-{(5-oxo-1-(3-{(cyclopropylmethylamino)
carbonylamino}phenyl)pyrrolidin-3-yl)carbonylamino}-
3-(3-pyridyl)propanic acid;

3-{(5-oxo-1-(3-{(3-methoxyphenylmethylamino)
carbonylamino}phenyl)pyrrolidin-3-yl)carbonylamino}-
3-(3-pyridyl)propanic acid;

3-({1-(3-(amidinoamino)phenyl)-5-oxopyrrolino-3-
yl}carbonylamino)-3-(3-pyridyl)propanoic acid trifluoro-
acetate;

3-(3,5-difluorophenyl)-3-({5-oxo-1-(3-(3,4,5,6-
tetrahydropyrimidin-2-ylamino)phenyl)pyrrolidin-3-
yl}carbonylamino)propanoic acid trifluoroacetate;

3-(3,5-dichlorophenyl)-3-((1-{3-((5-hydroxy(3,4,5,6-
tetrahydropyrimidin-2-yl))amino)phenyl}-5-
oxopyrrolidin-3-yl)carbonylamino)propanoic acid trifluo-
roacetate;

3-(2H-benzo[3,4-d]1,3-dioxolen-5-yl)-3-({5-oxo-1-(3-(3,4,
5,6-tetrahydropyrimidin-2-ylamino)phenyl)pyrrolidin-3-
yl}carbonylamino)propanoic acid;

3-(2H,3 H-benzo[3,4-e]1,4-dioxin-6-yl)-3-({5-oxo-1-(3-(3,
4,5,6-tetrahydropyrimidin-2-ylamino)phenyl)pyrrolidin-
3-yl}carbonylamino)propanoic acid;

3-({5-oxo-1-[3-(3,4,5,6-tetrahydropyrimidin-2-ylamino)
phenyl]pyrrolidin-3-yl}carbonylamino)-3-(3-quinolyl)
propanoic acid;

3-(2,2-difluorobenzo[3,4-d]1,3-dioxolen-5-yl)-3-({5-oxo-1-
[3-(3,4,5,6-tetrahydropyrimidin-2-ylamino)phenyl]
pyrrolidin-3-yl}carbonylamino)propanoic acid.

Compounds of the invention may be shown to inhibit vitronectin $\alpha_v\beta_3$ binding in vitronectin $\alpha_v\beta_3$ binding assays and to inhibit osteoclasts mediated bone resorption in bone resorption pit assays as described in Woo et al. (Eur. J. Pharm. 300:131–5, 1996), EP 528587, WO 97/01540, WO 98/18461 and WO 99/30713 (each of which is incorporated herein by reference in its entirety). Compounds of the invention may be shown to inhibit smooth muscle cell migration in human aortic smooth muscle cell migration assay described in WO 97/01540 and Liaw et al., J. Clin. Invest. 95:713–724, 1995 (each of which is incorporated herein by reference in its entirety).

Compounds of the invention may be shown to inhibit vitronectin $\alpha_v\beta_5$ and/or $\alpha_v\beta_6$ binding in vitronectin $\alpha_v\beta_5$ and $\alpha_v\beta_6$ binding assays as described in WO 99/30709 and WO 99/30713 (each of which are incorporated herein by reference in its entirety). Compounds of the invention may be shown to inhibit $\alpha_5\beta_1$ integrin binding in $\alpha_5\beta_1$ integrin binding assays as described in WO 99/58139 (incorporated herein by reference in its entirety).

Compounds of the invention may be shown to have anti-bone resorption properties in a rat animal models described in WO 97/01540 and Wronski et al., Cells and Mat. 1991:69–74 (each of which is incorporated herein by reference in its entirety). Compounds of the invention may be shown to have anti-angiogenic properties in an animal model described in Passaniti et al., Lab. Invest. 67:519–528, 1992 (incorporated herein by reference in its entirety). Compounds of the invention may be shown to inhibit restenosis in a pig restenosis model described in Schwartz et al., J. Am. College of Cardiology 19:267–274, 1992 (incorporated herein by reference in its entirety). Compounds of the invention may be shown to inhibit retinopathy in a mouse retinopathy model described in Smith et al., Invest. Ophthal. & Vis. Sci. 35:101–111, 1994 (incorporated herein by reference in its entirety).

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula $$U—V—A\text{-}(Alk)_j\text{-}(C(O)—NH)_h\text{-}(Alk)_g\text{-}B$$

or a pharmaceutically acceptable salt thereof, wherein g, h and j are each independently 0 or 1; provided when h is 0, then g is 0;

each Alk is independently a alkyl radical;

U represents guanidino, —(G-alkyl)$_k$—NH—R$_1$, —(G-alkyl)$_k$—NH—C(Q)—R$_1$, —(G-alkyl)$_k$—C(Q)—N(R)—R$_1$, —(G-alkyl)$_k$—NH—C(Q)—N(R)—R$_1$, —(G-alkyl)$_k$—NH—C(Q)—O—R$_1$ or —(G-alkyl)$_k$—O—C(Q)—N(R)—R$_1$ radical; or U represents a hydroxyalkyl-G-radical which is optionally substituted by a cycloalkyl, aryl, heteroaryl or heterocyclyl, wherein the cycloalkyl, aryl, heteroaryl and heterocyclyl radicals are optionally substituted by 1–3 radicals of R$_2$;

wherein k is 0 or 1;

G represents a bond, O, S or NH;

Q represents O, S, NH, N—CN or N-alkyl;

R is a radical of hydrogen or alkyl;

R$_1$ is a radical of alkyl, haloalkyl, R$_{21}$R$_{22}$N-alkyl, R$_{21}$O-alkyl, R$_{21}$S-alkyl, cycloalkyl, cycloalkyl-alkyl, aryl, aryl-alkyl, heteroaryl, heteroaryl-alkyl, heterocyclyl or heterocyclyl-alkyl, wherein the cycloalkyl, aryl, heteroaryl and heterocyclyl radicals are optionally substituted by 1–3 radicals of R$_2$;

wherein R$_{21}$ and R$_{22}$ are each independently a radical of hydrogen, alkyl, haloalkyl, cycloalkyl, cycloalkyl-alkyl, aryl, aryl-alkyl, heteroaryl, heteroaryl-alkyl, heterocyclyl or heterocyclyl-alkyl, wherein the cycloalkyl, aryl, heteroaryl and heterocyclyl radicals are optionally substituted by 1–3 radicals of R$_2$;

each R$_2$ is independently a halo, alkyl, alkoxy, alkylthio, haloalkyl, haloalkoxy, hydroxy, carboxy, cyano, azido, amidino, guanidino, nitro, amino, alkylamino or dialkylamino radical or two adjacent R$_2$ radicals on an aryl or heteroaryl radical represent a methylenedioxy, ethylenedioxy or propylenedioxy radical;

V represents a radical of formula

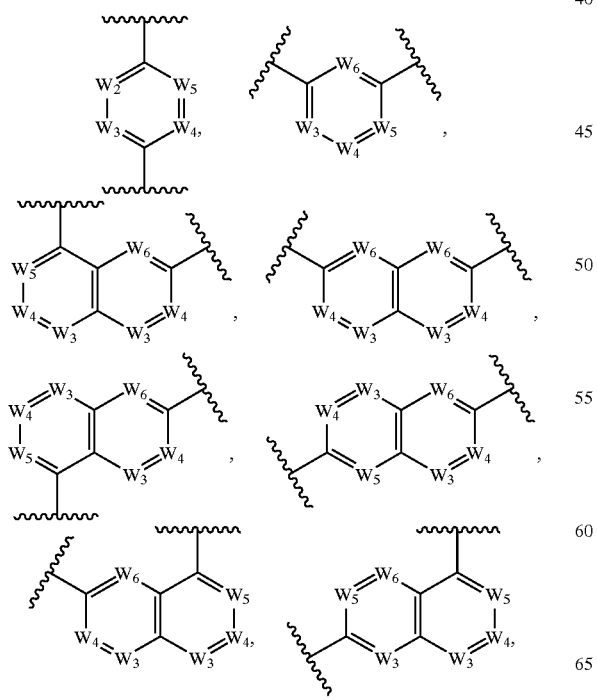

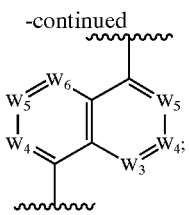

wherein each W$_2$, W$_3$, W$_4$ and W$_5$ C—R$_4$; provided the total number of cycloalkyl, aryl, heteroaryl, heterocyclyl, carboxy, —C(O)—O—R$_{19}$, —C(O)—R$_{19}$, —C(O)—NH—R$_{19}$, —C(O)—N(R$_{19}$)$_2$ and —R$_{19}$ radicals in W$_2$, W$_3$, W$_4$ and W$_5$ is 0–2;

each W$_6$ is C—H; and each R$_4$ is independently a hydrogen, halo, alkyl, alkoxy, alkylthio, haloalkyl, haloalkoxy, hydroxy, cyano, carboxy, —C(O)—O—R$_{19}$, —C(O)—R$_{19}$, —C(O)—NH—R$_{19}$, —C(O)—N(R$_{19}$)$_2$, cycloalkyl, cycloalkyl-alkyl, aryl, aryl-alkyl, heteroaryl, heteroaryl-alkyl, heterocyclyl or heterocyclyl-alkyl radical, wherein the cycloalkyl, aryl, heteroaryl and heterocyclyl radicals are optionally substituted by 1–3 radicals of R$_2$; or two adjacent R$_4$ radicals taken together with the carbon atoms to which they are attached represent a fused-phenyl or fused-heteroaryl of 5–6 ring members, wherein the phenyl and heteroaryl radicals are optionally substituted by 1–3 radicals of R$_2$;

R$_5$, R$_6$ and R$_7$ are each independently a hydrogen, halo, alkyl, alkoxy, alkylthio, haloalkyl, haloalkoxy, hydroxy or cyano radical; or R$_5$ and R$_6$ or R$_6$ and R$_7$ taken together with the carbon atoms to which they are attached represent a fused-phenyl or fused-heteroaryl of 6 ring members, wherein the phenyl and heteroaryl radicals are optionally substituted by 1–3 radicals of R$_2$; or R$_3$ and R$_6$ taken together with the carbon atoms to which they are attached represent a fused-heteroaryl of 6 ring members optionally substituted by 1–3 radicals of R$_2$;

A represents a radical of formula

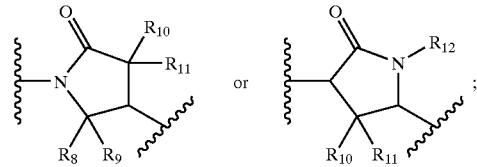

R$_8$, R$_9$, R$_{10}$, R$_{11}$ and R$_{12}$ are each independently a hydrogen or alkyl radical; or —CR$_8$R$_9$— represents a —C(O)—;

B represents a radical of formula

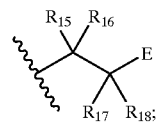

wherein (a) R$_{15}$ is a hydrogen or alkyl radical; and R$_{17}$ is (1) an aryl, heteroaryl, —NH—C(O)—R$_{19}$, —C(O)—NH—R$_{19}$, —NH—C(O)—NH—R$_{19}$, —O—C(O)—NH—R$_{19}$, —NH—C(O)—O—R$_{19}$, —S(O)$_2$—R$_{19}$, —NH—S(O)$_2$—R$_{19}$, —S(O)$_2$—NH—R$_{19}$ or —NH—S(O)$_2$—NH—R$_{19}$ radical, or (2) an alkyl radical substituted by a radical of aryl, heteroaryl, —NH—C(O)—$R_{19}$, —C(O)—NH—$R_{19}$, —NH—C(O)—NH—$R_{19}$, —O—C(O)—NH—$R_{19}$, —NH—C(O)—O—$R_{19}$, —S(O)$_2$—$R_{19}$—NH—S(O)$_2$—$R_{19}$, —S(O)$_2$—NH—$R_{19}$ or —NH—S(O)$_2$—NH—$R_{19}$; wherein the aryl and heteroaryl radicals are optionally substituted by 1–3 radicals of $R_2$; or (b) $R_{17}$ is a hydrogen or alkyl radical; and $R_{15}$ is (1) an aryl, heteroaryl, cycloalkyl, heterocyclyl, —NH—C(O)—$R_{19}$, —C(O)—NH—$R_{19}$, —NH—C(O)—NH—$R_{19}$, —O—C(O)—NH—$R_{19}$, —NH—C(O)—O—$R_{19}$, —S(O)$_2$—$R_{19}$, —NH—S(O)$_2$—$R_{19}$, —S(O)$_2$—NH—$R_{19}$ or —NH—S(O)$_2$—NH—$R_{19}$ radical, or (2) an alkyl radical substituted by a radical of aryl, heteroaryl, cycloalkyl, heterocyclyl, —NH—C(O)—$R_{19}$, —C(O)—NH—$R_{19}$, —NH—C(O)—NH—$R_{19}$, —O—C(O)—NH—$R_{19}$, —NH—C(O)—O—$R_{19}$, —S(O)$_2$—$R_{19}$, —NH—S(O)$_2$—$R_{19}$, —S(O)$_2$—NH—$R_{19}$ or —NH—S(O)$_2$—NH—$R_{19}$ radical; wherein the cycloalkyl, aryl, heteroaryl and heterocyclyl radicals are optionally substituted by 1–3 radicals of $R_2$;

provided that when a nitrogen atom is attached to the carbon atom to which $R_{15}$ is attached, then $R_{15}$ is (1) an aryl, heteroaryl, cycloalkyl, heterocyclyl or —C(O)—NH—$R_{19}$ radical, or (2) an alkyl radical substituted by a radical of aryl, heteroaryl, cycloalkyl, heterocyclyl, —NH—C(O)—$R_{19}$, —C(O)—NH—$R_{19}$, —NH—C(O)—NH—$R_{19}$, —O—C(O)—NH—$R_{19}$, —NH—C(O)—O—$R_{19}$, —S(O)$_2$—$R_{19}$, —NH—S(O)$_2$—$R_{19}$, —S(O)$_2$—NH—$R_{19}$ or —NH—S(O)$_2$—NH—$R_{19}$;

wherein $R_{19}$ is a alkyl, cycloalkyl, cycloalkyl-alkyl, aryl, aryl-alkyl, heteroaryl, heteroaryl-alkyl, heterocyclyl or heterocyclyl-alkyl, wherein the cycloalkyl, aryl, heteroaryl and heterocyclyl radicals are optionally substituted by 1–3 radicals of $R_2$;

$R_{16}$ and $R_{18}$ are each independently a hydrogen or alkyl radical; and

E is a radical of carboxy, amido, tetrazolyl, —C(O)—O—$R_{20}$, —C(O)—NH—$R_{20}$, —C(O)—NH—S(O)—$R_{20}$, —C(O)—NH—S(O)$_2$—$R_{20}$ or —C(O)—NH—C(O)—$R_{20}$;

wherein $R_{20}$ is an alkyl, cycloalkyl, aryl, heteroaryl or heterocyclyl radical or an alkyl radical substituted by 1–3 radicals of halo, hydroxy, carboxy, amino, cycloalkyl, aryl, heteroaryl or heterocyclyl, wherein the cycloalkyl, aryl, heteroaryl and heterocyclyl radicals are optionally substituted by 1–3 radicals of $R_2$; and provided that when U represents guanidino, —C(Q)—NH—$R_1$ or —NH—C(Q)—NH—$R_1$ radical, wherein Q represents NH, N—CN or N-alkyl, then at least one of g, h or j is 1.

2. The compound of claim 1 or a pharmaceutically acceptable salt thereof, wherein each Alk is independently a $C_1$–$C_{12}$ alkyl radical;

U represents guanidino, —(G—($C_1$–$C_8$ alkyl))$_k$—NH—$R_1$, —(G—($C_1$–$C_8$ alkyl))$_k$—NH—C(Q)—$R_1$, —(G—($C_1$–$C_8$ alkyl))$_k$—C(Q)—N(R)—$R_1$, —(G—($C_1$–$C_8$ alkyl))$_k$—NH—C(Q)—N(R)—$R_1$, —(G—($C_1$–$C_8$ alkyl))$_k$—NH—C(Q)—O—$R_1$ or —(G—($C_1$–$C_8$ alkyl))$_k$—O—C(Q)—N(R)—$R_1$ radical; or U represents a hydroxy($C_1$–$C_{12}$ alkyl)-G— radical which is optionally substituted by a $C_3$–$C_8$ cycloalkyl, aryl, heteroaryl of 5–10 ring members or heterocyclyl of 5–8 ring members, wherein the cycloalkyl, aryl, heteroaryl and heterocyclyl radicals are optionally substituted by 1–3 radicals of $R_2$;

Q represents O, S, NH, N—CN or N—($C_1$–$C_8$ alkyl);

R is a radical of hydrogen or $C_1$–$C_8$ alkyl;

$R_1$ is a radical of $C_1$–$C_8$ alkyl, halo($C_1$–$C_8$ alkyl) of 1–7 halo radicals, $R_{21}R_{22}N$—($C_1$–$C_8$ alkyl), $R_{21}O$—($C_1$–$C_8$ alkyl), $R_{21}S$—($C_1$–$C_8$ alkyl), $C_3$–$C_8$ cycloalkyl, $C_3$–$C_8$ cycloalkyl($C_1$–$C_8$ alkyl), aryl, aryl($C_1$–$C_8$ alkyl), heteroaryl of 5–10 ring members, heteroaryl($C_1$–$C_8$ alkyl) of 5–10 ring members, heterocyclyl of 5–8 ring members or heterocyclyl($C_1$–$C_8$ alkyl) of 5–8 ring members, wherein the cycloalkyl, aryl, heteroaryl and heterocyclyl radicals are optionally substituted by 1–3 radicals of $R_2$;

wherein $R_{21}$ and $R_{22}$ are each independently a radical of hydrogen, $C_1$–$C_8$ alkyl, halo($C_1$–$C_8$ alkyl) of 1–7 halo radicals, $C_3$–$C_8$ cycloalkyl, $C_3$–$C_8$ cycloalkyl($C_1$–$C_8$ alkyl), aryl, aryl($C_1$–$C_8$ alkyl), heteroaryl of 5–10 ring members, heteroaryl($C_1$–$C_8$ alkyl) of 5–10 ring members, heterocyclyl of 5–8 ring members or heterocyclyl($C_1$–$C_8$ alkyl) of 5–8 ring members, wherein the cycloalkyl, aryl, heteroaryl and heterocyclyl radicals are optionally substituted by 1–3 radicals of $R_2$;

each $R_2$ is independently a halo, $C_1$–$C_6$ alkyl, $C_1$–$C_6$ alkoxy, $C_1$–$C_6$ alkylthio, halo($C_1$–$C_4$ alkyl) of 1–5 halo radicals, halo($C_1$–$C_4$ alkoxy) of 1–5 halo radicals, hydroxy, carboxy, cyano, azido, amidino, guanidino, nitro, amino, $C_1$–$C_8$ alkylamino or di($C_1$–$C_8$ alkyl) amino radical or two adjacent $R_2$ radicals on an aryl or heteroaryl radical represent a methylenedioxy, ethylenedioxy or propylenedioxy radical;

each $R_3$ is independently a hydrogen or $C_1$–$C_6$ alkyl radical;

each $R_4$ is independently a hydrogen, halo, $C_1$–$C_6$ alkyl, $C_1$–$C_6$ alkoxy, $C_1$–$C_6$ alkylthio, halo($C_1$–$C_4$ alkyl) of 1–5 halo radicals, halo($C_1$–$C_4$ alkoxy) of 1–5 halo radicals, hydroxy, cyano, carboxy, —C(O)—O—$R_{19}$, —C(O)—$R_{19}$, —C(O)—NH—$R_{19}$, —C(O)—N($R_{19}$)$_2$, $C_3$–$C_6$ cycloalkyl, $C_3$–$C_6$ cycloalkyl($C_1$–$C_4$ alkyl), aryl, aryl($C_1$–$C_4$ alkyl), heteroaryl of 5–10 ring members, heteroaryl($C_1$–$C_4$ alkyl) of 5–10 ring members, heterocyclyl of 5–8 ring members or heterocyclyl($C_1$–$C_4$ alkyl) of 5–8 ring members radical, wherein the cycloalkyl, aryl, heteroaryl and heterocyclyl radicals are optionally substituted by 1–3 radicals of $R_2$; or two adjacent $R_4$ radicals taken together with the carbon atoms to which they are attached represent a fused-phenyl or fused-heteroaryl of 5–6 ring members, wherein the phenyl and heteroaryl radicals are optionally substituted by 1–3 radicals of $R_2$;

$R_5$, $R_6$ and $R_7$ are each independently a hydrogen, halo, $C_1$–$C_6$ alkyl, $C_1$–$C_6$ alkoxy, $C_1$–$C_6$ alkylthio, halo ($C_1$–$C_4$ alkyl) of 1–5 halo radicals, halo($C_1$–$C_4$ alkoxy) of 1–5 halo radicals, hydroxy or cyano radical; or $R_5$ and $R_6$ or $R_6$ and $R_7$ taken together with the carbon atoms to which they are attached represent a fused-phenyl or fused-heteroaryl of 6 ring members, wherein the phenyl and heteroaryl radicals are optionally substituted by 1–3 radicals of $R_2$; or $R_3$ and $R_6$ taken together with the carbon atoms to which they are attached represent a fused-heteroaryl of 6 ring members, wherein the phenyl and heteroaryl radicals are optionally substituted by 1–3 radicals of $R_2$; or $R_3$ and $R_6$ taken together with the carbon atoms to which they are attached represent a fused-heteroaryl of 6 ring members optionally substituted by 1–3 radicals of $R_2$;

$X_2$ is C—H, C—($C_1$–$C_4$ alkyl), a $C_3$–$C_8$ spirocycloalkyl or spiroheterocyclyl of 5–8 ring members radical;

wherein the spirocycloalkyl and spiroheterocyclyl radicals are optionally substituted by an oxo or thiooxo radical and 1–2 radicals of $C_1$–$C_6$ alkyl, halo($C_1$–$C_4$ alkyl) of 1–5 halo radicals, hydroxy, $C_1$–$C_6$ alkoxy or halo($C_1$–$C_4$ alkoxy) of 1–5 halo radicals;

$R_8$, $R_9$, $R_{10}$, $R_{11}$ and $R_{12}$ are each independently a hydrogen or $C_1$–$C_6$ alkyl radical; or —$CR_8R_9$— represents a —C(O)—;

B represents a radical of formula

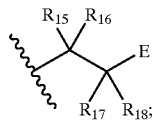

wherein (a) $R_{15}$ is a hydrogen or $C_1$–$C_6$ alkyl radical; and $R_{17}$ is (1) an aryl, heteroaryl of 5–10 ring members, —NH—C(O)—$R_{19}$, —C(O)—NH—$R_{19}$, —NH—C(O)—NH—$R_{19}$, —O—C(O)—NH—$R_{19}$, —NH—C(O)—O—$R_{19}$, —S(O)$_2$—$R_{19}$, —NH—S(O)$_2$—$R_{19}$, —S(O)$_2$—NH—$R_{19}$ or —NH—S(O)$_2$—NH—$R_{19}$ radical, or (2) an $C_1$–$C_6$ alkyl radical substituted by a radical of aryl, heteroaryl of 5–10 ring members, —NH—C(O)—$R_{19}$, —C(O)—NH—$R_{19}$, —NH—C(O)—NH—$R_{19}$, —O—C(O)—NH—$R_{19}$, —NH—C(O)—O—$R_{19}$, —S(O)$_2$—$R_{19}$, —NH—S(O)$_2$—$R_{19}$, —S(O)$_2$—NH—$R_{19}$ or —NH—S(O)$_2$—NH—$R_{19}$; wherein the aryl and heteroaryl radicals are optionally substituted by 1–3 radicals of $R_2$; or (b) $R_{17}$ is a hydrogen or $C_1$–$C_6$ alkyl radical; and $R_{15}$ is (1) an aryl, heteroaryl of 5–10 ring members, $C_3$–$C_8$ cycloalkyl, heterocyclyl of 5–8 ring members, —NH—C(O)—$R_{19}$, —C(O)—NH—$R_{19}$, —NH—C(O)—NH—$R_{19}$, —O—C(O)—NH—$R_{19}$, —NH—C(O)—O—$R_{19}$, —S(O)$_2$—$R_{19}$, —NH—S(O)$_2$—$R_{19}$, —S(O)$_2$—NH—$R_{19}$ or —NH—S(O)$_2$—NH—$R_{19}$ radical, or (2) an $C_1$–$C_4$ alkyl radical substituted by a radical of aryl, heteroaryl of 5–10 ring members, $C_3$–$C_8$ cycloalkyl, heterocyclyl of 5–8 ring members, —NH—C(O)—$R_{19}$, —C(O)—NH—$R_{19}$, —NH—C(O)—NH—$R_{19}$, —O—C(O)—NH—$R_{19}$, —NH—C(O)—O—$R_{19}$, —S(O)$_2$—$R_{19}$, —NH—S(O)$_2$—$R_{19}$, —S(O)$_2$—NH—$R_{19}$ or —NH—S(O)$_2$—NH—$R_{19}$ radical; wherein the cycloalkyl, aryl, heteroaryl and heterocyclyl radicals are optionally substituted by 1–3 radicals of $R_2$;

provided that when a nitrogen atom is attached to the carbon atom to which $R_{15}$ is attached, then $R_{15}$ is (1) an aryl, heteroaryl, cycloalkyl, heterocyclyl or —C(O)—NH—$R_{19}$ radical, or (2) an alkyl radical substituted by a radical of aryl, heteroaryl, cycloalkyl, heterocyclyl, —NH—C(O)—$R_{19}$, —C(O)—NH—$R_{19}$, —NH—C(O)—NH—$R_{19}$, —O—C(O)—NH—$R_{19}$, —NH—C(O)—O—$R_{19}$, —S(O)$_2$—$R_{19}$, —NH—S(O)$_2$—$R_{19}$, —S(O)$_2$—NH—$R_{19}$ or —NH—S(O)$_2$—NH—$R_{19}$;

wherein $R_{19}$ is a $C_1$–$C_6$ alkyl, $C_3$–$C_8$ cycloalkyl, $C_3$–$C_8$ cycloalkyl($C_1$–$C_6$ alkyl), aryl, aryl($C_1$–$C_6$ alkyl), heteroaryl of 5–10 ring members, heteroaryl($C_1$–$C_6$ alkyl) of 5–10 ring members, heterocyclyl of 5–8 ring members or heterocyclyl($C_1$–$C_6$ alkyl) of 5–8 ring members, wherein the cycloalkyl, aryl, heteroaryl and heterocyclyl radicals are optionally substituted by 1–3 radicals of $R_2$;

$R_{16}$ and $R_{18}$ are each independently a hydrogen or $C_1$–$C_6$ alkyl radical; and $R_{20}$ is a $C_1$–$C_6$ alkyl, $C_3$–$C_8$ cycloalkyl, aryl, heteroaryl of 5–10 ring members or heterocyclyl of 5–8 ring members radical or a $C_1$–$C_6$ alkyl radical substituted by 1–3 radicals of halo, hydroxy, carboxy, amino, $C_3$–$C_8$ cycloalkyl, aryl, heteroaryl of 5–10 ring members or heterocyclyl of 5–8 ring members, wherein the cycloalkyl, aryl, heteroaryl and heterocyclyl radicals are optionally substituted by 1–3 radicals of $R_2$.

3. The compound of claim 2 or a pharmaceutically acceptable salt thereof, wherein each Alk is independently a $C_1$–$C_8$ alkyl radical;

V represents a radical of formula

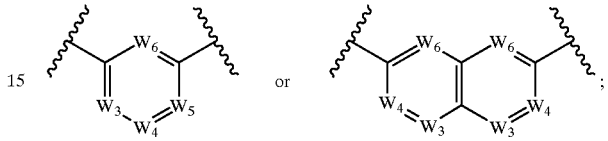

$R_8$, $R_9$, $R_{10}$, $R_{11}$ and $R_{12}$ are each independently a hydrogen or methyl radical; or —$CR_8R_9$— represents a —C(O)—.

4. The compound of claim 3 or a pharmaceutically acceptable salt thereof, wherein each Alk is independently a $C_1$–$C_6$ alkyl radical;

U represents guanidino, —(G—($C_1$–$C_8$ alkyl))$_k$—NH—$R_1$, —(G—($C_1$–$C_8$ alkyl))$_k$—NH—C(Q)—$R_1$, —(G—($C_1$–$C_8$ alkyl))$_k$—C(Q)—N(R)—$R_1$, —(G—($C_1$–$C_8$ alkyl))$_k$—NH—C(Q)—N(R)—$R_1$ or —(G—($C_1$–$C_8$ alkyl))$_k$—NH—C(Q)—O—$R_1$ radical;

G represents a bond, O or NH;

Q represents O, S, NH, N—CN or N—($C_1$–$C_4$ alkyl);

R is a radical of hydrogen or $C_1$–$C_4$ alkyl;

$R_1$ is a radical of $C_1$–$C_6$ alkyl, halo($C_1$–$C_6$ alkyl) of 1–5 halo radicals, $R_{21}R_{22}N$—($C_1$–$C_6$ alkyl), $R_{21}O$—($C_1$–$C_6$ alkyl), $C_3$–$C_8$ cycloalkyl, $C_3$–$C_8$ cycloalkyl($C_1$–$C_6$ alkyl), aryl, aryl($C_1$–$C_6$ alkyl), heteroaryl of 5–10 ring members, heteroaryl($C_1$–$C_6$ alkyl) of 5–10 ring members, heterocyclyl of 5–8 ring members or heterocyclyl($C_1$–$C_6$ alkyl) of 5–8 ring members, wherein the cycloalkyl, aryl, heteroaryl and heterocyclyl radicals are optionally substituted by 1–3 radicals of $R_2$;

$R_{21}$ and $R_{22}$ are each independently a radical of hydrogen, $C_1$–$C_8$ alkyl, aryl, aryl($C_1$–$C_4$ alkyl), heteroaryl of 5–10 ring members or heteroaryl($C_1$–$C_4$ alkyl) of 5–10 ring members, wherein the aryl and heteroaryl radicals are optionally substituted by 1–3 radicals of $R_2$;

each $R_2$ is independently a halo, $C_1$–$C_4$ alkyl, $C_1$–$C_4$ alkoxy, $C_1$–$C_4$ alkylthio, halo($C_1$–$C_2$ alkyl) of 1–5 halo radicals, halo($C_1$–$C_2$ alkoxy) of 1–5 halo radicals, hydroxy, carboxy, cyano, azido, amidino, guanidino, nitro, amino, $C_1$–$C_4$ alkylamino or di($C_1$–$C_4$ alkyl) amino radical or two adjacent $R_2$ radicals on an aryl or heteroaryl radical represent a methylenedioxy, ethylenedioxy or propylenedioxy radical;

each $R_4$ is independently a hydrogen, halo, $C_1$–$C_4$ alkyl, $C_1$–$C_4$ alkoxy, $C_1$–$C_4$ alkylthio, halo($C_1$–$C_2$ alkyl) of 1–5 halo radicals, halo($C_1$–$C_2$ alkoxy) of 1–5 halo radicals, hydroxy, cyano, carboxy, —C(O)—O—$R_{19}$, —C(O)—$R_{19}$, —C(O)—NH—$R_{19}$, —C(O)—N($R_{19}$)$_2$, $C_3$–$C_6$ cycloalkyl, $C_3$–$C_6$ cycloalkyl($C_1$–$C_4$ alkyl), aryl, aryl($C_1$–$C_4$ alkyl), heteroaryl of 5–10 ring members, heteroaryl($C_1$–$C_4$ alkyl) of 5–10 ring members, heterocyclyl of 5–8 ring members or heterocyclyl($C_1$–$C_4$ alkyl) of 5–8 ring members radical, wherein the cycloalkyl, aryl, heteroaryl and heterocyclyl radicals are optionally substituted by 1–3 radicals of $R_2$; and $R_{20}$ is a $C_1$–$C_4$ alkyl, aryl or heteroaryl of 5–10 ring members or a $C_1$–$C_4$ alkyl radical substituted by 1–3 radicals of halo, hydroxy, carboxy, amino, aryl, heteroaryl of 5–10 ring members or heterocyclyl of 5–8 ring members, wherein the aryl, heteroaryl and heterocyclyl radicals are optionally substituted by 1–3 radicals of $R_2$.

5. The compound of claim 4 or a pharmaceutically acceptable salt thereof, wherein U represents guanidino, —(G—($C_1$–$C_8$ alkyl))$_k$—NH—$R_1$, —NH—C(Q)—$R_1$, —(G—($C_1$–$C_8$ alkyl))$_k$—C(Q)—N(R)—$R_1$, —NH—C(Q)—N(R)—$R_1$ or —NH—C(Q)—N(R)—$R_1$ or —N(R)—$R_1$ radical;

Q represents O or NH;

R is a radical of hydrogen or $C_1$–$C_4$ alkyl;

$R_1$ is a radical of $C_1$–$C_6$ alkyl, halo($C_1$–$C_6$ alkyl) of 1–5 halo radicals, $R_{21}R_{22}$N—($C_1$–$C_6$ alkyl), $R_{21}$O—($C_1$–$C_6$ alkyl), $C_3$–$C_8$ cycloalkyl, $C_3$–$C_8$ cycloalkyl ($C_1$–$C_6$ alkyl), aryl, aryl($C_1$–$C_6$ alkyl), heteroaryl of 5–10 ring members, heteroaryl($C_1$–$C_4$ alkyl) of 5–10 ring members, heterocyclyl of 5–8 ring members or heterocyclyl($C_1$–$C_6$ alkyl) of 5–8 ring members, wherein the cycloalkyl, aryl, heteroaryl and heterocyclyl radicals are optionally substituted by 1–3 radicals of $R_2$;

$R_{21}$ and $R_{22}$ are each independently a radical of hydrogen, $C_1$–$C_8$ alkyl, aryl, aryl($C_1$–$C_4$ alkyl), heteroaryl of 5–10 ring members, wherein the aryl and heteroaryl radicals are optionally substituted by 1–3 radicals of $R_2$;

each $R_2$ is independently a halo, $C_1$–$C_2$ alkyl, $C_1$–$C_2$ alkoxy, $C_1$–$C_2$ alkylthio, $CF_3$—, $CF_3O$—, hydroxy, carboxy, cyano, azido, amidino, guanidino, nitro, amino, $C_1$–$C_2$ alkylamino or di($C_1$–$C_2$ alkyl)amino radical or two adjacent $R_2$ radicals on an aryl or heteroaryl radical represent a methylenedioxy, ethylenedioxy or propylenedioxy radical;

each $W_2$, $W_3$, $W_4$ and $W_5$ are independently C—$R_4$;

each $R_4$ is independently a hydrogen, halo, $C_1$–$C_4$ alkyl, $C_1$–$C_4$ alkoxy, $C_1$–$C_4$ alkylthio, halo($C_1$–$C_2$ alkyl) of 1–5 halo radicals, halo($C_1$–$C_2$ alkoxy) of 1–5 halo radicals, hydroxy, cyano radical;

A represents a radical of formula

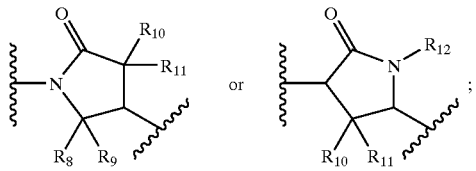

(a) $R_{15}$ is a hydrogen or $C_1$–$C_2$ alkyl radical; and $R_{17}$ is —NH—C(O)—$R_{19}$, —NH—C(O)—NH—$R_{19}$, —NH—C(O)—O—$R_{19}$, —NH—S(O)$_2$—$R_{19}$ or —NH—S(O)$_2$—NH—$R_{19}$ radical; or (b) $R_{17}$ is a hydrogen or $C_1$–$C_2$ alkyl radical; and $R_{15}$ is (1) an aryl, heteroaryl of 5–10 ring members, $C_3$–$C_8$ cycloalkyl or heterocyclyl of 5–8 ring members radical, or (2) an $C_1$–$C_2$ alkyl radical substituted by a radical of aryl, heteroaryl of 5–10 ring members, $C_3$–$C_8$ cycloalkyl or heterocyclyl of 5–8 ring members radical; wherein the cycloalkyl, aryl, heteroaryl and heterocyclyl radicals are optionally substituted by 1–3 radicals of $R_2$;

$R_{19}$ is a $C_1$–$C_4$ alkyl, aryl, aryl($C_1$–$C_4$ alkyl), heteroaryl of 5–10 ring members or heteroaryl($C_1$–$C_4$ alkyl) of 5–10 ring members, wherein the aryl and heteroaryl radicals are optionally substituted by 1–3 radicals of $R_2$;

$R_{16}$ and $R_{18}$ are each independently a hydrogen or $C_1$–$C_4$ alkyl radical;

E is a radical of carboxy, amido, tetrazolyl or —C(O)—O—$R_{20}$; and $R_{20}$ is a $C_1$–$C_4$ alkyl, aryl or heteroaryl of 5–10 ring members or a $C_1$–$C_4$ alkyl radical substituted by 1–3 radicals of halo, hydroxy, carboxy, amino, aryl, heteroaryl of 5–10 ring members or heterocyclyl of 5–8 ring members, wherein the aryl, heteroaryl and heterocyclyl radicals are optionally substituted by 1–3 radicals of $R_2$.

6. The compound of claim 5 or a pharmaceutically acceptable salt thereof, wherein Alk is independently a $C_1$–$C_2$ alkyl radical;

G represents a bond or NH;

$R_{21}$ and $R_{22}$ are each independently a radical of hydrogen, $C_1$–$C_6$ alkyl or aryl, wherein the aryl and heteroaryl radicals are optionally substituted by 1–3 radicals of $R_2$;

each $R_4$ is independently a hydrogen, halo, $C_1$–$C_2$ alkyl, $C_1$–$C_2$ alkoxy, $C_1$–$C_2$ alkylthio, $CF_3$—, $CF_3O$—, hydroxy or cyano radical;

A represents a radical of formula

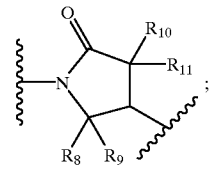

(a) $R_{15}$ is a hydrogen or $C_1$–$C_2$ alkyl radical; and $R_{17}$ is —NH—C(O)—O—$R_{19}$ or —NH—S(O)$_2$—$R_{19}$ radical; or (b) $R_{17}$ is a hydrogen or $C_1$–$C_2$ alkyl radical; and $R_{15}$ is (1) an aryl or heteroaryl of 5–10 ring members, or (2) an $C_1$–$C_2$ alkyl radical substituted by a radical of aryl or heteroaryl of 5–10 ring members; wherein the aryl and heteroaryl radicals are optionally substituted by 1–3 radicals of $R_2$;

$R_{19}$ is a $C_1$–$C_4$ alkyl, aryl, aryl($C_1$–$C_4$ alkyl), wherein the aryl radicals are optionally substituted by 1–3 radicals of $R_2$;

$R_{16}$ and $R_{18}$ are each independently a hydrogen or $C_1$–$C_2$ alkyl radical;

E is a radical of carboxy or —C(O)—O—$R_{20}$; and $R_{20}$ is a $C_1$–$C_2$ alkyl, aryl or aryl($C_1$–$C_2$ alkyl) radical, wherein the aryl radicals are optionally substituted by 1–3 radicals of $R_2$.

7. A pharmaceutical composition comprising a compound according to any of claims 1 to 6 and a pharmaceutically acceptable carrier.

8. A method for the treatment of rheumatoid arthritis comprising administering an effective amount of a compound according to claim 1.

* * * * *